US007687615B2

(12) United States Patent
Tikoo

(10) Patent No.: US 7,687,615 B2
(45) Date of Patent: Mar. 30, 2010

(54) PAV REGIONS FOR ENCAPSIDATION AND E1 TRANSCRIPTIONAL CONTROL

(75) Inventor: Suresh K. Tikoo, Saskatoon (CA)

(73) Assignee: University of Saskatchewan, Saskatchewan (CA)

(*) Notice: Subject to any disclaimer, the term of this patent is extended or adjusted under 35 U.S.C. 154(b) by 1177 days.

(21) Appl. No.: 10/622,869

(22) Filed: Jul. 18, 2003

(65) Prior Publication Data

US 2004/0214162 A1    Oct. 28, 2004

Related U.S. Application Data

(60) Provisional application No. 60/397,251, filed on Jul. 19, 2002, provisional application No. 60/460,798, filed on Apr. 4, 2003.

(51) Int. Cl.
  *C07H 21/00*    (2006.01)
  *A61K 39/235*   (2006.01)
(52) U.S. Cl. .................... 536/23.72; 424/233.1
(58) Field of Classification Search ............... None
  See application file for complete search history.

(56) References Cited

U.S. PATENT DOCUMENTS

| | | | |
|---|---|---|---|
| 5,462,734 A * | 10/1995 | Letchworth et al. ...... | 424/229.1 |
| 5,820,868 A | 10/1998 | Mittal et al. | |
| 6,001,591 A | 12/1999 | Mittal et al. | |
| 6,350,853 B1 * | 2/2002 | Nielsen et al. ............. | 530/300 |
| 6,492,343 B1 | 12/2002 | Reddy et al. | |
| 2002/0019051 A1 | 2/2002 | Lusky et al. | |

FOREIGN PATENT DOCUMENTS

| | | |
|---|---|---|
| EP | 0 259 149 | 3/1988 |
| WO | WO 99/53047 | 10/1999 |

OTHER PUBLICATIONS

Barton et al. Molecular Therapy, 2006, 13(2):347-356.*
Demberg et al. Journal of Virology, 2007, 81(7):3414-3427.*
St. George, JA, Gene Therapy, 2003,10:1135-1141.*
Verma et al. Nature, 1997, 389:239-242.*
Vorburger et al., The Oncologist, 2002, 7:46-59.*
Human Genome Project Information, Gene Therapy, 2007, 7 pages of internet printout available from www.ornl.gov/sci/techresources/Human_Genome/medicine/genetherapy.shtml).*
GenBank Accession No. AF083132, "Sequence Analysis of Putative pVIII, E3 and Fibre Regions of Porcine Adenovirus Type 3," created on Jan. 3, 1999, located at <http://www.ncbi.nlm.nih.gov.> last visited on Feb. 6, 2003, fourteen pages.
GenBank Accession No. J01917, "The Nucleotide Sequence of a Low Molecular Weight Ribonucleic Acid From Cells Infected with Adenovirus 2," Created on Mar. 14, 1996, located at <http://www.ncbi.nlm.nih.gov.> last visited on Sep. 8, 2003, thirty-seven pages.
GenBank Accession No. M73260, "The Sequence of the Genome of Adenovirus Type 5 and its Comparison with the Genome of Adenovirus Type 2," created on Apr. 8, 1996, located at <http://www.ncbi.nlm.nih.gov> last visited on Oct. 26, 2000, twelve pages.
GenBank Accession No. U34592, "Porcine Adenovirus 3 Hexon Gene, Complete CDS: Direct Submission," Created Jun. 11, 1996, located at <http://www.ncbi.nlm.nih.gov.> last visited on Sep. 8, 2003, three pages.
GenBank Accession No. U82628, "Nucleotide and Amino Acid Sequence Analysis of the 100K Protein of a Serotype 3 Porcine Adenovirus," created on Aug. 5, 1999, located at <http://www.ncbi.nlm.nih.gov.> last visited on Sep. 8, 2003, two pages.
Bartha, A. (1969). "Proposal For Subgrouping of Bovine Adenoviruses," *Acta Vet. Acad. Sci. Hung.* 19(3):319-321.
Berk, A.J. et al. (1979). "Pre-early Adenovirus 5 Gene Product Regulates Synthesis of Early Viral Messenger RNAs," *Cell* 17:935-944.
Berkner, K.L. et al. (1983). "Generation of Adenovirus By Transfection of Plasmids," *Nucleic Acid Research* 11(17):6003-6020.
Bett, A.J. et al. (1993). "Packaging Capacity and Stability of Human Adenovirus Type 5 Vectors," *J. Virology* 67(10):5911-5921.
Bett, A.J. et al. (1993). "Packaging Capacity and Stability of Human Adenovirus Type 5 Vectors," *J. Virology* 67(10):5911-5921.
Boulanger, P.A. and Blair, G.E. (1991). "Expression and Interactions of Human Adenovirus Oncoproteins," *Biochem. J.* 275:281-299.
Braun, R.P. and Lee, J.S. (1988). "Immunogenic Duplex Nucleic Acids Are Nuclease Resistant," *J. Immunol.* 141(6):2084-2089.
Brennan, S. and Savage, R. (1990). "Embryonic Transcriptional Activation of a Xenopus Cytoskeletal Actin Gene Does Not Require a Serum Response Element," *Roux's Arch. Dev. Biol.* 199:89-96.
Chartier, C. et al. (1996). "Efficient Generation of Recombinant Adenovirus Vectors by Homologous Recombination in *Escherichia coli*," *J. Virol.* 70(7):4805-4810.
Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Research* 24(12):2318-2323.
Chiou, S.-K. and White, E. (1997). "p300 Binding by E1A Cosegregates with p53 Induction but Is Dispensable for Apoptosis," *J. Viral.* 71(5):3515-3525.
Clarke, M.C. et al. (1967). "Some Characteristics of Three Porcine Adenoviruses," *Arch Ges. Virusforsch.* 21:91-97.
Clemens, P.R. et al. (1998). "In Vivo Muscle Gene Transfer of Full-Length Dystrophin with an Adenoviral Vector that Lacks all Viral Genes," *Gene Therapy* 3:965-972.
Daniell, E. (1976). "Genome Structure of Incomplete Particles of Adenovirus," *J. Virol.* 19(2):685-708.
Darbyshire, J.H. (1966). "Oncogenicity of Bovine Adenovirus Type 3 in Hamsters," *Nature* 211:102.

(Continued)

*Primary Examiner*—Stacy B Chen
(74) *Attorney, Agent, or Firm*—Morrison & Foerster LLP

(57) ABSTRACT

The present invention provides porcine adenovirus sequence essential for encapsidation and provides adenovirus vectors comprising such sequences. The present invention provides host cells and composition comprising adenovirus vectors comprising porcine adenovirus sequence essential for encapsidation as well as methods for making and using such adenovirus vectors. The present invention discloses porcine adenovirus sequence for E1 transcriptional control and provides porcine adenovirus vectors comprising a modification(s) in the E1 transcriptional control region.

40 Claims, 26 Drawing Sheets

OTHER PUBLICATIONS

Figures 2A, 2B:
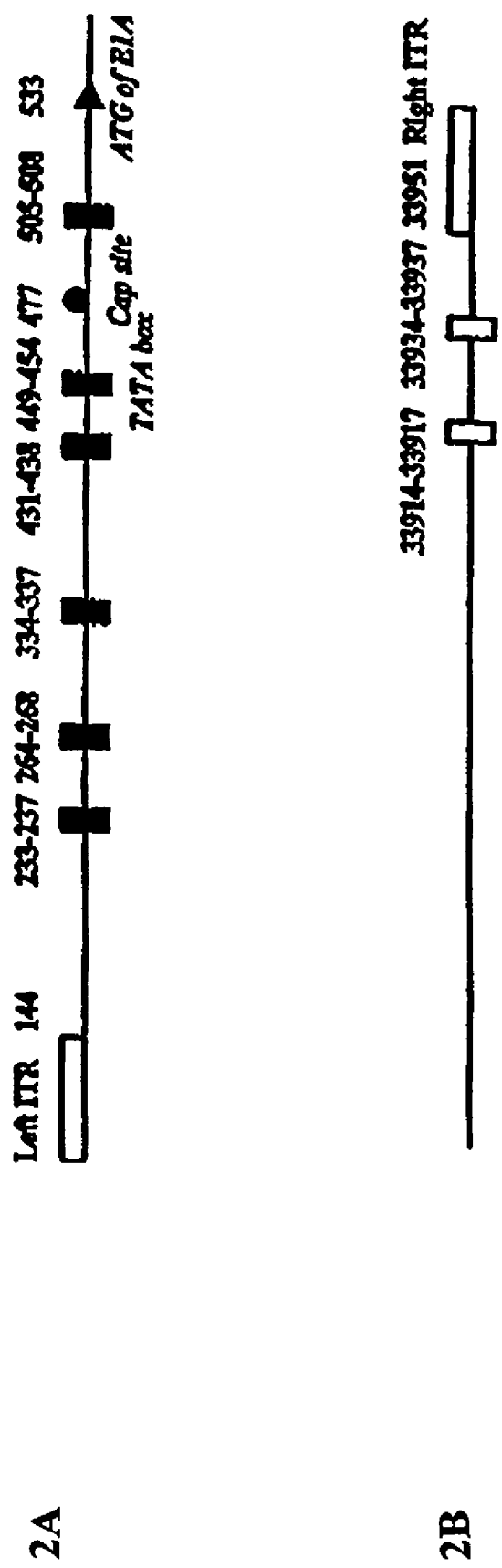

Darbyshire, J.H. et al. (1965). "A New Adenovirus Serotype of Bovine Origin," *J. Comp. Pathol.* 75:327-330.

Darbyshire, J.H. et al. (1966). "The Pathogenesis and Pathology of Infection in Calves with a Strain of Bovine Adenovirus Type 3," *Res. Vet. Sci.* 7:81-93.

Debbas, M. and White, E. (1993). "Wild-Type p53 Mediates Apoptosis by E1A, Which is Inhibited by E1B," *Genes Dev.* 7:546-554.

Derbyshire, J.B. (1992). "Adenovirus" Chapter 11 *In Diseases of Swine* Leman et al. eds., Seventh Edition, Iowa State University Press: Ames, IA, pp. 225-227.

Derbyshire, J.B. et al. (1975). "Serological and Pathogenicity Studies With Some Unclassified Porcine Adenoviruses," *J. Comp. Pathol.* 85:437-443.

D'Halluin, J-C. et al. (1978). "Adenovirus Type 2 Assembly Analyzed by Reversible Cross-Linking of Labile Intermediates," *J. Virol.* 26(2):357-363.

D'Halluin, J-C. et al. (1978). "Temperature-Sensitive Mutant of Adenovirus Type 2 Blocked in Virion Assemby: Accumulation of Light Intermediate Particles," *J. Virol.* 26(2):344-357.

D'Halluin, J-C. et al. (1980). "Morphogenesis of Human Adenovirus Type 2 Studied with Fiber- and Fiber and Penton Base-Defective Temperature-Sensitive Mutants," *J. Virol.* 33(1):88-89.

Edvardsson, B. et al. (1976). "Intermediates in Adenovirus Assembly," *J. Virol.* 19(2):533-547.

Edvardsson, B. et al. (1978). "Assembly Intermediates Among Adenovirus Type 5 Temperature-Sensitive Mutants," *J. Virol.* 25(2):641-651.

Fallaux, F.J. et al. (1996). "Characterization of 911: A New Helper Cell Line for the Titration and Propagation of Early Region 1-Deleted Adenoviral Vectors," *Human Gene Therapy* 7:215-222.

Fallaux, F.J. et al. (1998). "New Helper Cells and Matched Early Region 1-Deleted Adenovirus Vectors Prevent Generation of Replication-Competent Adenoviruses," *Human Gene Therapy* 9:1909-1917.

Foy, H.M. (1989). "Adenoviruses" Chapter 3 *In Viral Infections of Humans*, Evans, A.S., ed., Plenum Medical Book Company: New York, NY pp. 77-89.

Goodrum, F.D. and Ornelles, D.A. (1997). "The Early Region 1B 55-Kilodalton Oncoprotein of Adenovirus Relieves Growth Restrictions Imposed on Viral Replication by the Cell Cycle," *J. Virol.* 71(1):548-561.

Gräble, M. and Hearing, P. (1990). "Adenovirus Type 5 Packaging Domain Is Composed of a Repeated Element That Is Functionally Redundant," *J. Virol.* 64(5):2047-2056.

Gräble, M. and Hearing, P. (1992). "*cis* and *trans* Requirements for the Selective Packaging of Adenovirus Type 5 DNA," *J. Virol.* 66(2):723-731.

Graham, F.L. (1984). "Covalently Closed Circles of Human Adenovirus DNA are Infectious," *EMBO J.* 3(12):2917-2922.

Graham, F.L. et al. (1973). "A New Technique for the Assay of Infectivity of Human Adenovirus 5 DNA," *Virology* 52:456-467.

Graham, F.L. et al. (1977). "Characteristics of a Human Cell Line Transformed by DNA from Human Adenovirus Type 5," *J. Gen. Virol.* 36:59-74.

Guilfoyle, R.A. et al. (1985). "Two Functions Encoded by Adenovirus Early Region 1A are Responsible for the Activation and Repression of the DNA-Binding Protein Gene," *EMBO J.* 4(3):707-713.

Gustin, K.E. and Imperiale, M.J. (1998). "Encapsidation of Viral DNA Requires the Adenovirus L1 52/55-Kilodalton Protein," *J. Virol.* 72(10):7860-7870.

Halbert, D.N. et al. (1985). "Adenovirus Early Region 4 Encodes Functions Required for Efficient DNA Replication, Late Gene Expression, and Host Cell Shutoff," *J. Virol.* 56(1):250-257.

Hammarskjöld, M-L. and Winberg, G. (1980). "Encapsidation of Adenovirus 16 DNA Is Directed by a Small DNA Sequence at the Left End of the Genome," *Cell* 20:787-795.

Hampsey, M. (1998). "Molecular Genetics of the RNA Polymerase II General Transcriptional Machinery," *Microbiol. Mol. Biol. Rev.* 62(2):465-503.

Hatfield, L. and Hearing, P. (1991). "Redundant Elements in the Adenovirus Type 5 Inverted Terminal Repeat Promote Bidirectional Transcription In Vitro and Are Important for Virus Growth In Vivo," *Virology* 184:265-276.

Hearing, P. et al. (1987). "Identification of a Repeated Sequence Element Required for Efficient Encapsidation of the Adenovirus Type 5 Chromosome," *J. Virol.* 61(8):2555-2558.

Hearing, P. and Shenk, T. (1983). "The Adenovirus Type 5 E1A Transcriptional Control Region Contains a Duplicated Enhancer Element," *Cell* 33:695-703.

Hearing, P. and Shenk, T. (1986). "The Adenovirus Type 5 E1A Enhancer Contains Two Functionally Distinct Domains: One is Specific for E1A and the Other Modulates All Early Units in *Cis*," *Cell* 45:229-236.

Hehir, K. M. et al. (1996). "Molecular Characterization of Replication-Competent Variants of Adenovirus Vectors and Genome Modifications To Prevent Their Occurrence," *J. Virol.* 70(12):8459-8467.

Hirahara, T. et al. (1990). "Isolation of Porcine Adenovirus From The Respiratory Tract of Pigs in Japan," *Jpn. J. Vet. Sci.* 52(2):407-409.

Holm, P.S. et al. (2002). "YB-1 Relocates to the Nucleus in Adenovirus-Infected Cells and Facilitates Viral Replication by Inducing E2 Gene Expression Through the E2 Late Promoter," *J. Biol. Chem.* 277(12):10427-10434.

Horwitz, M.S. (1991). "Adenoviridae and Their Replication: Structure of the Virus" Chapter 31 *In Fundamental Virology* Second Edition, Fields, B.N. et al. eds. Raven Press, Ltd.: New York, NY. pp. 771-813.

Hu, S-H. et al. (1984). "Sequence Homology Between Bovine and Human Adenoviruses," *J. Virol.* 49(2):604-608.

Imler, J.L. et al. (1995). "*Trans*-Complementation of E1-Deleted Adenovirus: A New Vector to Reduce the Possibility of Codissemination of Wild-Type and Recombinant Adenoviruses," *Human Gene Therapy* 6:711-721.

Imler, J.L. et al. (1996). "Novel Complementation Cell Lines Derived From Human Lung Carcinoma A549 Cells Support the Growth of E1-Deleted Adenovirus Vectors," *Gene Therapy* 3:75-84.

Jones, N. and Shenk, T. (1979). "An Adenovirus Type 5 Early Gene Function Regulates Expression of Other Early Viral Genes," *Proc. Natl. Acad. Sci. USA* 76(8):3665-3669.

Khoury, G. and Gruss, P. (1983). "Enhancer Elements," *Cell* 33:313-314.

Kim, J.-H. and Chambliss, G.H. (1997). "Contacts Between *Bacillus subtilis* Catabolite Regulatory Protein CcpA and *amyO* Target Site," *Nucleic Acid Res.* 25(17):3490-3496.

Kleiboeker, S.B. (1994). "Sequence Analysis of Putative E3, pVIII, and Fiber Genomic Regions of a Porcine Adenovirus," *Virus Res.* 31:17-25.

Kleiboeker, S.B. (1995). "Identification and Sequence Analysis of the E1 Genomic Region of a Porcine Adenovirus," *Virus Res.* 36:259-268.

Kleiboeker, S.B. (1995). "Sequence Analysis of the Fiber Genomic Region of a Porcine Adenovirus Predicts a Novel Fiber Protein," *Virus Res.* 39:299-309.

Kochanek, S. et al. (1996). "A New Adenoviral Vector: Replacement of all Viral Coding Sequences with 28 kb of DNA Independently Expressing Both Full-Length Dystrophin and β-Galactosidase," *Proc. Natl. Acad. Sci. USA* 93:5731-5736.

Kunkel, T.A. et al. (1987). "Rapid and Efficient Site-Specific Mutagenesis Without Phenotypic Selection," Chapter 19 *In Methods in Enzymology* Academic Press, Inc. vol. 154, pp. 367-382.

Kurokawa, T. et al. (1978). "Biochemical Studies on Bovine Adenovirus Type 3 III. Cleavage Maps of Viral DNA by Restriction Endoncleases *EcoRI*, *Bam*HI, and *Hin*dIII," *J. Virol.* 28(1):212-218.

Laimins, L.A. et al. (1984). "Characterization of Enhancer Elements in the Long Terminal Repeat of Moloney Murine Sarcoma Virus," *J. Virol.* 49(1):183-189.

Latimer, L.J.P. et al. (1995). "Specificity of Monoclonal Antibodies Produced Against Phosphorothioate and RIBO Modified DNAs," *Molec. Immunol.* 32(14/15):1057-1064.

Lowe, S.W. and Ruley, H.E. (1993). "Stabilization of the p53 Tumor Suppressor is Induced by Adenovirus 5 E1A and Accompanies Apoptosis," *Genes Dev.* 7:535-545.

Mattson, D.E. et al. (1988). "Bovine Adenovirus Type-3 Infection in Feedlot Calves," *Am. J. Vet. Res.* 49(1):67-69.

McCoy, R.J. et al. (1996). "Genomic Location and Nucleotide Sequence of a Porcine Adenovirus Penton Base Gene," *Arch. Virol.* 141:1367-1375.

McCoy, R.J. et al. (1996). "Nucleotide and Amino Acid Sequence Analysis of the Porcine Adenovirus 23K Protein," *DNA Seq.* 6:251-254.

Morsy, M.A. et al. (1998). "An Andeoviral Vector Deleted for all Viral Coding Sequences Results in Enhanced Safety and Extended Expression of a Leptin Transgene," *Proc. Natl. Acad. Sci. USA* 95:7866-7871.

Motoi, M. et al. (1972). "Neoplastic Transformation of Hamster Cells In Vitro by Bovine Adenovirus Type-3," *Gann.* 63:415-418.

Niiyama, Y. et al. (1975). "Biochemical Studies on Bovine Adenovirus Type 3 I. Purification and Properties," *J. Virol.* 16(3):621-633.

Parks, R.J. et al. (1996). "A Helper-Dependent Adenovirus Vector System: Removal of Helper Virus by Cre-mediated Excision of the Viral Packaging Signal," *Proc. Natl. Acad. Sci. USA* 93:13565-13570.

Pettersson, U. and Roberts, R.J. (1986). "Adenovirus Gene Expression and Replication: A Historical Review," *In Cancer Cells: DNA Tumor Viruses* Botchan, M. et al., eds., Cold Spring Harbor Laboratory: Cold Spring Harbor, NY, vol. 4, pp. 37-57.

Peyrottes, S. et al. (1996). "Oligodeoxynucleoside Phosphorarnidates (P-NH$_2$): Synthesis and Thermal Stability of Duplexes with DNA and RNA Targets," *Nucleic Acids Res.* 24(10):1841-1848.

Reddy, P.S. et al. (1993). "Restriction Endonuclease Analysis and Molecular Cloning of Porcine Adenovirus Type 3," *Intervirology* 36:161-168.

Reddy, P.S. et al. (1995). "Comparison of the Inverted Terminal Repetition Sequences From Five Porcine Adenovirus Serotypes," *Virology* 212:237-239.

Reddy, P.S. et al. (1995). "Molecular Cloning and Physical Mapping of Porcine Adenovirus Types 1 and 2," *Arch Virol.* 140:195-200.

Reddy, P.S. et al. (1995). "Sequence Analysis of Putative pVIII, E3 and Fibre Regions of Porcine Adenovirus Type 3," *Virus Res.* 36:97-106.

Reddy, P.S. et al. (1996). "Porcine Adenoviruses Types 1, 2 and 3 have Short and Simple Early E-3 Regions," *Virus Res.* 43:99-109.

Reddy, P.S. et al. (1997). "Characterization of the Early Region 4 of Porcine Adenovirus Type 3," *Virus Genes* 15(1):87-90.

Reddy, P.S. et al. (1998). "Nucleotide Sequence, Genome Organization, and Transcription Map of Bovine Adenovirus Type 3," *Journal of Virology* 72(2):1394-1402.

Reddy, P.S. et al. (1998). "Nucleotide Sequence and Transcription Map of Porcine Adenovirus Type 3," *Virology* 251:414-426.

Reddy, P.S. et al. (1998). "Sequence and Transcription Map Analysis of Early Region-1 of Porcine Adenovirus Type-3," *Virus. Res.* 58:97-106.

Reddy, P.S. et al. (1999). "Porcine Adenovirus-3 as a Helper-Dependent Expression Vector," *J. Gen. Virol.* 80:2909-2916.

Reddy, P.S. et al. (1999). "Replication-Defective Bovine Adenovirus Type 3 as an Expression Vector," *Journal of Virology* 73(11):9137-9144.

Rekosh, D.M.K. et al. (1977). "Identification of a Protein Linked to the Ends of Adenovirus DNA," *Cell* 11:283-295.

Robinson, A.J. et al. (1973). "A Circular DNA-Protein Complex from Adenovirus," *Virology* 56:54-69.

Rubin, B.A. (1993). "Clinical Picture and Epidemiology of Adenovirus Infections," *Acta Microbiol. Hung.* 40(4):303-323.

Russell, W.C. (2000). "Update on Adenovirus and its Vectors," *J. Gen. Virol.* 81:2573-2604.

Schmid, S.I. and Hearing, P. (1997). "Bipartite Structure and Functional Independence of Adenovirus Type 5 Packaging Elements," *J. Virol.* 71(5):3375-3384.

Schmid, S.I. and Hearing, P. (1998). "Cellular Components Interact with Adenovirus Type 5 Minimal DNA Packaging Domains," *J. Virol.* 72(8):6339-6347.

Schultz, R.G. and Gryaznov, S.M. (1996). "Oligo-2'-Fluoro-2'-Deoxynucleotide N3'→ P5' Phosphoramidates: Synthesis and Properties," *Nucleic Acids Res.* 24(15):2966-2973.

Shinagawa, M. et al. (1987). "Phylogenetic Relationships Between Adenoviruses as Inferred From Nucleotide Sequences of Inverted Terminal Repeats," *Gene* 55:85-93.

Takiff, H.E. et al. (1981). "Propagation and In Vitro Studies of Previously Non-Cultivable Enteral Adenoviruses in 293 Cells," *The Lancet* 11:832-834.

Tibbetts, C. (1977). "Viral DNA Sequences from Incomplete Particles of Human Adenovirus Type 7," *Cell* 12:243-249.

Tsukamoto, K. and Sugino, Y. (1972). "Nonproductive Infection and Induction of Cellular Deoxyribonucleic Acid Synthesis by Bovine Adenovirus Type 3 in a Contact-Inhibited Mouse Cell Line," *J. Virol.* 9(3):465-473.

Tuboly, T. et al. (1993). "Potential Viral Vectors for the Stimulation of Mucosal Antibody Responses Against Enteric Viral Antigens in Pigs," *Res. In Vet. Sci.* 54:345-350.

Vrati, S. et al. (1995). "Sequence of Ovine Adenovirus Homologs for 100K Hexon Assembly, 33K, pVIII, and Fiber Genes: Early Region E3 Is Not in the Expected Location," *Virology* 209:400-408.

Whyte, P. et al. (1988). "Two Regions of the Adenovirus Early Region 1A Proteins Are Required for Transformation," *J. Virol.* 62(1):257-265.

Wold, W.S.M. and Gooding, L.R. (1991). Minireview: Region E3 of Adenovirus: A Cassette of Genes Involved in Host Immunosurveillance and Virus-Cell Interactions, *Virology* 184:1-8.

Xiang, Z.Q. et al. (1996). "A Replication-Defective Human Adenovirus Recombinant Serves as a Highly Efficacious Vaccine Carrier," *Virology* 219:220-227.

Zhang, W. and Imperiale, M.J. (2000). "Interaction of the Adenovirus IVa2 Protein with Viral Packaging Sequences," *J. Virol.* 74(6):2687-2690.

Zhang, W. et al. (2001). "Role for the Adenovirus IVa2 Protein in Packaging of Viral DNA," *J. Virol.* 75(21):10446-10459.

Zheng, B. et al. (1994). "The E1 Sequence of Bovine Adenovirus Type 3 and Complementation of Human Adenovirus Type 5 E1A Function in Bovine Cells," *Virus Research* 31:163-186.

Zhou, Y. and Tikoo, S.K. (2001). "Analysis of Early Region 1 of Porcine Adenovirus Type 3," *Virology* 291:68-76.

Zoller, M.J. and Smith, M. (1982). "Oligonucleotide-Directed Mutagenesis Using M13-derived Vectors: An Efficient and General Procedure for the Production of Point Mutations in any Fragment of DNA," *Nucleic Acids Res.* 10(20):6487-6500.

International Search Report mailed on Mar. 18, 2004, for PCT Patent Application No. PCT/IB03/03724 filed on Jul. 18, 2003, seven pages.

Reddy, P.S. et al. (1999). "Development of Porcine Adenovirus-3 As An Expression Vector," *Journal of General Virology* 80:563-570.

Tuboly, T. et al. (2001). "Construction and Characterization of Recombinant Porcine Adenovirus Serotype 5 Expressing the Transmissible Gastroenteritis Virus Spike Gene," *Journal of General Virology* 82:183-190.

Xing, L. et al. (2003). "Characterization of cis-acting Sequences Involved in Packaging Porcine Adenovirus Type 3," *Virology* 314:650-661.

* cited by examiner

Figures 1A-1B

1A

CATCATCAAT AAAATACGGC ACACTTTAT TGCCCCTTTT GTGGCGTGGT GATTGGCGGA GAGGGTTGGG GCGGGCGGGC 1-80
GGTGATTGGT CGAGAGCGGT GTGACGTAGC GTGGGAACGT GACGTCGCGT GGGAAATGA CGTGTGATGA CGTCCGGTGG -160
GAACGGGTCA AAGTCCAAGG GGAAGGGGTG GAGCGCCTGGG GCGGTTCTCC GCCAGGGCGGG GCCGAGCCGGC GGAAATTCCC -240
GCACAGGTGG AGAGTACGGC GGGATTTTGT GCCCTCTGGA CCCGCACCTTC GTGGCACTTC CGCACCACAC -320
GTCCGCGGCC CGGTATTCCC CACCTGACGA CGTGACACC ACTCACCTGA GCGGGTGTC CTTCGCGCTG AGAGGTCGGC -400
GCGGGCCGCC CGAGATGACG TGTGTGGGTG TATTTTTTCC CCTCAGTGTA TATAGTCCGC GCAGCGCCG AGAGTCACTA -480
CTCTTGAGTC CGAAGGGAGT AGAGTTTTCT CTCAGCCGAA CAGACCCTCG ACATGCGGAA CAGACTTCAC CTGGACTGGG -560

1B

CCGCCCAGAA GTCCGCGGAA TTCCGGCCAG CCGGCTCCGC CGGGACCTGC GACTTTGACC CCGCCCCTCG 33861-33930
GACTTTGACC GTTCCCACGC CACGTCATTT TCCCACGCGA CGTCACGTTC CCAGCCTACG TCACACCCT -34000
CTCCACCCAAT CACCGCCCGC CGGCCCCCAC CCCTCTCCGC AATCACCACG CCACAAAAGG -34070
GTGTGCGGTA TATTATTGAT GATG -34094

2A

2B

Figure 12

| | | | |
|---|---|---|---|
| 233-237 | CGG | AAAATT | CCCGCACA |
| 264-268 | GGG | ATTTT | GTGCCCTCT |
| 334-337 | CGG | TATT | CCCCACCTG |
| 431-438 | GTG | TATTTTTT | CCCCTCA |
| 449-454 | GTG | TATATA | GTCCGCGC |
| 505-508 | GAG | TTTT | CTCTCAGCCG |

211 GCGGGGGCGGGGGCCGAGCGGCGGGAAATTCCCGCACAGGTGGAGAGTACCGCGGGATTTTGT
                             ────────I─────────              ──────II──────
271 GCCCTCTGGACCGGACCCTTCGCCCTCCGGTGTGGCACTTCCGCACCACGTCCGCGGCC
    ──III──
331 CGGTATTCCCCGACCCACTCACCTGAGCGGGTGTCCTTCGCGCTG
    ────III────
391 AGAGGTCCGGCGCCGCCCGAGATGACGTGTGTGGGTGTATTTTTCCCTCAGTGTA
                                         ──────IV──────
451 TATAGTCCGCGCAGCGCCGAGAGTCACTACTCTTGAGTCCGAAGGGAGTAGAGTTTTCT
    ───V───                                          ──────VI──────
511 CTCAGCCGGAACAGACCCTCG

SEQUENCE LISTING

<160> NUMBER OF SEQ ID NOS: 414

<210> SEQ ID NO 1
<211> LENGTH: 16
<212> TYPE: DNA
<213> ORGANISM: Porcine Adenovirus 3

<400> SEQUENCE: 1
cggaaattcc cgcaca                                                   16

<210> SEQ ID NO 2
<211> LENGTH: 18
<212> TYPE: DNA
<213> ORGANISM: Porcine Adenovirus 3

<400> SEQUENCE: 2
ggcggaaatt cccgcaca                                                 18

<210> SEQ ID NO 3
<211> LENGTH: 17
<212> TYPE: DNA
<213> ORGANISM: Porcine Adenovirus 3

<400> SEQUENCE: 3
gggattttgt gccctct                                                  17

<210> SEQ ID NO 4
<211> LENGTH: 19
<212> TYPE: DNA
<213> ORGANISM: Porcine Adenovirus 3

<400> SEQUENCE: 4
gcgggatttt gtgccctct                                                19

<210> SEQ ID NO 5
<211> LENGTH: 16
<212> TYPE: DNA
<213> ORGANISM: Porcine Adenovirus 3

<400> SEQUENCE: 5
cggtattccc cacctg                                                   16

<210> SEQ ID NO 6
<211> LENGTH: 18
<212> TYPE: DNA
<213> ORGANISM: Porcine Adenovirus 3

<400> SEQUENCE: 6
cccggtattc cccacctg                                                 18

<210> SEQ ID NO 7
<211> LENGTH: 18
<212> TYPE: DNA
<213> ORGANISM: Porcine Adenovirus 3

<400> SEQUENCE: 7
gtgtattttt tcccctca                                                 18

<210> SEQ ID NO 8
<211> LENGTH: 20
<212> TYPE: DNA
<213> ORGANISM: Porcine Adenovirus 3

<400> SEQUENCE: 8
gggtgtattt tttcccctca                                               20

<210> SEQ ID NO 9
<211> LENGTH: 17
<212> TYPE: DNA
<213> ORGANISM: Porcine Adenovirus 3

<400> SEQUENCE: 9
gtgtatatag tccgcgc                                                  17

<210> SEQ ID NO 10
<211> LENGTH: 19
<212> TYPE: DNA
<213> ORGANISM: Porcine Adenovirus 3

<400> SEQUENCE: 10
cagtgtatat agtccgcgc                                                19

<210> SEQ ID NO 11
<211> LENGTH: 16
<212> TYPE: DNA
<213> ORGANISM: Porcine Adenovirus 3

<400> SEQUENCE: 11

```
gagttttctc tcagcg                                                    16

<210> SEQ ID NO 12
<211> LENGTH: 18
<212> TYPE: DNA
<213> ORGANISM: Porcine Adenovirus 3

<400> SEQUENCE: 12
tagagttttc tctcagcg                                                  18

<210> SEQ ID NO 13
<211> LENGTH: 14
<212> TYPE: DNA
<213> ORGANISM: Porcine Adenovirus 5

<400> SEQUENCE: 13
ctggtatttt ccac                                                      14

<210> SEQ ID NO 14
<211> LENGTH: 10
<212> TYPE: DNA
<213> ORGANISM: Porcine Adenovirus 5

<400> SEQUENCE: 14
gtgatattgg                                                           10

<210> SEQ ID NO 15
<211> LENGTH: 12
<212> TYPE: DNA
<213> ORGANISM: Porcine Adenovirus 5

<400> SEQUENCE: 15
cctttacctg gg                                                        12

<210> SEQ ID NO 16
<211> LENGTH: 14
<212> TYPE: DNA
<213> ORGANISM: Porcine Adenovirus 5

<400> SEQUENCE: 16
ctcaatttta ccac                                                      14

<210> SEQ ID NO 17
<211> LENGTH: 15
<212> TYPE: DNA
<213> ORGANISM: Porcine Adenovirus 5

<400> SEQUENCE: 17
ggtcgatttt tccac                                                     15

<210> SEQ ID NO 18
<211> LENGTH: 17
<212> TYPE: DNA
<213> ORGANISM: Porcine Adenovirus 5

<400> SEQUENCE: 18
cctatttatt ctgcgcg                                                   17

<210> SEQ ID NO 19
<211> LENGTH: 14
<212> TYPE: DNA
<213> ORGANISM: Homo Sapien Adenovirus 5
<220> FEATURE:
<221> NAME/KEY: misc_feature
```

```
<222> LOCATION: (5)...(12)
<223> OTHER INFORMATION: n = A,T,C or G

<400> SEQUENCE: 19
tttgnnnnnn nncg                                                    14

<210> SEQ ID NO 20
<211> LENGTH: 18
<212> TYPE: DNA
<213> ORGANISM: Porcine Adenovirus 5

<400> SEQUENCE: 20
ccctatttat tctgcgcg                                                18

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
cgtcttcaag gatcctta                                                18

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
cgcgctgata tcctcctc                                                18

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
ccgcaattgg tcatcacacg tcattttc                                     28

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
ccgcaattgg gggcggggcc gagcggc                                      27

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
ccgcaattgg cggaggaccg ccccagg                                      27

<210> SEQ ID NO 26
```

-continued

```
<211> LENGTH: 26
<212> TYPE: DNA
<213> ORGANISM: Artificial Sequence
<220> FEATURE:
<223> OTHER INFORMATION: Primer

<400> SEQUENCE: 26
ccgcaattga taccgcggga ttttgt                                              26

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
ccgcaattgc tccacctgtg cgggaat                                             27

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
ccgcaattgc accacacgtc cgcgg                                               25

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
ccgcaattgc ggaagtgcca caccgga                                             27

<210> SEQ ID NO 30
<211> LENGTH: 28
<212> TYPE: DNA
<213> ORGANISM: Artificial Sequence
<220> FEATURE:
<223> OTHER INFORMATION: Primer

<400> SEQUENCE: 30
ccgcaattgt cgcgctgaga ggtccgcg                                            28

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
ccgcaattga ggacaccccg ctcaggt                                             27

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
```
ccgcaattgt tttttcccct cagtgtata                29

<210> SEQ ID NO 33
<211> LENGTH: 27
<212> TYPE: DNA
<213> ORGANISM: Artificial Sequence
<220> FEATURE:
<223> OTHER INFORMATION: Primer

<400> SEQUENCE: 33
ccgcaattgt acacccacac acgtcat                  27

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
ccgcaattgt atatagtccg cgca                     24

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
ccgcaattga ctgaggggaa aaaatac                  27

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
ccgcaattgg tcactactct tgagtcc                  27

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
ccgcaattgc gcggactata tacactg                  27

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
ccgcaattgg agtagagttt tctctca                  27

<210> SEQ ID NO 39
<211> LENGTH: 27
<212> TYPE: DNA

```
<213> ORGANISM: Artificial Sequence
<220> FEATURE:
<223> OTHER INFORMATION: Primer

<400> SEQUENCE: 39
ccgcaattgc ttcggactca agagtag                                27

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
ccgcaattga catggcgaac agacttc                                27

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
ccgcctccgc gttaacgatt aacc                                   24

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
agcttttaat taacatcatc                                        20

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
ccgcaattgc gcaggtcgcg gcggagc                                27

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
ccgcaattgc ctcggacttt gaccgt                                 26

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
ccgcaattgg gcggggtcaa agtcgca                                27
```

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
ccgcaattgc cacgtcattt tccca                                   25

<210> SEQ ID NO 47
<211> LENGTH: 47
<212> TYPE: DNA
<213> ORGANISM: Artificial Sequence
<220> FEATURE:
<223> OTHER INFORMATION: Primer

<400> SEQUENCE: 47
cggcgggatc cttaattaac atcatcaata atataccgca cactttt           47

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
gcgtcgactc aaaacaggct ctcat                                   25

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
cgggatccgg ccgctgctgc agct                                    24

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
cggactagtc cgccgctcgg ccc                                     23

<210> SEQ ID NO 51
<211> LENGTH: 27
<212> TYPE: DNA
<213> ORGANISM: Artificial Sequence
<220> FEATURE:
<223> OTHER INFORMATION: Primer

<400> SEQUENCE: 51
cggactagtc ccgcacaggt ggagagt                                 27

<210> SEQ ID NO 52
<211> LENGTH: 27
<212> TYPE: DNA
<213> ORGANISM: Artificial Sequence
<220> FEATURE:

<223> OTHER INFORMATION: Primer

<400> SEQUENCE: 52
cggactagtc ccgcggtact ctccacc                                    27

<210> SEQ ID NO 53
<211> LENGTH: 27
<212> TYPE: DNA
<213> ORGANISM: Artificial Sequence
<220> FEATURE:
<223> OTHER INFORMATION: Primer

<400> SEQUENCE: 53
cggactagtg tgccctctgg accggac                                    27

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
cggactagtc actgagggga aaaaataca                                  29

<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
cggactagtg tccgcgcagc gcccgaga                                   28

<210> SEQ ID NO 56
<211> LENGTH: 27
<212> TYPE: DNA
<213> ORGANISM: Artificial Sequence
<220> FEATURE:
<223> OTHER INFORMATION: Primer

<400> SEQUENCE: 56
cggactagtc tctactccct tcggact                                    27

<210> SEQ ID NO 57
<211> LENGTH: 28
<212> TYPE: DNA
<213> ORGANISM: Artificial Sequence
<220> FEATURE:
<223> OTHER INFORMATION: Primer

<400> SEQUENCE: 57
cggactagtc tctcagcgga acagaccc                                   28

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
cggactagtc tcggccccgc cccg                                       24

<210> SEQ ID NO 59
<211> LENGTH: 27
<212> TYPE: DNA
<213> ORGANISM: Artificial Sequence
<220> FEATURE:
<223> OTHER INFORMATION: Primer

<400> SEQUENCE: 59
cggactagta aattcccgca caggtgg                              27

<210> SEQ ID NO 60
<211> LENGTH: 27
<212> TYPE: DNA
<213> ORGANISM: Artificial Sequence
<220> FEATURE:
<223> OTHER INFORMATION: Primer

<400> SEQUENCE: 60
cggactagtg tactctccac ctgtgcg                              27

<210> SEQ ID NO 61
<211> LENGTH: 27
<212> TYPE: DNA
<213> ORGANISM: Artificial Sequence
<220> FEATURE:
<223> OTHER INFORMATION: Primer

<400> SEQUENCE: 61
cggactagta ttttgtgccc tctggac                              27

<210> SEQ ID NO 62
<211> LENGTH: 29
<212> TYPE: DNA
<213> ORGANISM: Artificial Sequence
<220> FEATURE:
<223> OTHER INFORMATION: Primer

<400> SEQUENCE: 62
cggactagtg gggaaaaaat acacccaca                            29

<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
cggactagtt atatagtccg cgcagcgc                             28

<210> SEQ ID NO 64
<211> LENGTH: 27
<212> TYPE: DNA
<213> ORGANISM: Artificial Sequence
<220> FEATURE:
<223> OTHER INFORMATION: Primer

<400> SEQUENCE: 64
cggactagta ctcccttcgg actcaag                              27

<210> SEQ ID NO 65
<211> LENGTH: 28
<212> TYPE: DNA
<213> ORGANISM: Artificial Sequence
<220> FEATURE:
<223> OTHER INFORMATION: Primer

```
<400> SEQUENCE: 65
cggactagtt tttctctcag cggaacag                                          28

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66
cggactagta atttccgccg ctcg                                              24

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67
cggactagta caggtggaga gtaccgc                                           27

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68
cggactagta aaatcccgcg gtactct                                           27

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
cggactagtt ctggaccgga ccttcgc                                           27

<210> SEQ ID NO 70
<211> LENGTH: 29
<212> TYPE: DNA
<213> ORGANISM: Artificial Sequence
<220> FEATURE:
<223> OTHER INFORMATION: Primer

<400> SEQUENCE: 70
cggactagtt atatacactg agggggaaaa                                        29

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
cggactagtg cagcgcccga gagtcact                                          28

<210> SEQ ID NO 72
<211> LENGTH: 27
```

<212> TYPE: DNA
<213> ORGANISM: Artificial Sequence
<220> FEATURE:
<223> OTHER INFORMATION: Primer

<400> SEQUENCE: 72
cggactagta aaactctact cccttcg                                        27

<210> SEQ ID NO 73
<211> LENGTH: 28
<212> TYPE: DNA
<213> ORGANISM: Artificial Sequence
<220> FEATURE:
<223> OTHER INFORMATION: Primer

<400> SEQUENCE: 73
cggactagta gcggaacaga ccctcgac                                       28

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
cggactagtc gctcggcccc gcc                                            23

<210> SEQ ID NO 75
<211> LENGTH: 26
<212> TYPE: DNA
<213> ORGANISM: Artificial Sequence
<220> FEATURE:
<223> OTHER INFORMATION: Primer

<400> SEQUENCE: 75
cggactagtc acaggtggag agtacc                                         26

<210> SEQ ID NO 76
<211> LENGTH: 27
<212> TYPE: DNA
<213> ORGANISM: Artificial Sequence
<220> FEATURE:
<223> OTHER INFORMATION: Primer

<400> SEQUENCE: 76
cggactagtc ggtactctcc acctgtg                                        27

<210> SEQ ID NO 77
<211> LENGTH: 27
<212> TYPE: DNA
<213> ORGANISM: Artificial Sequence
<220> FEATURE:
<223> OTHER INFORMATION: Primer

<400> SEQUENCE: 77
cggactagtc ctctggaccg gaccttc                                        27

<210> SEQ ID NO 78
<211> LENGTH: 27
<212> TYPE: DNA
<213> ORGANISM: Artificial Sequence
<220> FEATURE:
<223> OTHER INFORMATION: Primer

<400> SEQUENCE: 78
cggactagtg ccgcggacgt gtggtgc                                              27

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
cggactagta cctgacgacg gtgacac                                              27

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
cggactagtc cacacacgtc atctcgg                                              27

<210> SEQ ID NO 81
<211> LENGTH: 26
<212> TYPE: DNA
<213> ORGANISM: Artificial Sequence
<220> FEATURE:
<223> OTHER INFORMATION: Primer

<400> SEQUENCE: 81
cggactagtc tcagtgtata tagtcc                                               26

<210> SEQ ID NO 82
<211> LENGTH: 27
<212> TYPE: DNA
<213> ORGANISM: Artificial Sequence
<220> FEATURE:
<223> OTHER INFORMATION: Primer

<400> SEQUENCE: 82
cggactagtt gagggaaaa aatacac                                               27

<210> SEQ ID NO 83
<211> LENGTH: 28
<212> TYPE: DNA
<213> ORGANISM: Artificial Sequence
<220> FEATURE:
<223> OTHER INFORMATION: Primer

<400> SEQUENCE: 83
cggactagtg cgcagcgccc gagagtca                                             28

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
cggactagtt actcccttcg gactcaa                                              27

<210> SEQ ID NO 85
<211> LENGTH: 28
<212> TYPE: DNA
<213> ORGANISM: Artificial Sequence

```
<220> FEATURE:
<223> OTHER INFORMATION: Primer

<400> SEQUENCE: 85
cggactagtt cagcggaaca gaccctcg                                          28

<210> SEQ ID NO 86
<211> LENGTH: 560
<212> TYPE: DNA
<213> ORGANISM: Porcine Adenovirus 3

<400> SEQUENCE: 86
catcatcaat aatataccgc acacttttat tgcccctttt gtggcgtggt gattggcgga       60
gagggttggg ggcggcgggc ggtgattggt ggagagggt gtgacgtagc gtgggaacgt       120
gacgtcgcgt gggaaaatga cgtgtgatga cgtcccgtgg gaacgggtca aagtccaagg      180
ggaaggggtg gagccctggg gcggtcctcc gcggggcggg gccgagcggc ggaaattccc      240
gcacaggtgg agagtaccgc gggattttgt gccctctgga ccggaccttc gccctccggt      300
gtggcacttc cgcaccacac gtccgcggcc cggtattccc cacctgacga cggtgacacc      360
actcacctga gcggggtgtc cttcgcgctg agaggtccgc ggcggccgcc cgagatgacg      420
tgtgtgggtg tattttttcc cctcagtgta tatagtccgc gcagcgcccg agagtcacta      480
ctcttgagtc cgaagggagt agagttttct ctcagcggaa cagaccctcg acatggcgaa      540
cagacttcac ctggactggg                                                  560

<210> SEQ ID NO 87
<211> LENGTH: 234
<212> TYPE: DNA
<213> ORGANISM: Porcine Adenovirus 3

<400> SEQUENCE: 87
ccgcccagaa gtcccgggaa ttcccgccag ccggctccgc cgcgacctgc gactttgacc      60
ccgcccctcg gactttgacc gttcccacgc cacgtcattt tcccacgcga cgtcacgttc     120
ccacgctacg tcacacccct ctccaccaat caccgcccgc cgcccccaac cctctccgcc     180
aatcaccacg ccacaaaagg ggcaataaaa gtgtgcggta tattattgat gatg           234

<210> SEQ ID NO 88
<211> LENGTH: 120
<212> TYPE: DNA
<213> ORGANISM: Porcine Adenovirus 3

<400> SEQUENCE: 88
gcggggtgtc cttcgcgctg agaggtccgc ggcggccgcc cgagatgacg tgtgtgggtg      60
tattttttcc cctcagtgta tatagtccgc gcagcgcccg agagtcacta ctcttgagtc     120

<210> SEQ ID NO 89
<211> LENGTH: 320
<212> TYPE: DNA
<213> ORGANISM: Porcine Adenovirus 3

<400> SEQUENCE: 89
gcggggcggg gccgagcggc ggaaattccc gcacaggtgg agagtaccgc gggattttgt      60
gccctctgga ccggaccttc gccctccggt gtggcacttc cgcaccacac gtccgcggcc     120
cggtattccc cacctgacga cggtgacacc actcacctga gcggggtgtc cttcgcgctg     180
agaggtccgc ggcggccgcc cgagatgacg tgtgtgggtg tattttttcc cctcagtgta     240
```

```
tatagtccgc gcagcgcccg agagtcacta ctcttgagtc cgaagggagt agagtttct      300 ctcagcggaa cagaccctcg                                                  320

<210> SEQ ID NO 90
<211> LENGTH: 30
<212> TYPE: DNA
<213> ORGANISM: Porcine Adenovirus 3

<400> SEQUENCE: 90
gccgagcggc ggaaattccc gcacaggtgg                                        30

<210> SEQ ID NO 91
<211> LENGTH: 14
<212> TYPE: DNA
<213> ORGANISM: Porcine Adenovirus 3

<400> SEQUENCE: 91
gcggaaattc ccgc                                                         14

<210> SEQ ID NO 92
<211> LENGTH: 51
<212> TYPE: DNA
<213> ORGANISM: Porcine Adenovirus 3

<400> SEQUENCE: 92
gcggcggaaa ttcccgcaca ggtggagagt accgcgggat tttgtgccct c                51

<210> SEQ ID NO 93
<211> LENGTH: 13
<212> TYPE: DNA
<213> ORGANISM: Porcine Adenovirus 3

<400> SEQUENCE: 93
cgggattttg tgc                                                          13

<210> SEQ ID NO 94
<211> LENGTH: 17
<212> TYPE: DNA
<213> ORGANISM: Porcine Adenovirus 3

<400> SEQUENCE: 94
gcggcggaaa ttcccgc                                                      17

<210> SEQ ID NO 95
<211> LENGTH: 18
<212> TYPE: DNA
<213> ORGANISM: Porcine Adenovirus 3

<400> SEQUENCE: 95
gcgggatttt gtgccctc                                                     18

<210> SEQ ID NO 96
<211> LENGTH: 19
<212> TYPE: DNA
<213> ORGANISM: Porcine Adenovirus 3

<400> SEQUENCE: 96
cccggtattc cccacctga                                                    19

<210> SEQ ID NO 97
<211> LENGTH: 11
<212> TYPE: DNA
<213> ORGANISM: Porcine Adenovirus 3
```

<400> SEQUENCE: 97
cggtattccc c						11

<210> SEQ ID NO 98
<211> LENGTH: 32
<212> TYPE: DNA
<213> ORGANISM: Porcine Adenovirus 3

<400> SEQUENCE: 98
ggtgtatttt ttcccctcag tgtatatagt cc						32

<210> SEQ ID NO 99
<211> LENGTH: 14
<212> TYPE: DNA
<213> ORGANISM: Porcine Adenovirus 3

<400> SEQUENCE: 99
agagttttct ctca						14

<210> SEQ ID NO 100
<211> LENGTH: 14
<212> TYPE: DNA
<213> ORGANISM: Porcine Adenovirus 3

<400> SEQUENCE: 100
gtgtattttt tccc						14

<210> SEQ ID NO 101
<211> LENGTH: 13
<212> TYPE: DNA
<213> ORGANISM: Porcine Adenovirus 3

<400> SEQUENCE: 101
gtgtatatag tcc						13

<210> SEQ ID NO 102
<211> LENGTH: 10
<212> TYPE: DNA
<213> ORGANISM: Porcine Adenovirus 3

<400> SEQUENCE: 102 gagttttctc						10

<210> SEQ ID NO 103
<211> LENGTH: 14
<212> TYPE: DNA
<213> ORGANISM: Porcine Adenovirus 3

<400> SEQUENCE: 103
gaaattcccg caca						14

<210> SEQ ID NO 104
<211> LENGTH: 13
<212> TYPE: DNA
<213> ORGANISM: Porcine Adenovirus 3

<400> SEQUENCE: 104
gaaattcccg cac						13

<210> SEQ ID NO 105
<211> LENGTH: 12
<212> TYPE: DNA

<213> ORGANISM: Porcine Adenovirus 3

<400> SEQUENCE: 105
gaaattcccg ca                                                         12

<210> SEQ ID NO 106
<211> LENGTH: 11
<212> TYPE: DNA
<213> ORGANISM: Porcine Adenovirus 3

<400> SEQUENCE: 106
gaaattcccg c                                                          11

<210> SEQ ID NO 107
<211> LENGTH: 10
<212> TYPE: DNA
<213> ORGANISM: Porcine Adenovirus 3

<400> SEQUENCE: 107
gaaattcccg                                                            10

<210> SEQ ID NO 108
<211> LENGTH: 9
<212> TYPE: DNA
<213> ORGANISM: Porcine Adenovirus 3

<400> SEQUENCE: 108 gaaattccc                                                              9

<210> SEQ ID NO 109
<211> LENGTH: 8
<212> TYPE: DNA
<213> ORGANISM: Porcine Adenovirus 3

<400> SEQUENCE: 109 gaaattcc                                                               8

<210> SEQ ID NO 110
<211> LENGTH: 7
<212> TYPE: DNA
<213> ORGANISM: Porcine Adenovirus 3

<400> SEQUENCE: 110 gaaattc                                                                7

<210> SEQ ID NO 111
<211> LENGTH: 15
<212> TYPE: DNA
<213> ORGANISM: Porcine Adenovirus 3

<400> SEQUENCE: 111
ggaaattccc gcaca                                                      15

<210> SEQ ID NO 112
<211> LENGTH: 14
<212> TYPE: DNA
<213> ORGANISM: Porcine Adenovirus 3

<400> SEQUENCE: 112
ggaaattccc gcac                                                       14

<210> SEQ ID NO 113
<211> LENGTH: 13

```
<212> TYPE: DNA
<213> ORGANISM: Porcine Adenovirus 3

<400> SEQUENCE: 113
ggaaattccc gca                                                          13

<210> SEQ ID NO 114
<211> LENGTH: 12
<212> TYPE: DNA
<213> ORGANISM: Porcine Adenovirus 3

<400> SEQUENCE: 114
ggaaattccc gc                                                           12

<210> SEQ ID NO 115
<211> LENGTH: 11
<212> TYPE: DNA
<213> ORGANISM: Porcine Adenovirus 3

<400> SEQUENCE: 115
ggaaattccc g                                                            11

<210> SEQ ID NO 116
<211> LENGTH: 10
<212> TYPE: DNA
<213> ORGANISM: Porcine Adenovirus 3

<400> SEQUENCE: 116
ggaaattccc                                                              10

<210> SEQ ID NO 117
<211> LENGTH: 9
<212> TYPE: DNA
<213> ORGANISM: Porcine Adenovirus 3

<400> SEQUENCE: 117 ggaaattcc                                                                9

<210> SEQ ID NO 118
<211> LENGTH: 8
<212> TYPE: DNA
<213> ORGANISM: Porcine Adenovirus 3

<400> SEQUENCE: 118 ggaaattc                                                                 8

<210> SEQ ID NO 119
<211> LENGTH: 15
<212> TYPE: DNA
<213> ORGANISM: Porcine Adenovirus 3

<400> SEQUENCE: 119
cggaaattcc cgcac                                                        15

<210> SEQ ID NO 120
<211> LENGTH: 14
<212> TYPE: DNA
<213> ORGANISM: Porcine Adenovirus 3

<400> SEQUENCE: 120
cggaaattcc cgca                                                         14

<210> SEQ ID NO 121
```

```
<211> LENGTH: 13
<212> TYPE: DNA
<213> ORGANISM: Porcine Adenovirus 3

<400> SEQUENCE: 121
cggaaattcc cgc                                                              13

<210> SEQ ID NO 122
<211> LENGTH: 12
<212> TYPE: DNA
<213> ORGANISM: Porcine Adenovirus 3

<400> SEQUENCE: 122
cggaaattcc cg                                                               12

<210> SEQ ID NO 123
<211> LENGTH: 11
<212> TYPE: DNA
<213> ORGANISM: Porcine Adenovirus 3

<400> SEQUENCE: 123
cggaaattcc c                                                                11

<210> SEQ ID NO 124
<211> LENGTH: 10
<212> TYPE: DNA
<213> ORGANISM: Porcine Adenovirus 3

<400> SEQUENCE: 124
cggaaattcc                                                                  10

<210> SEQ ID NO 125
<211> LENGTH: 9
<212> TYPE: DNA
<213> ORGANISM: Porcine Adenovirus 3

<400> SEQUENCE: 125 cggaaattc                                                                    9

<210> SEQ ID NO 126
<211> LENGTH: 17
<212> TYPE: DNA
<213> ORGANISM: Porcine Adenovirus 3

<400> SEQUENCE: 126
gcggaaattc ccgcaca                                                          17

<210> SEQ ID NO 127
<211> LENGTH: 16
<212> TYPE: DNA
<213> ORGANISM: Porcine Adenovirus 3

<400> SEQUENCE: 127
gcggaaattc ccgcac                                                           16

<210> SEQ ID NO 128
<211> LENGTH: 15
<212> TYPE: DNA
<213> ORGANISM: Porcine Adenovirus 3

<400> SEQUENCE: 128
gcggaaattc ccgca                                                            15
```

<210> SEQ ID NO 129
<211> LENGTH: 13
<212> TYPE: DNA
<213> ORGANISM: Porcine Adenovirus 3

<400> SEQUENCE: 129
gcggaaattc ccg                                                    13

<210> SEQ ID NO 130
<211> LENGTH: 12
<212> TYPE: DNA
<213> ORGANISM: Porcine Adenovirus 3

<400> SEQUENCE: 130
gcggaaattc cc                                                     12

<210> SEQ ID NO 131
<211> LENGTH: 11
<212> TYPE: DNA
<213> ORGANISM: Porcine Adenovirus 3

<400> SEQUENCE: 131
gcggaaattc c                                                      11

<210> SEQ ID NO 132
<211> LENGTH: 10
<212> TYPE: DNA
<213> ORGANISM: Porcine Adenovirus 3

<400> SEQUENCE: 132
gcggaaattc                                                        10

<210> SEQ ID NO 133
<211> LENGTH: 17
<212> TYPE: DNA
<213> ORGANISM: Porcine Adenovirus 3

<400> SEQUENCE: 133
ggcggaaatt cccgcac                                                17

<210> SEQ ID NO 134
<211> LENGTH: 16
<212> TYPE: DNA
<213> ORGANISM: Porcine Adenovirus 3

<400> SEQUENCE: 134
ggcggaaatt cccgca                                                 16

<210> SEQ ID NO 135
<211> LENGTH: 15
<212> TYPE: DNA
<213> ORGANISM: Porcine Adenovirus 3

<400> SEQUENCE: 135
ggcggaaatt cccgc                                                  15

<210> SEQ ID NO 136
<211> LENGTH: 14
<212> TYPE: DNA
<213> ORGANISM: Porcine Adenovirus 3

<400> SEQUENCE: 136
ggcggaaatt cccg                                                   14

```
<210> SEQ ID NO 137
<211> LENGTH: 13
<212> TYPE: DNA
<213> ORGANISM: Porcine Adenovirus 3

<400> SEQUENCE: 137
ggcggaaatt ccc                                                          13

<210> SEQ ID NO 138
<211> LENGTH: 12
<212> TYPE: DNA
<213> ORGANISM: Porcine Adenovirus 3

<400> SEQUENCE: 138
ggcggaaatt cc                                                           12

<210> SEQ ID NO 139
<211> LENGTH: 11
<212> TYPE: DNA
<213> ORGANISM: Porcine Adenovirus 3

<400> SEQUENCE: 139
ggcggaaatt c                                                            11

<210> SEQ ID NO 140
<211> LENGTH: 15
<212> TYPE: DNA
<213> ORGANISM: Porcine Adenovirus 3

<400> SEQUENCE: 140
gattttgtgc cctct                                                        15

<210> SEQ ID NO 141
<211> LENGTH: 14
<212> TYPE: DNA
<213> ORGANISM: Porcine Adenovirus 3

<400> SEQUENCE: 141
gattttgtgc cctc                                                         14

<210> SEQ ID NO 142
<211> LENGTH: 13
<212> TYPE: DNA
<213> ORGANISM: Porcine Adenovirus 3

<400> SEQUENCE: 142
gattttgtgc cct                                                          13

<210> SEQ ID NO 143
<211> LENGTH: 12
<212> TYPE: DNA
<213> ORGANISM: Porcine Adenovirus 3

<400> SEQUENCE: 143
gattttgtgc cc                                                           12

<210> SEQ ID NO 144
<211> LENGTH: 11
<212> TYPE: DNA
<213> ORGANISM: Porcine Adenovirus 3

<400> SEQUENCE: 144
gattttgtgc c                                                            11
```

<210> SEQ ID NO 145
<211> LENGTH: 10
<212> TYPE: DNA
<213> ORGANISM: Porcine Adenovirus 3

<400> SEQUENCE: 145
gattttgtgc                                                           10

<210> SEQ ID NO 146
<211> LENGTH: 9
<212> TYPE: DNA
<213> ORGANISM: Porcine Adenovirus 3

<400> SEQUENCE: 146 gattttgtg                                                            9

<210> SEQ ID NO 147
<211> LENGTH: 8
<212> TYPE: DNA
<213> ORGANISM: Porcine Adenovirus 3

<400> SEQUENCE: 147 gattttgt                                                             8

<210> SEQ ID NO 148
<211> LENGTH: 7
<212> TYPE: DNA
<213> ORGANISM: Porcine Adenovirus 3

<400> SEQUENCE: 148 gattttg                                                              7

<210> SEQ ID NO 149
<211> LENGTH: 16
<212> TYPE: DNA
<213> ORGANISM: Porcine Adenovirus 3

<400> SEQUENCE: 149
ggattttgtg ccctct                                                    16

<210> SEQ ID NO 150
<211> LENGTH: 15
<212> TYPE: DNA
<213> ORGANISM: Porcine Adenovirus 3

<400> SEQUENCE: 150
ggattttgtg ccctc                                                     15

<210> SEQ ID NO 151
<211> LENGTH: 14
<212> TYPE: DNA
<213> ORGANISM: Porcine Adenovirus 3

<400> SEQUENCE: 151
ggattttgtg ccct                                                      14

<210> SEQ ID NO 152
<211> LENGTH: 13
<212> TYPE: DNA
<213> ORGANISM: Porcine Adenovirus 3

<400> SEQUENCE: 152

-continued ggattttgtg ccc                                                          13

<210> SEQ ID NO 153
<211> LENGTH: 12
<212> TYPE: DNA
<213> ORGANISM: Porcine Adenovirus 3

<400> SEQUENCE: 153
ggattttgtg cc                                                           12

<210> SEQ ID NO 154
<211> LENGTH: 11
<212> TYPE: DNA
<213> ORGANISM: Porcine Adenovirus 3

<400> SEQUENCE: 154
ggattttgtg c                                                            11

<210> SEQ ID NO 155
<211> LENGTH: 10
<212> TYPE: DNA
<213> ORGANISM: Porcine Adenovirus 3

<400> SEQUENCE: 155
ggattttgtg                                                              10

<210> SEQ ID NO 156
<211> LENGTH: 9
<212> TYPE: DNA
<213> ORGANISM: Porcine Adenovirus 3

<400> SEQUENCE: 156 ggattttgt                                                                9

<210> SEQ ID NO 157
<211> LENGTH: 8
<212> TYPE: DNA
<213> ORGANISM: Porcine Adenovirus 3

<400> SEQUENCE: 157 ggattttg                                                                 8

<210> SEQ ID NO 158
<211> LENGTH: 16
<212> TYPE: DNA
<213> ORGANISM: Porcine Adenovirus 3

<400> SEQUENCE: 158
gggattttgt gccctc                                                       16

<210> SEQ ID NO 159
<211> LENGTH: 15
<212> TYPE: DNA
<213> ORGANISM: Porcine Adenovirus 3

<400> SEQUENCE: 159
gggattttgt gccct                                                        15

<210> SEQ ID NO 160
<211> LENGTH: 14
<212> TYPE: DNA
<213> ORGANISM: Porcine Adenovirus 3

<400> SEQUENCE: 160

```
gggattttgt gccc                                                    14

<210> SEQ ID NO 161
<211> LENGTH: 13
<212> TYPE: DNA
<213> ORGANISM: Porcine Adenovirus 3

<400> SEQUENCE: 161
gggattttgt gcc                                                     13

<210> SEQ ID NO 162
<211> LENGTH: 12
<212> TYPE: DNA
<213> ORGANISM: Porcine Adenovirus 3

<400> SEQUENCE: 162
gggattttgt gc                                                      12

<210> SEQ ID NO 163
<211> LENGTH: 11
<212> TYPE: DNA
<213> ORGANISM: Porcine Adenovirus 3

<400> SEQUENCE: 163
gggattttgt g                                                       11

<210> SEQ ID NO 164
<211> LENGTH: 10
<212> TYPE: DNA
<213> ORGANISM: Porcine Adenovirus 3

<400> SEQUENCE: 164
gggattttgt                                                         10

<210> SEQ ID NO 165
<211> LENGTH: 9
<212> TYPE: DNA
<213> ORGANISM: Porcine Adenovirus 3

<400> SEQUENCE: 165 gggattttg                                                           9

<210> SEQ ID NO 166
<211> LENGTH: 18
<212> TYPE: DNA
<213> ORGANISM: Porcine Adenovirus 3

<400> SEQUENCE: 166
cgggattttg tgccctct                                                18

<210> SEQ ID NO 167
<211> LENGTH: 17
<212> TYPE: DNA
<213> ORGANISM: Porcine Adenovirus 3

<400> SEQUENCE: 167
cgggattttg tgccctc                                                 17

<210> SEQ ID NO 168
<211> LENGTH: 16
<212> TYPE: DNA
<213> ORGANISM: Porcine Adenovirus 3
```

```
<400> SEQUENCE: 168
cgggattttg tgccct                                                       16

<210> SEQ ID NO 169
<211> LENGTH: 15
<212> TYPE: DNA
<213> ORGANISM: Porcine Adenovirus 3

<400> SEQUENCE: 169
cgggattttg tgccc                                                        15

<210> SEQ ID NO 170
<211> LENGTH: 14
<212> TYPE: DNA
<213> ORGANISM: Porcine Adenovirus 3

<400> SEQUENCE: 170
cgggattttg tgcc                                                         14

<210> SEQ ID NO 171
<211> LENGTH: 13
<212> TYPE: DNA
<213> ORGANISM: Porcine Adenovirus 3

<400> SEQUENCE: 171
cgggattttg tgc                                                          13

<210> SEQ ID NO 172
<211> LENGTH: 12
<212> TYPE: DNA
<213> ORGANISM: Porcine Adenovirus 3

<400> SEQUENCE: 172
cgggattttg tg                                                           12

<210> SEQ ID NO 173
<211> LENGTH: 11
<212> TYPE: DNA
<213> ORGANISM: Porcine Adenovirus 3

<400> SEQUENCE: 173
cgggattttg t                                                            11

<210> SEQ ID NO 174
<211> LENGTH: 10
<212> TYPE: DNA
<213> ORGANISM: Porcine Adenovirus 3

<400> SEQUENCE: 174
cgggattttg                                                              10

<210> SEQ ID NO 175
<211> LENGTH: 17
<212> TYPE: DNA
<213> ORGANISM: Porcine Adenovirus 3

<400> SEQUENCE: 175
gcgggatttt gtgccct                                                      17

<210> SEQ ID NO 176
<211> LENGTH: 16
<212> TYPE: DNA
<213> ORGANISM: Porcine Adenovirus 3
```

-continued

<400> SEQUENCE: 176
gcgggatttt gtgccc         16

<210> SEQ ID NO 177
<211> LENGTH: 15
<212> TYPE: DNA
<213> ORGANISM: Porcine Adenovirus 3

<400> SEQUENCE: 177
gcgggatttt gtgcc          15

<210> SEQ ID NO 178
<211> LENGTH: 14
<212> TYPE: DNA
<213> ORGANISM: Porcine Adenovirus 3

<400> SEQUENCE: 178
gcgggatttt gtgc           14

<210> SEQ ID NO 179
<211> LENGTH: 13
<212> TYPE: DNA
<213> ORGANISM: Porcine Adenovirus 3

<400> SEQUENCE: 179
gcgggatttt gtg            13

<210> SEQ ID NO 180
<211> LENGTH: 12
<212> TYPE: DNA
<213> ORGANISM: Porcine Adenovirus 3

<400> SEQUENCE: 180
gcgggatttt gt             12

<210> SEQ ID NO 181
<211> LENGTH: 11
<212> TYPE: DNA
<213> ORGANISM: Porcine Adenovirus 3

<400> SEQUENCE: 181
gcgggatttt g              11

<210> SEQ ID NO 182
<211> LENGTH: 14
<212> TYPE: DNA
<213> ORGANISM: Porcine Adenovirus 3

<400> SEQUENCE: 182
gtattcccca cctg           14

<210> SEQ ID NO 183
<211> LENGTH: 13
<212> TYPE: DNA
<213> ORGANISM: Porcine Adenovirus 3

<400> SEQUENCE: 183
gtattcccca cct            13

<210> SEQ ID NO 184
<211> LENGTH: 12
<212> TYPE: DNA

<213> ORGANISM: Porcine Adenovirus 3

<400> SEQUENCE: 184
gtattcccca cc                                                              12

<210> SEQ ID NO 185
<211> LENGTH: 11
<212> TYPE: DNA
<213> ORGANISM: Porcine Adenovirus 3

<400> SEQUENCE: 185
gtattcccca c                                                               11

<210> SEQ ID NO 186
<211> LENGTH: 10
<212> TYPE: DNA
<213> ORGANISM: Porcine Adenovirus 3

<400> SEQUENCE: 186
gtattcccca                                                                 10

<210> SEQ ID NO 187
<211> LENGTH: 9
<212> TYPE: DNA
<213> ORGANISM: Porcine Adenovirus 3

<400> SEQUENCE: 187 gtattcccc                                                                   9

<210> SEQ ID NO 188
<211> LENGTH: 8
<212> TYPE: DNA
<213> ORGANISM: Porcine Adenovirus 3

<400> SEQUENCE: 188 gtattccc                                                                    8

<210> SEQ ID NO 189
<211> LENGTH: 7
<212> TYPE: DNA
<213> ORGANISM: Porcine Adenovirus 3

<400> SEQUENCE: 189 gtattcc                                                                     7

<210> SEQ ID NO 190
<211> LENGTH: 6
<212> TYPE: DNA
<213> ORGANISM: Porcine Adenovirus 3

<400> SEQUENCE: 190 gtattc                                                                      6

<210> SEQ ID NO 191
<211> LENGTH: 15
<212> TYPE: DNA
<213> ORGANISM: Porcine Adenovirus 3

<400> SEQUENCE: 191
ggtattcccc acctg                                                           15

<210> SEQ ID NO 192
<211> LENGTH: 14

<212> TYPE: DNA
<213> ORGANISM: Porcine Adenovirus 3

<400> SEQUENCE: 192
ggtattcccc acct                                                                14

<210> SEQ ID NO 193
<211> LENGTH: 13
<212> TYPE: DNA
<213> ORGANISM: Porcine Adenovirus 3

<400> SEQUENCE: 193
ggtattcccc acc                                                                 13

<210> SEQ ID NO 194
<211> LENGTH: 12
<212> TYPE: DNA
<213> ORGANISM: Porcine Adenovirus 3

<400> SEQUENCE: 194
ggtattcccc ac                                                                  12

<210> SEQ ID NO 195
<211> LENGTH: 11
<212> TYPE: DNA
<213> ORGANISM: Porcine Adenovirus 3

<400> SEQUENCE: 195
ggtattcccc a                                                                   11

<210> SEQ ID NO 196
<211> LENGTH: 10
<212> TYPE: DNA
<213> ORGANISM: Porcine Adenovirus 3

<400> SEQUENCE: 196
ggtattcccc                                                                     10

<210> SEQ ID NO 197
<211> LENGTH: 9
<212> TYPE: DNA
<213> ORGANISM: Porcine Adenovirus 3

<400> SEQUENCE: 197 ggtattccc                                                                       9

<210> SEQ ID NO 198
<211> LENGTH: 8
<212> TYPE: DNA
<213> ORGANISM: Porcine Adenovirus 3

<400> SEQUENCE: 198 ggtattcc                                                                        8

<210> SEQ ID NO 199
<211> LENGTH: 7
<212> TYPE: DNA
<213> ORGANISM: Porcine Adenovirus 3

<400> SEQUENCE: 199 ggtattc                                                                         7

<210> SEQ ID NO 200

```
<211> LENGTH: 15
<212> TYPE: DNA
<213> ORGANISM: Porcine Adenovirus 3

<400> SEQUENCE: 200
cggtattccc cacct                                                     15

<210> SEQ ID NO 201
<211> LENGTH: 14
<212> TYPE: DNA
<213> ORGANISM: Porcine Adenovirus 3

<400> SEQUENCE: 201
cggtattccc cacc                                                      14

<210> SEQ ID NO 202
<211> LENGTH: 13
<212> TYPE: DNA
<213> ORGANISM: Porcine Adenovirus 3

<400> SEQUENCE: 202
cggtattccc cac                                                       13

<210> SEQ ID NO 203
<211> LENGTH: 12
<212> TYPE: DNA
<213> ORGANISM: Porcine Adenovirus 3

<400> SEQUENCE: 203
cggtattccc ca                                                        12

<210> SEQ ID NO 204
<211> LENGTH: 10
<212> TYPE: DNA
<213> ORGANISM: Porcine Adenovirus 3

<400> SEQUENCE: 204
cggtattccc                                                           10

<210> SEQ ID NO 205
<211> LENGTH: 9
<212> TYPE: DNA
<213> ORGANISM: Porcine Adenovirus 3

<400> SEQUENCE: 205 cggtattcc                                                             9

<210> SEQ ID NO 206
<211> LENGTH: 8
<212> TYPE: DNA
<213> ORGANISM: Porcine Adenovirus 3

<400> SEQUENCE: 206 cggtattc                                                              8

<210> SEQ ID NO 207
<211> LENGTH: 17
<212> TYPE: DNA
<213> ORGANISM: Porcine Adenovirus 3

<400> SEQUENCE: 207
ccggtattcc ccacctg                                                   17
```

```
<210> SEQ ID NO 208
<211> LENGTH: 16
<212> TYPE: DNA
<213> ORGANISM: Porcine Adenovirus 3

<400> SEQUENCE: 208
ccggtattcc ccacct                                                    16

<210> SEQ ID NO 209
<211> LENGTH: 15
<212> TYPE: DNA
<213> ORGANISM: Porcine Adenovirus 3

<400> SEQUENCE: 209
ccggtattcc ccacc                                                     15

<210> SEQ ID NO 210
<211> LENGTH: 14
<212> TYPE: DNA
<213> ORGANISM: Porcine Adenovirus 3

<400> SEQUENCE: 210
ccggtattcc ccac                                                      14

<210> SEQ ID NO 211
<211> LENGTH: 13
<212> TYPE: DNA
<213> ORGANISM: Porcine Adenovirus 3

<400> SEQUENCE: 211
ccggtattcc cca                                                       13

<210> SEQ ID NO 212
<211> LENGTH: 12
<212> TYPE: DNA
<213> ORGANISM: Porcine Adenovirus 3

<400> SEQUENCE: 212
ccggtattcc cc                                                        12

<210> SEQ ID NO 213
<211> LENGTH: 11
<212> TYPE: DNA
<213> ORGANISM: Porcine Adenovirus 3

<400> SEQUENCE: 213
ccggtattcc c                                                         11

<210> SEQ ID NO 214
<211> LENGTH: 10
<212> TYPE: DNA
<213> ORGANISM: Porcine Adenovirus 3

<400> SEQUENCE: 214
ccggtattcc                                                           10

<210> SEQ ID NO 215
<211> LENGTH: 9
<212> TYPE: DNA
<213> ORGANISM: Porcine Adenovirus 3

<400> SEQUENCE: 215 ccggtattc                                                             9
```

```
<210> SEQ ID NO 216
<211> LENGTH: 17
<212> TYPE: DNA
<213> ORGANISM: Porcine Adenovirus 3

<400> SEQUENCE: 216
cccggtattc cccacct                                                   17

<210> SEQ ID NO 217
<211> LENGTH: 16
<212> TYPE: DNA
<213> ORGANISM: Porcine Adenovirus 3

<400> SEQUENCE: 217
cccggtattc cccacc                                                    16

<210> SEQ ID NO 218
<211> LENGTH: 15
<212> TYPE: DNA
<213> ORGANISM: Porcine Adenovirus 3

<400> SEQUENCE: 218
cccggtattc cccac                                                     15

<210> SEQ ID NO 219
<211> LENGTH: 14
<212> TYPE: DNA
<213> ORGANISM: Porcine Adenovirus 3

<400> SEQUENCE: 219
cccggtattc ccca                                                      14

<210> SEQ ID NO 220
<211> LENGTH: 13
<212> TYPE: DNA
<213> ORGANISM: Porcine Adenovirus 3

<400> SEQUENCE: 220
cccggtattc ccc                                                       13

<210> SEQ ID NO 221
<211> LENGTH: 12
<212> TYPE: DNA
<213> ORGANISM: Porcine Adenovirus 3

<400> SEQUENCE: 221
cccggtattc cc                                                        12

<210> SEQ ID NO 222
<211> LENGTH: 11
<212> TYPE: DNA
<213> ORGANISM: Porcine Adenovirus 3

<400> SEQUENCE: 222
cccggtattc c                                                         11

<210> SEQ ID NO 223
<211> LENGTH: 10
<212> TYPE: DNA
<213> ORGANISM: Porcine Adenovirus 3

<400> SEQUENCE: 223
cccggtattc                                                           10
```

<210> SEQ ID NO 224
<211> LENGTH: 16
<212> TYPE: DNA
<213> ORGANISM: Porcine Adenovirus 3

<400> SEQUENCE: 224 gtatttttc ccctca                                                    16

<210> SEQ ID NO 225
<211> LENGTH: 15
<212> TYPE: DNA
<213> ORGANISM: Porcine Adenovirus 3

<400> SEQUENCE: 225 gtatttttc ccctc                                                     15

<210> SEQ ID NO 226
<211> LENGTH: 14
<212> TYPE: DNA
<213> ORGANISM: Porcine Adenovirus 3

<400> SEQUENCE: 226 gtatttttc ccct                                                      14

<210> SEQ ID NO 227
<211> LENGTH: 13
<212> TYPE: DNA
<213> ORGANISM: Porcine Adenovirus 3

<400> SEQUENCE: 227 gtatttttc ccc                                                       13

<210> SEQ ID NO 228
<211> LENGTH: 12
<212> TYPE: DNA
<213> ORGANISM: Porcine Adenovirus 3

<400> SEQUENCE: 228 gtatttttc cc                                                        12

<210> SEQ ID NO 229
<211> LENGTH: 11
<212> TYPE: DNA
<213> ORGANISM: Porcine Adenovirus 3

<400> SEQUENCE: 229 gtatttttc c                                                         11

<210> SEQ ID NO 230
<211> LENGTH: 10
<212> TYPE: DNA
<213> ORGANISM: Porcine Adenovirus 3

<400> SEQUENCE: 230
gtatttttc                                                           10

<210> SEQ ID NO 231
<211> LENGTH: 17
<212> TYPE: DNA
<213> ORGANISM: Porcine Adenovirus 3

<400> SEQUENCE: 231

```
tgtattttt ccccctca                                              17

<210> SEQ ID NO 232
<211> LENGTH: 16
<212> TYPE: DNA
<213> ORGANISM: Porcine Adenovirus 3

<400> SEQUENCE: 232 tgtattttt ccccctc                                               16

<210> SEQ ID NO 233
<211> LENGTH: 15
<212> TYPE: DNA
<213> ORGANISM: Porcine Adenovirus 3

<400> SEQUENCE: 233 tgtattttt ccccct                                                15

<210> SEQ ID NO 234
<211> LENGTH: 14
<212> TYPE: DNA
<213> ORGANISM: Porcine Adenovirus 3

<400> SEQUENCE: 234 tgtattttt cccc                                                  14

<210> SEQ ID NO 235
<211> LENGTH: 13
<212> TYPE: DNA
<213> ORGANISM: Porcine Adenovirus 3

<400> SEQUENCE: 235 tgtattttt ccc                                                   13

<210> SEQ ID NO 236
<211> LENGTH: 12
<212> TYPE: DNA
<213> ORGANISM: Porcine Adenovirus 3

<400> SEQUENCE: 236 tgtattttt cc                                                    12

<210> SEQ ID NO 237
<211> LENGTH: 11
<212> TYPE: DNA
<213> ORGANISM: Porcine Adenovirus 3

<400> SEQUENCE: 237 tgtattttt c                                                     11

<210> SEQ ID NO 238
<211> LENGTH: 17
<212> TYPE: DNA
<213> ORGANISM: Porcine Adenovirus 3

<400> SEQUENCE: 238
gtgtattttt tccctc                                               17

<210> SEQ ID NO 239
<211> LENGTH: 16
<212> TYPE: DNA
<213> ORGANISM: Porcine Adenovirus 3

<400> SEQUENCE: 239
```

```
gtgtatttt tccccct                                                    16

<210> SEQ ID NO 240
<211> LENGTH: 15
<212> TYPE: DNA
<213> ORGANISM: Porcine Adenovirus 3

<400> SEQUENCE: 240 gtgtatttt tcccc                                                      15

<210> SEQ ID NO 241
<211> LENGTH: 13
<212> TYPE: DNA
<213> ORGANISM: Porcine Adenovirus 3

<400> SEQUENCE: 241 gtgtatttt tcc                                                        13

<210> SEQ ID NO 242
<211> LENGTH: 12
<212> TYPE: DNA
<213> ORGANISM: Porcine Adenovirus 3

<400> SEQUENCE: 242 gtgtatttt tc                                                         12

<210> SEQ ID NO 243
<211> LENGTH: 19
<212> TYPE: DNA
<213> ORGANISM: Porcine Adenovirus 3

<400> SEQUENCE: 243 ggtgtattt ttccccctca                                                 19

<210> SEQ ID NO 244
<211> LENGTH: 18
<212> TYPE: DNA
<213> ORGANISM: Porcine Adenovirus 3

<400> SEQUENCE: 244 ggtgtattt ttcccctc                                                   18

<210> SEQ ID NO 245
<211> LENGTH: 17
<212> TYPE: DNA
<213> ORGANISM: Porcine Adenovirus 3

<400> SEQUENCE: 245 ggtgtattt ttccct                                                     17

<210> SEQ ID NO 246
<211> LENGTH: 16
<212> TYPE: DNA
<213> ORGANISM: Porcine Adenovirus 3

<400> SEQUENCE: 246 ggtgtattt ttcccc                                                     16

<210> SEQ ID NO 247
<211> LENGTH: 15
<212> TYPE: DNA
<213> ORGANISM: Porcine Adenovirus 3
```

<400> SEQUENCE: 247
ggtgtatttt ttccc            15

<210> SEQ ID NO 248
<211> LENGTH: 14
<212> TYPE: DNA
<213> ORGANISM: Porcine Adenovirus 3

<400> SEQUENCE: 248
ggtgtatttt ttcc            14

<210> SEQ ID NO 249
<211> LENGTH: 13
<212> TYPE: DNA
<213> ORGANISM: Porcine Adenovirus 3

<400> SEQUENCE: 249
ggtgtatttt ttc            13

<210> SEQ ID NO 250
<211> LENGTH: 19
<212> TYPE: DNA
<213> ORGANISM: Porcine Adenovirus 3

<400> SEQUENCE: 250
gggtgtattt tttcccctc            19

<210> SEQ ID NO 251
<211> LENGTH: 18
<212> TYPE: DNA
<213> ORGANISM: Porcine Adenovirus 3

<400> SEQUENCE: 251
gggtgtattt tttcccct            18

<210> SEQ ID NO 252
<211> LENGTH: 17
<212> TYPE: DNA
<213> ORGANISM: Porcine Adenovirus 3

<400> SEQUENCE: 252
gggtgtattt tttcccc            17

<210> SEQ ID NO 253
<211> LENGTH: 16
<212> TYPE: DNA
<213> ORGANISM: Porcine Adenovirus 3

<400> SEQUENCE: 253
gggtgtattt tttccc            16

<210> SEQ ID NO 254
<211> LENGTH: 15
<212> TYPE: DNA
<213> ORGANISM: Porcine Adenovirus 3

<400> SEQUENCE: 254
gggtgtattt tttcc            15

<210> SEQ ID NO 255
<211> LENGTH: 14
<212> TYPE: DNA
<213> ORGANISM: Porcine Adenovirus 3

<400> SEQUENCE: 255
gggtgtattt tttc                                              14

<210> SEQ ID NO 256
<211> LENGTH: 15
<212> TYPE: DNA
<213> ORGANISM: Porcine Adenovirus 3

<400> SEQUENCE: 256
gtatatagtc cgcgc                                             15

<210> SEQ ID NO 257
<211> LENGTH: 14
<212> TYPE: DNA
<213> ORGANISM: Porcine Adenovirus 3

<400> SEQUENCE: 257
gtatatagtc cgcg                                              14

<210> SEQ ID NO 258
<211> LENGTH: 13
<212> TYPE: DNA
<213> ORGANISM: Porcine Adenovirus 3

<400> SEQUENCE: 258
gtatatagtc cgc                                               13

<210> SEQ ID NO 259
<211> LENGTH: 12
<212> TYPE: DNA
<213> ORGANISM: Porcine Adenovirus 3

<400> SEQUENCE: 259
gtatatagtc cg                                                12

<210> SEQ ID NO 260
<211> LENGTH: 11
<212> TYPE: DNA
<213> ORGANISM: Porcine Adenovirus 3

<400> SEQUENCE: 260
gtatatagtc c                                                 11

<210> SEQ ID NO 261
<211> LENGTH: 10
<212> TYPE: DNA
<213> ORGANISM: Porcine Adenovirus 3

<400> SEQUENCE: 261
gtatatagtc                                                   10

<210> SEQ ID NO 262
<211> LENGTH: 9
<212> TYPE: DNA
<213> ORGANISM: Porcine Adenovirus 3

<400> SEQUENCE: 262 gtatatagt                                                     9

<210> SEQ ID NO 263
<211> LENGTH: 8
<212> TYPE: DNA

<213> ORGANISM: Porcine Adenovirus 3

<400> SEQUENCE: 263 gtatatag                                                                8

<210> SEQ ID NO 264
<211> LENGTH: 16
<212> TYPE: DNA
<213> ORGANISM: Porcine Adenovirus 3

<400> SEQUENCE: 264
tgtatatagt ccgcgc                                                      16

<210> SEQ ID NO 265
<211> LENGTH: 15
<212> TYPE: DNA
<213> ORGANISM: Porcine Adenovirus 3

<400> SEQUENCE: 265
tgtatatagt ccgcg                                                       15

<210> SEQ ID NO 266
<211> LENGTH: 14
<212> TYPE: DNA
<213> ORGANISM: Porcine Adenovirus 3

<400> SEQUENCE: 266
tgtatatagt ccgc                                                        14

<210> SEQ ID NO 267
<211> LENGTH: 13
<212> TYPE: DNA
<213> ORGANISM: Porcine Adenovirus 3

<400> SEQUENCE: 267
tgtatatagt ccg                                                         13

<210> SEQ ID NO 268
<211> LENGTH: 12
<212> TYPE: DNA
<213> ORGANISM: Porcine Adenovirus 3

<400> SEQUENCE: 268
tgtatatagt cc                                                          12

<210> SEQ ID NO 269
<211> LENGTH: 11
<212> TYPE: DNA
<213> ORGANISM: Porcine Adenovirus 3

<400> SEQUENCE: 269
tgtatatagt c                                                           11

<210> SEQ ID NO 270
<211> LENGTH: 10
<212> TYPE: DNA
<213> ORGANISM: Porcine Adenovirus 3

<400> SEQUENCE: 270
tgtatatagt                                                             10

<210> SEQ ID NO 271
<211> LENGTH: 9

```
<212> TYPE: DNA
<213> ORGANISM: Porcine Adenovirus 3

<400> SEQUENCE: 271 tgtatatag                                                                  9

<210> SEQ ID NO 272
<211> LENGTH: 16
<212> TYPE: DNA
<213> ORGANISM: Porcine Adenovirus 3

<400> SEQUENCE: 272
gtgtatatag tccgcg                                                         16

<210> SEQ ID NO 273
<211> LENGTH: 15
<212> TYPE: DNA
<213> ORGANISM: Porcine Adenovirus 3

<400> SEQUENCE: 273
gtgtatatag tccgc                                                          15

<210> SEQ ID NO 274
<211> LENGTH: 14
<212> TYPE: DNA
<213> ORGANISM: Porcine Adenovirus 3

<400> SEQUENCE: 274
gtgtatatag tccg                                                           14

<210> SEQ ID NO 275
<211> LENGTH: 12
<212> TYPE: DNA
<213> ORGANISM: Porcine Adenovirus 3

<400> SEQUENCE: 275
gtgtatatag tc                                                             12

<210> SEQ ID NO 276
<211> LENGTH: 11
<212> TYPE: DNA
<213> ORGANISM: Porcine Adenovirus 3

<400> SEQUENCE: 276
gtgtatatag t                                                              11

<210> SEQ ID NO 277
<211> LENGTH: 10
<212> TYPE: DNA
<213> ORGANISM: Porcine Adenovirus 3

<400> SEQUENCE: 277
gtgtatatag                                                                10

<210> SEQ ID NO 278
<211> LENGTH: 18
<212> TYPE: DNA
<213> ORGANISM: Porcine Adenovirus 3

<400> SEQUENCE: 278
agtgtatata gtccgcgc                                                       18

<210> SEQ ID NO 279
```

```
<211> LENGTH: 17
<212> TYPE: DNA
<213> ORGANISM: Porcine Adenovirus 3

<400> SEQUENCE: 279
agtgtatata gtccgcg                                                      17

<210> SEQ ID NO 280
<211> LENGTH: 16
<212> TYPE: DNA
<213> ORGANISM: Porcine Adenovirus 3

<400> SEQUENCE: 280
agtgtatata gtccgc                                                       16

<210> SEQ ID NO 281
<211> LENGTH: 15
<212> TYPE: DNA
<213> ORGANISM: Porcine Adenovirus 3

<400> SEQUENCE: 281
agtgtatata gtccg                                                        15

<210> SEQ ID NO 282
<211> LENGTH: 14
<212> TYPE: DNA
<213> ORGANISM: Porcine Adenovirus 3

<400> SEQUENCE: 282
agtgtatata gtcc                                                         14

<210> SEQ ID NO 283
<211> LENGTH: 13
<212> TYPE: DNA
<213> ORGANISM: Porcine Adenovirus 3

<400> SEQUENCE: 283
agtgtatata gtc                                                          13

<210> SEQ ID NO 284
<211> LENGTH: 12
<212> TYPE: DNA
<213> ORGANISM: Porcine Adenovirus 3

<400> SEQUENCE: 284
agtgtatata gt                                                           12

<210> SEQ ID NO 285
<211> LENGTH: 11
<212> TYPE: DNA
<213> ORGANISM: Porcine Adenovirus 3

<400> SEQUENCE: 285
agtgtatata g                                                            11

<210> SEQ ID NO 286
<211> LENGTH: 18
<212> TYPE: DNA
<213> ORGANISM: Porcine Adenovirus 3

<400> SEQUENCE: 286
cagtgtatat agtccgcg                                                     18
```

-continued

```
<210> SEQ ID NO 287
<211> LENGTH: 17
<212> TYPE: DNA
<213> ORGANISM: Porcine Adenovirus 3

<400> SEQUENCE: 287
cagtgtatat agtccgc                                                    17

<210> SEQ ID NO 288
<211> LENGTH: 16
<212> TYPE: DNA
<213> ORGANISM: Porcine Adenovirus 3

<400> SEQUENCE: 288
cagtgtatat agtccg                                                     16

<210> SEQ ID NO 289
<211> LENGTH: 15
<212> TYPE: DNA
<213> ORGANISM: Porcine Adenovirus 3

<400> SEQUENCE: 289
cagtgtatat agtcc                                                      15

<210> SEQ ID NO 290
<211> LENGTH: 14
<212> TYPE: DNA
<213> ORGANISM: Porcine Adenovirus 3

<400> SEQUENCE: 290
cagtgtatat agtc                                                       14

<210> SEQ ID NO 291
<211> LENGTH: 13
<212> TYPE: DNA
<213> ORGANISM: Porcine Adenovirus 3

<400> SEQUENCE: 291
cagtgtatat agt                                                        13

<210> SEQ ID NO 292
<211> LENGTH: 12
<212> TYPE: DNA
<213> ORGANISM: Porcine Adenovirus 3

<400> SEQUENCE: 292
cagtgtatat ag                                                         12

<210> SEQ ID NO 293
<211> LENGTH: 18
<212> TYPE: DNA
<213> ORGANISM: Porcine Adenovirus 3

<400> SEQUENCE: 293
cagtgtatat agtccgcg                                                   18

<210> SEQ ID NO 294
<211> LENGTH: 17
<212> TYPE: DNA
<213> ORGANISM: Porcine Adenovirus 3

<400> SEQUENCE: 294
cagtgtatat agtccgc                                                    17
```

```
<210> SEQ ID NO 295
<211> LENGTH: 16
<212> TYPE: DNA
<213> ORGANISM: Porcine Adenovirus 3

<400> SEQUENCE: 295
cagtgtatat agtccg                                                 16

<210> SEQ ID NO 296
<211> LENGTH: 15
<212> TYPE: DNA
<213> ORGANISM: Porcine Adenovirus 3

<400> SEQUENCE: 296
cagtgtatat agtcc                                                  15

<210> SEQ ID NO 297
<211> LENGTH: 14
<212> TYPE: DNA
<213> ORGANISM: Porcine Adenovirus 3

<400> SEQUENCE: 297
cagtgtatat agtc                                                   14

<210> SEQ ID NO 298
<211> LENGTH: 13
<212> TYPE: DNA
<213> ORGANISM: Porcine Adenovirus 3

<400> SEQUENCE: 298
cagtgtatat agt                                                    13

<210> SEQ ID NO 299
<211> LENGTH: 12
<212> TYPE: DNA
<213> ORGANISM: Porcine Adenovirus 3

<400> SEQUENCE: 299
cagtgtatat ag                                                     12

<210> SEQ ID NO 300
<211> LENGTH: 18
<212> TYPE: DNA
<213> ORGANISM: Porcine Adenovirus 3

<400> SEQUENCE: 300
cagtgtatat agtccgcg                                               18

<210> SEQ ID NO 301
<211> LENGTH: 17
<212> TYPE: DNA
<213> ORGANISM: Porcine Adenovirus 3

<400> SEQUENCE: 301
cagtgtatat agtccgc                                                17

<210> SEQ ID NO 302
<211> LENGTH: 16
<212> TYPE: DNA
<213> ORGANISM: Porcine Adenovirus 3

<400> SEQUENCE: 302
cagtgtatat agtccg                                                 16
```

-continued

<210> SEQ ID NO 303
<211> LENGTH: 15
<212> TYPE: DNA
<213> ORGANISM: Porcine Adenovirus 3

<400> SEQUENCE: 303
cagtgtatat agtcc                                                    15

<210> SEQ ID NO 304
<211> LENGTH: 14
<212> TYPE: DNA
<213> ORGANISM: Porcine Adenovirus 3

<400> SEQUENCE: 304
cagtgtatat agtc                                                     14

<210> SEQ ID NO 305
<211> LENGTH: 13
<212> TYPE: DNA
<213> ORGANISM: Porcine Adenovirus 3

<400> SEQUENCE: 305
cagtgtatat agt                                                      13

<210> SEQ ID NO 306
<211> LENGTH: 12
<212> TYPE: DNA
<213> ORGANISM: Porcine Adenovirus 3

<400> SEQUENCE: 306
cagtgtatat ag                                                       12

<210> SEQ ID NO 307
<211> LENGTH: 18
<212> TYPE: DNA
<213> ORGANISM: Porcine Adenovirus 3

<400> SEQUENCE: 307
cagtgtatat agtccgcg                                                 18

<210> SEQ ID NO 308
<211> LENGTH: 17
<212> TYPE: DNA
<213> ORGANISM: Porcine Adenovirus 3

<400> SEQUENCE: 308
cagtgtatat agtccgc                                                  17

<210> SEQ ID NO 309
<211> LENGTH: 16
<212> TYPE: DNA
<213> ORGANISM: Porcine Adenovirus 3

<400> SEQUENCE: 309
cagtgtatat agtccg                                                   16

<210> SEQ ID NO 310
<211> LENGTH: 15
<212> TYPE: DNA
<213> ORGANISM: Porcine Adenovirus 3

<400> SEQUENCE: 310

```
cagtgtatat agtcc                                                          15

<210> SEQ ID NO 311
<211> LENGTH: 15
<212> TYPE: DNA
<213> ORGANISM: Porcine Adenovirus 3

<400> SEQUENCE: 311
gagttttctc tcagc                                                          15

<210> SEQ ID NO 312
<211> LENGTH: 14
<212> TYPE: DNA
<213> ORGANISM: Porcine Adenovirus 3

<400> SEQUENCE: 312
gagttttctc tcag                                                           14

<210> SEQ ID NO 313
<211> LENGTH: 13
<212> TYPE: DNA
<213> ORGANISM: Porcine Adenovirus 3

<400> SEQUENCE: 313
gagttttctc tca                                                            13

<210> SEQ ID NO 314
<211> LENGTH: 12
<212> TYPE: DNA
<213> ORGANISM: Porcine Adenovirus 3

<400> SEQUENCE: 314
gagttttctc tc                                                             12

<210> SEQ ID NO 315
<211> LENGTH: 11
<212> TYPE: DNA
<213> ORGANISM: Porcine Adenovirus 3

<400> SEQUENCE: 315
gagttttctc t                                                              11

<210> SEQ ID NO 316
<211> LENGTH: 9
<212> TYPE: DNA
<213> ORGANISM: Porcine Adenovirus 3

<400> SEQUENCE: 316 gagttttct                                                                  9

<210> SEQ ID NO 317
<211> LENGTH: 8
<212> TYPE: DNA
<213> ORGANISM: Porcine Adenovirus 3

<400> SEQUENCE: 317 gagttttc                                                                   8

<210> SEQ ID NO 318
<211> LENGTH: 17
<212> TYPE: DNA
<213> ORGANISM: Porcine Adenovirus 3

<400> SEQUENCE: 318
```

```
agagttttct ctcagcg                                                    17

<210> SEQ ID NO 319
<211> LENGTH: 16
<212> TYPE: DNA
<213> ORGANISM: Porcine Adenovirus 3

<400> SEQUENCE: 319
agagttttct ctcagc                                                     16

<210> SEQ ID NO 320
<211> LENGTH: 15
<212> TYPE: DNA
<213> ORGANISM: Porcine Adenovirus 3

<400> SEQUENCE: 320
agagttttct ctcag                                                      15

<210> SEQ ID NO 321
<211> LENGTH: 13
<212> TYPE: DNA
<213> ORGANISM: Porcine Adenovirus 3

<400> SEQUENCE: 321
agagttttct ctc                                                        13

<210> SEQ ID NO 322
<211> LENGTH: 12
<212> TYPE: DNA
<213> ORGANISM: Porcine Adenovirus 3

<400> SEQUENCE: 322
agagttttct ct                                                         12

<210> SEQ ID NO 323
<211> LENGTH: 11
<212> TYPE: DNA
<213> ORGANISM: Porcine Adenovirus 3

<400> SEQUENCE: 323
agagttttct c                                                          11

<210> SEQ ID NO 324
<211> LENGTH: 10
<212> TYPE: DNA
<213> ORGANISM: Porcine Adenovirus 3

<400> SEQUENCE: 324
agagttttct                                                            10

<210> SEQ ID NO 325
<211> LENGTH: 9
<212> TYPE: DNA
<213> ORGANISM: Porcine Adenovirus 3

<400> SEQUENCE: 325 agagttttc                                                              9

<210> SEQ ID NO 326
<211> LENGTH: 17
<212> TYPE: DNA
<213> ORGANISM: Porcine Adenovirus 3
```

```
<400> SEQUENCE: 326
tagagttttc tctcagc                                                      17

<210> SEQ ID NO 327
<211> LENGTH: 16
<212> TYPE: DNA
<213> ORGANISM: Porcine Adenovirus 3

<400> SEQUENCE: 327
tagagttttc tctcag                                                       16

<210> SEQ ID NO 328
<211> LENGTH: 15
<212> TYPE: DNA
<213> ORGANISM: Porcine Adenovirus 3

<400> SEQUENCE: 328
tagagttttc tctca                                                        15

<210> SEQ ID NO 329
<211> LENGTH: 14
<212> TYPE: DNA
<213> ORGANISM: Porcine Adenovirus 3

<400> SEQUENCE: 329
tagagttttc tctc                                                         14

<210> SEQ ID NO 330
<211> LENGTH: 13
<212> TYPE: DNA
<213> ORGANISM: Porcine Adenovirus 3

<400> SEQUENCE: 330
tagagttttc tct                                                          13

<210> SEQ ID NO 331
<211> LENGTH: 12
<212> TYPE: DNA
<213> ORGANISM: Porcine Adenovirus 3

<400> SEQUENCE: 331
tagagttttc tc                                                           12

<210> SEQ ID NO 332
<211> LENGTH: 11
<212> TYPE: DNA
<213> ORGANISM: Porcine Adenovirus 3

<400> SEQUENCE: 332
tagagttttc t                                                            11

<210> SEQ ID NO 333
<211> LENGTH: 10
<212> TYPE: DNA
<213> ORGANISM: Porcine Adenovirus 3

<400> SEQUENCE: 333
tagagttttc                                                              10

<210> SEQ ID NO 334
<211> LENGTH: 8
<212> TYPE: DNA
<213> ORGANISM: Porcine Adenovirus 5
```

```
<400> SEQUENCE: 334 gtattttc                                                          8

<210> SEQ ID NO 335
<211> LENGTH: 9
<212> TYPE: DNA
<213> ORGANISM: Porcine Adenovirus 5

<400> SEQUENCE: 335 gtattttcc                                                         9

<210> SEQ ID NO 336
<211> LENGTH: 10
<212> TYPE: DNA
<213> ORGANISM: Porcine Adenovirus 5

<400> SEQUENCE: 336
gtattttcca                                                        10

<210> SEQ ID NO 337
<211> LENGTH: 11
<212> TYPE: DNA
<213> ORGANISM: Porcine Adenovirus 5

<400> SEQUENCE: 337
gtattttcca c                                                      11

<210> SEQ ID NO 338
<211> LENGTH: 9
<212> TYPE: DNA
<213> ORGANISM: Porcine Adenovirus 5

<400> SEQUENCE: 338 ggtattttc                                                         9

<210> SEQ ID NO 339
<211> LENGTH: 10
<212> TYPE: DNA
<213> ORGANISM: Porcine Adenovirus 5

<400> SEQUENCE: 339
ggtattttcc                                                        10

<210> SEQ ID NO 340
<211> LENGTH: 11
<212> TYPE: DNA
<213> ORGANISM: Porcine Adenovirus 5

<400> SEQUENCE: 340
ggtattttcc a                                                      11

<210> SEQ ID NO 341
<211> LENGTH: 12
<212> TYPE: DNA
<213> ORGANISM: Porcine Adenovirus 5

<400> SEQUENCE: 341
ggtattttcc ac                                                     12

<210> SEQ ID NO 342
<211> LENGTH: 10
<212> TYPE: DNA
```

```
<213> ORGANISM: Porcine Adenovirus 5

<400> SEQUENCE: 342
tggtattttc                                                              10

<210> SEQ ID NO 343
<211> LENGTH: 11
<212> TYPE: DNA
<213> ORGANISM: Porcine Adenovirus 5

<400> SEQUENCE: 343
tggtattttc c                                                            11

<210> SEQ ID NO 344
<211> LENGTH: 12
<212> TYPE: DNA
<213> ORGANISM: Porcine Adenovirus 5

<400> SEQUENCE: 344
tggtattttc ca                                                           12

<210> SEQ ID NO 345
<211> LENGTH: 13
<212> TYPE: DNA
<213> ORGANISM: Porcine Adenovirus 5

<400> SEQUENCE: 345
tggtattttc cac                                                          13

<210> SEQ ID NO 346
<211> LENGTH: 11
<212> TYPE: DNA
<213> ORGANISM: Porcine Adenovirus 5

<400> SEQUENCE: 346
ctggtatttt c                                                            11

<210> SEQ ID NO 347
<211> LENGTH: 12
<212> TYPE: DNA
<213> ORGANISM: Porcine Adenovirus 5

<400> SEQUENCE: 347
ctggtatttt cc                                                           12

<210> SEQ ID NO 348
<211> LENGTH: 13
<212> TYPE: DNA
<213> ORGANISM: Porcine Adenovirus 5

<400> SEQUENCE: 348
ctggtatttt cca                                                          13

<210> SEQ ID NO 349
<211> LENGTH: 7
<212> TYPE: DNA
<213> ORGANISM: Porcine Adenovirus 5

<400> SEQUENCE: 349 gatattg                                                                 7

<210> SEQ ID NO 350
<211> LENGTH: 8
```

-continued

```
<212> TYPE: DNA
<213> ORGANISM: Porcine Adenovirus 5

<400> SEQUENCE: 350 gatattgg                                                                    8

<210> SEQ ID NO 351
<211> LENGTH: 8
<212> TYPE: DNA
<213> ORGANISM: Porcine Adenovirus 5

<400> SEQUENCE: 351 tgatattg                                                                    8

<210> SEQ ID NO 352
<211> LENGTH: 9
<212> TYPE: DNA
<213> ORGANISM: Porcine Adenovirus 5

<400> SEQUENCE: 352 tgatattgg                                                                   9

<210> SEQ ID NO 353
<211> LENGTH: 9
<212> TYPE: DNA
<213> ORGANISM: Porcine Adenovirus 5

<400> SEQUENCE: 353 gtgatattg                                                                   9

<210> SEQ ID NO 354
<211> LENGTH: 6
<212> TYPE: DNA
<213> ORGANISM: Porcine Adenovirus 5

<400> SEQUENCE: 354 ctttac                                                                      6

<210> SEQ ID NO 355
<211> LENGTH: 7
<212> TYPE: DNA
<213> ORGANISM: Porcine Adenovirus 5

<400> SEQUENCE: 355 ctttacc                                                                     7

<210> SEQ ID NO 356
<211> LENGTH: 8
<212> TYPE: DNA
<213> ORGANISM: Porcine Adenovirus 5

<400> SEQUENCE: 356 ctttacct                                                                    8

<210> SEQ ID NO 357
<211> LENGTH: 9
<212> TYPE: DNA
<213> ORGANISM: Porcine Adenovirus 5

<400> SEQUENCE: 357 ctttacctg                                                                   9

<210> SEQ ID NO 358
```

```
<211> LENGTH: 10
<212> TYPE: DNA
<213> ORGANISM: Porcine Adenovirus 5

<400> SEQUENCE: 358
ctttacctgg                                                          10

<210> SEQ ID NO 359
<211> LENGTH: 11
<212> TYPE: DNA
<213> ORGANISM: Porcine Adenovirus 5

<400> SEQUENCE: 359
ctttacctgg g                                                        11

<210> SEQ ID NO 360
<211> LENGTH: 7
<212> TYPE: DNA
<213> ORGANISM: Porcine Adenovirus 5

<400> SEQUENCE: 360 cctttac                                                              7

<210> SEQ ID NO 361
<211> LENGTH: 8
<212> TYPE: DNA
<213> ORGANISM: Porcine Adenovirus 5

<400> SEQUENCE: 361 cctttacc                                                             8

<210> SEQ ID NO 362
<211> LENGTH: 9
<212> TYPE: DNA
<213> ORGANISM: Porcine Adenovirus 5

<400> SEQUENCE: 362 cctttacct                                                            9

<210> SEQ ID NO 363
<211> LENGTH: 10
<212> TYPE: DNA
<213> ORGANISM: Porcine Adenovirus 5

<400> SEQUENCE: 363
cctttacctg                                                          10

<210> SEQ ID NO 364
<211> LENGTH: 11
<212> TYPE: DNA
<213> ORGANISM: Porcine Adenovirus 5

<400> SEQUENCE: 364
cctttacctg g                                                        11

<210> SEQ ID NO 365
<211> LENGTH: 9
<212> TYPE: DNA
<213> ORGANISM: Porcine Adenovirus 5

<400> SEQUENCE: 365 caattttac                                                            9
```

```
<210> SEQ ID NO 366
<211> LENGTH: 10
<212> TYPE: DNA
<213> ORGANISM: Porcine Adenovirus 5

<400> SEQUENCE: 366
caattttacc                                                          10

<210> SEQ ID NO 367
<211> LENGTH: 11
<212> TYPE: DNA
<213> ORGANISM: Porcine Adenovirus 5

<400> SEQUENCE: 367
caattttacc a                                                        11

<210> SEQ ID NO 368
<211> LENGTH: 12
<212> TYPE: DNA
<213> ORGANISM: Porcine Adenovirus 5

<400> SEQUENCE: 368
caattttacc ac                                                       12

<210> SEQ ID NO 369
<211> LENGTH: 10
<212> TYPE: DNA
<213> ORGANISM: Porcine Adenovirus 5

<400> SEQUENCE: 369
tcaattttac                                                          10

<210> SEQ ID NO 370
<211> LENGTH: 11
<212> TYPE: DNA
<213> ORGANISM: Porcine Adenovirus 5

<400> SEQUENCE: 370
tcaattttac c                                                        11

<210> SEQ ID NO 371
<211> LENGTH: 12
<212> TYPE: DNA
<213> ORGANISM: Porcine Adenovirus 5

<400> SEQUENCE: 371
tcaattttac ca                                                       12

<210> SEQ ID NO 372
<211> LENGTH: 13
<212> TYPE: DNA
<213> ORGANISM: Porcine Adenovirus 5

<400> SEQUENCE: 372
tcaattttac cac                                                      13

<210> SEQ ID NO 373
<211> LENGTH: 11
<212> TYPE: DNA
<213> ORGANISM: Porcine Adenovirus 5

<400> SEQUENCE: 373
ctcaatttta c                                                        11
```

```
<210> SEQ ID NO 374
<211> LENGTH: 12
<212> TYPE: DNA
<213> ORGANISM: Porcine Adenovirus 5

<400> SEQUENCE: 374
ctcaatttta cc                                                        12

<210> SEQ ID NO 375
<211> LENGTH: 13
<212> TYPE: DNA
<213> ORGANISM: Porcine Adenovirus 5

<400> SEQUENCE: 375
ctcaatttta cca                                                       13

<210> SEQ ID NO 376
<211> LENGTH: 8
<212> TYPE: DNA
<213> ORGANISM: Porcine Adenovirus 5

<400> SEQUENCE: 376 gatttttc                                                              8

<210> SEQ ID NO 377
<211> LENGTH: 9
<212> TYPE: DNA
<213> ORGANISM: Porcine Adenovirus 5

<400> SEQUENCE: 377 gatttttcc                                                             9

<210> SEQ ID NO 378
<211> LENGTH: 10
<212> TYPE: DNA
<213> ORGANISM: Porcine Adenovirus 5

<400> SEQUENCE: 378
gatttttcca                                                           10

<210> SEQ ID NO 379
<211> LENGTH: 11
<212> TYPE: DNA
<213> ORGANISM: Porcine Adenovirus 5

<400> SEQUENCE: 379
gatttttcca c                                                         11

<210> SEQ ID NO 380
<211> LENGTH: 9
<212> TYPE: DNA
<213> ORGANISM: Porcine Adenovirus 5

<400> SEQUENCE: 380 cgatttttc                                                             9

<210> SEQ ID NO 381
<211> LENGTH: 10
<212> TYPE: DNA
<213> ORGANISM: Porcine Adenovirus 5

<400> SEQUENCE: 381
cgatttttcc                                                           10
```

```
<210> SEQ ID NO 382
<211> LENGTH: 11
<212> TYPE: DNA
<213> ORGANISM: Porcine Adenovirus 5

<400> SEQUENCE: 382 cgattttt cc a                                                         11

<210> SEQ ID NO 383
<211> LENGTH: 12
<212> TYPE: DNA
<213> ORGANISM: Porcine Adenovirus 5

<400> SEQUENCE: 383
cgatttttcc ac                                                         12

<210> SEQ ID NO 384
<211> LENGTH: 10
<212> TYPE: DNA
<213> ORGANISM: Porcine Adenovirus 5

<400> SEQUENCE: 384 tcgattttttc                                                           10

<210> SEQ ID NO 385
<211> LENGTH: 11
<212> TYPE: DNA
<213> ORGANISM: Porcine Adenovirus 5

<400> SEQUENCE: 385
tcgatttttc c                                                          11

<210> SEQ ID NO 386
<211> LENGTH: 12
<212> TYPE: DNA
<213> ORGANISM: Porcine Adenovirus 5

<400> SEQUENCE: 386
tcgatttttc ca                                                         12

<210> SEQ ID NO 387
<211> LENGTH: 13
<212> TYPE: DNA
<213> ORGANISM: Porcine Adenovirus 5

<400> SEQUENCE: 387
tcgatttttc cac                                                        13

<210> SEQ ID NO 388
<211> LENGTH: 11
<212> TYPE: DNA
<213> ORGANISM: Porcine Adenovirus 5

<400> SEQUENCE: 388 gtcgatttt t c                                                         11

<210> SEQ ID NO 389
<211> LENGTH: 12
<212> TYPE: DNA
<213> ORGANISM: Porcine Adenovirus 5

<400> SEQUENCE: 389
```

```
gtcgattttt cc                                                      12

<210> SEQ ID NO 390
<211> LENGTH: 13
<212> TYPE: DNA
<213> ORGANISM: Porcine Adenovirus 5

<400> SEQUENCE: 390
gtcgattttt cca                                                     13

<210> SEQ ID NO 391
<211> LENGTH: 14
<212> TYPE: DNA
<213> ORGANISM: Porcine Adenovirus 5

<400> SEQUENCE: 391
gtcgattttt ccac                                                    14

<210> SEQ ID NO 392
<211> LENGTH: 12
<212> TYPE: DNA
<213> ORGANISM: Porcine Adenovirus 5

<400> SEQUENCE: 392
ggtcgatttt tc                                                      12

<210> SEQ ID NO 393
<211> LENGTH: 13
<212> TYPE: DNA
<213> ORGANISM: Porcine Adenovirus 5

<400> SEQUENCE: 393
ggtcgatttt tcc                                                     13

<210> SEQ ID NO 394
<211> LENGTH: 14
<212> TYPE: DNA
<213> ORGANISM: Porcine Adenovirus 5

<400> SEQUENCE: 394
ggtcgatttt tcca                                                    14

<210> SEQ ID NO 395
<211> LENGTH: 10
<212> TYPE: DNA
<213> ORGANISM: Porcine Adenovirus 5

<400> SEQUENCE: 395
ctatttattc                                                         10

<210> SEQ ID NO 396
<211> LENGTH: 11
<212> TYPE: DNA
<213> ORGANISM: Porcine Adenovirus 5

<400> SEQUENCE: 396
ctatttattc t                                                       11

<210> SEQ ID NO 397
<211> LENGTH: 12
<212> TYPE: DNA
<213> ORGANISM: Porcine Adenovirus 5

<400> SEQUENCE: 397
```

-continued

```
ctatttattc tg                                              12

<210> SEQ ID NO 398
<211> LENGTH: 13
<212> TYPE: DNA
<213> ORGANISM: Porcine Adenovirus 5

<400> SEQUENCE: 398
ctatttattc tgc                                             13

<210> SEQ ID NO 399
<211> LENGTH: 14
<212> TYPE: DNA
<213> ORGANISM: Porcine Adenovirus 5

<400> SEQUENCE: 399
ctatttattc tgcg                                            14

<210> SEQ ID NO 400
<211> LENGTH: 15
<212> TYPE: DNA
<213> ORGANISM: Porcine Adenovirus 5

<400> SEQUENCE: 400
ctatttattc tgcgc                                           15

<210> SEQ ID NO 401
<211> LENGTH: 16
<212> TYPE: DNA
<213> ORGANISM: Porcine Adenovirus 5

<400> SEQUENCE: 401
ctatttattc tgcgcg                                          16

<210> SEQ ID NO 402
<211> LENGTH: 11
<212> TYPE: DNA
<213> ORGANISM: Porcine Adenovirus 5

<400> SEQUENCE: 402
cctatttatt c                                               11

<210> SEQ ID NO 403
<211> LENGTH: 12
<212> TYPE: DNA
<213> ORGANISM: Porcine Adenovirus 5

<400> SEQUENCE: 403
cctatttatt ct                                              12

<210> SEQ ID NO 404
<211> LENGTH: 13
<212> TYPE: DNA
<213> ORGANISM: Porcine Adenovirus 5

<400> SEQUENCE: 404
cctatttatt ctg                                             13

<210> SEQ ID NO 405
<211> LENGTH: 14
<212> TYPE: DNA
<213> ORGANISM: Porcine Adenovirus 5
```

-continued

<400> SEQUENCE: 405
cctatttatt ctgc                                                14

<210> SEQ ID NO 406
<211> LENGTH: 15
<212> TYPE: DNA
<213> ORGANISM: Porcine Adenovirus 5

<400> SEQUENCE: 406
cctatttatt ctgcg                                               15

<210> SEQ ID NO 407
<211> LENGTH: 16
<212> TYPE: DNA
<213> ORGANISM: Porcine Adenovirus 5

<400> SEQUENCE: 407
cctatttatt ctgcgc                                              16

<210> SEQ ID NO 408
<211> LENGTH: 12
<212> TYPE: DNA
<213> ORGANISM: Porcine Adenovirus 5

<400> SEQUENCE: 408
ccctatttat tc                                                  12

<210> SEQ ID NO 409
<211> LENGTH: 13
<212> TYPE: DNA
<213> ORGANISM: Porcine Adenovirus 5

<400> SEQUENCE: 409
ccctatttat tct                                                 13

<210> SEQ ID NO 410
<211> LENGTH: 14
<212> TYPE: DNA
<213> ORGANISM: Porcine Adenovirus 5

<400> SEQUENCE: 410
ccctatttat tctg                                                14

<210> SEQ ID NO 411
<211> LENGTH: 15
<212> TYPE: DNA
<213> ORGANISM: Porcine Adenovirus 5

<400> SEQUENCE: 411
ccctatttat tctgc                                               15

<210> SEQ ID NO 412
<211> LENGTH: 16
<212> TYPE: DNA
<213> ORGANISM: Porcine Adenovirus 5

<400> SEQUENCE: 412
ccctatttat tctgcg                                              16

<210> SEQ ID NO 413
<211> LENGTH: 17
<212> TYPE: DNA
<213> ORGANISM: Porcine Adenovirus 5

```
<400> SEQUENCE: 413
ccctatttat tctgcgc                                                    17

<210> SEQ ID NO 414
<211> LENGTH: 320
<212> TYPE: DNA
<213> ORGANISM: Porcine Adenovirus 3

<400> SEQUENCE: 414
cggggcgggg ccgagcggcg gaaattcccg cacaggtgga gagtaccgcg ggattttgtg     60
ccctctggac cggaccttcg ccctccggtg tggcacttcc gcaccacacg tccgcggccc    120
ggtattcccc acctgacgac ggtgacacca ctcacctgag cggggtgtcc ttcgcgctga    180
gaggtccgcg gcggccgccc gagatgacgt gtgtgggtgt attttttccc ctcagtgtat    240
atagtccgcg cagcgcccga gagtcactac tcttgagtcc gaagggagta gagttttctc    300
tcagcggaac agaccctcga                                                320
```

PAV REGIONS FOR ENCAPSIDATION AND E1 TRANSCRIPTIONAL CONTROL

CROSS REFERENCE TO RELATED APPLICATION

This application claims benefit of U.S. Provisional Patent Application Ser. No. 60/397,251, filed Jul. 19, 2002, and U.S. Provisional Patent Application Ser. No. 60/460,798, filed Apr. 4, 2003, all of which are incorporated by reference herein in their entirety.

FIELD OF THE INVENTION

The present invention is in the field of recombinant adenovirus vectors. More particularly, it concerns recombinant adenovirus vectors which comprise a porcine adenoviral region(s) essential for viral encapsidation, methods of making adenovirus vectors which comprise a porcine adenoviral region(s) essential for viral encapsidation and uses of adenovirus vectors which comprise a porcine adenoviral region(s) essential for viral encapsidation, in particular for vaccine purposes, gene delivery, and expression systems. The present invention also relates to the identification of porcine adenovirus E1 transcriptional control regions and provides porcine adenovirus vectors comprising modification(s) in part or all of one or more E1 transcriptional control regions, methods of making such porcine adenovirus vectors, and uses of such porcine adenovirus vectors.

BACKGROUND OF THE INVENTION

Adenoviruses are double-stranded DNA viruses that have been isolated from a wide variety of avian and mammalian species, including human, swine, cow and sheep. The adenoviruses cause enteric or respiratory infection in humans as well as in domestic and laboratory animals.

At least 47 serotypes of human adenoviruses have been described. Reviews of the most common serotypes associated with particular diseases have been published. See for example, Foy H. M. (1989) *Adenoviruses* In Evans, AS (ed). *Viral Infections of Humans*. New York, Plenum Publishing, pp 77-89 and Rubin B. A. (1993) *Clinical picture and epidemiology of adenovirus infections, Acta Microbiol. Hung* 40:303-323. The complete genome sequence of human adenovirus 5 is disclosed in GenBank accession number M73260. The complete genome sequence of human adenovirus 2 is disclosed in GenBank accession number J01917.

Porcine adenovirus (PAV) infection has been associated with encephalitis, pneumonia, kidney lesions and diarrhea. See Derbyshire (1992) In: *Diseases of Swine* (ed. Leman et al.), 7th edition, Iowa State University Press, Ames, Iowa. pp. 225-227. It has been shown that PAV is capable of stimulating both humoral response and mucosal antibody responses in the intestine of infected piglets. Tuboly et al. (1993) *Res. in Vet. Sci.* 54:345-350. Cross-neutralization studies have indicated the existence of at least five serotypes of PAV. See Derbyshire et al. (1975) *J. Comp. Pathol.* 85:437-443; and Hirahara et al. (1990) *Jpn. J. Vet. Sci.* 52:407-409. Previous studies of the PAV genome have included the determination of restriction maps for PAV Type 3 (PAV-3) and cloning of restriction fragments representing the complete genome of PAV-3. See Reddy et al. (1993) *Intervirology* 36:161-168. In addition, restriction maps for PAV-1 and PAV-2 have been determined. See Reddy et al. (1995b) *Arch. Virol.* 140:195-200.

Nucleotide sequences have been determined for segments of the genome of various PAV serotypes. Sequences of the E3, pVIII and fiber genes of PAV-3 were determined by Reddy et al. (1995) *Virus Res.* 36:97-106. The E3, pVIII and fiber genes of PAV-1 and PAV-2 were sequenced by Reddy et al. (1996) *Virus Res.* 43:99-109, while the PAV-4 E3, pVIII and fiber gene sequences were determined by Kleiboeker (1994) *Virus Res.* 31:17-25. The PAV-4 fiber gene sequence was determined by Kleiboeker (1995) *Virus Res.* 39:299-309. Inverted terminal repeat (ITR) sequences for all five PAV serotypes (PAV-1 through PAV-5) were determined by Reddy et al. (1995) *Virology* 212:237-239. The PAV-3 penton sequence was determined by McCoy et al. (1996) *Arch. Virol.* 141: 1367-1375. The nucleotide sequence of the E1 region of PAV-4 was determined by Kleiboeker (1995) *Virus Res.* 36:259-268. The sequence of the protease (23K) gene of PAV-3 was determined by McCoy et al. (1996) *DNA Seq.* 6:251-254. The sequence of the PAV-3 hexon gene (and the 14 N-terminal codons of the 23K protease gene) has been deposited in the GenBank database under accession No. U34592. The sequence of the PAV-3 100K gene has been deposited in the GenBank database under accession No. U82628. The sequence of the PAV-3 E4 region has been determined by Reddy et al. (1997) *Virus Genes* 15:87-90. The transcriptional map and complete DNA sequence of PAV-3 genome was reported (Reddy et al., 1998, *Virus Res.*58::97-106 and Reddy et al., 1998, *Virology* 251:414-426). Vrati et al. (1995, *Virology*, 209:400-408) disclose sequences for ovine adenovirus. U.S. Pat. No. 6,492,343 discloses PAV expression and vaccine systems.

BAV3 was first isolated in 1965 and is the best characterized of the BAV genotypes, containing a genome of approximately 35 kb (Kurokawa et al (1978) *J. Virol.* 28:212-218). Reddy et al. (1998, *Journal of Virology*, 72:1394) disclose nucleotide sequence, genome organization, and transcription map of BAV3. Reddy et al. (1999, *Journal of Virology*, 73: 9137) disclose a replication-defective BAV3 as an expression vector. BAV3, a representative of subgroup 1 of BAVs (Bartha (1969) *Acta Vet. Acad. Sci. Hung.* 19:319-321), is a common pathogen of cattle usually resulting in subclinical infection (Darbyshire et al. (1965). *J. Comp. Pathol.* 75:327-330), though occasionally associated with a more serious respiratory tract infection (Darbyshire et al., 1966 *Res. Vet. Sci.* 7:81-93; Mattson et al., 1988 *J. Vet Res* 49:67-69). Like other adenoviruses, BAV3 is a non-enveloped icosahedral particle of 75 nm in diameter (Niiyama et al. (1975) *J. Virol.* 16:621-633) containing a linear double-stranded DNA molecule. BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465-473; Motoi et al., 1972 *Gann* 63:415-418). Cross hybridization was observed between BAV3 and human adenovirus type 2 (HAd2) (Hu et al., 1984 *J. Virol.* 49:604-608) in most regions of the genome including some regions near but not at the left end of the genome. Bovine adenovirus expression and vaccine systems are disclosed in for example, U.S. Pat. Nos. 5,820,868 and 6,001,591.

For general background references regarding adenovirus and development of adenoviral vector systems, see Graham et al. (1973) *Virology* 52:456-467; Takiff et al. (1981) *Lancet* 11:832-834; Berkner et al. (1983) *Nucleic Acid Research* 11: 6003-6020; Graham (1984) *EMBO J.* 3:2917-2922; Bett et al. (1993) *J. Virology* 67:5911-5921; and Bett et al. (1994) *Proc. Natl. Acad. Sci. USA* 91:8802-8806.

For a review of adenoviruses and adenovirus replication, see Shenk, T. and Horwitz, M. S., *Virology*, third edition, Fields, B. N. et al., eds., Raven Press Limited, New York (1996), Chapters 67 and 68, respectively.

Adenoviral vectors are divided into helper-independent and helper-dependent groups based on the region of the adenoviral genome used for the insertion of transgenes. Helper-dependent vectors are usually made by deletion of E1 sequences and substitution of foreign DNA, and are produced in complementing human cell lines that constitutively express E1 proteins. Graham et al. (1977) *J. Gen. Virol.* 36:59-74; Fallaux et al. (1996) *Hum. Gene Ther.* 7:215-222; Fallaux et al. (1998) *Hum. Gene Ther.* 9:1909-1917. An adenovirus E1A region is described in Darbyshire (1966, *Nature* 211:102) and Whyte et al., 1988, *J. Virol.* 62:257-265.

Though E1-deleted viruses do not replicate in cells that do not express E1 proteins, the viruses can express foreign proteins in these cells, provided the genes are placed under the control of a constitutive promoter. Xiang et al. (1996) *Virology* 219:220-227. Vaccination of animals with adenovirus recombinants containing inserts in the E1 region induced a systemic immune response and provided protection against subsequent challenge. Imler et al (1995) *Hum. Gene Ther.* 6:711-721; Imler et al. (1996) *Gene Therap* 3:75-84. This type of expression vector provides a significant safety profile to the vaccine as it eliminates the potential for dissemination of the vector within the vaccine and therefore, the spread of the vector to non-vaccinated contacts or to the general environment. However, the currently used human adenovirus (HAV) based vectors are endemic in most populations, which provides an opportunity for recombination between the helper-dependent viral vectors and wild type viruses.

United States Patent Application Publication 20020019051 discloses chimeric adenoviral vectors. Morsy et al. (1998, *P.N.A.S. USA* 95:7866-7871); Kochanek et al. (1996 *P.N.A.S. USA* 93:5731-5736); Clemens et al. (1998, *Gene Therapy* 3:965-972); and Parks et al.(1996, *P.N.A.S. USA* 93:13565-13570) disclose adenovirus vectors.

There remains a need for improved adenoviral vectors, especially adenoviral vectors for expression of transgenes in mammalian cells, and for the development of effective recombinant adenovirus vectors for use in immunization and expression systems.

All references and patent publications disclosed herein are hereby incorporated herein in their entirety by reference.

BRIEF SUMMARY OF THE INVENTION

The present invention relates, in part, to the identification of porcine adenovirus sequences essential for encapsidation. Accordingly, the present invention provides isolated porcine adenovirus sequences essential for encapsidation that comprise a nucleotide sequence selected from the group consisting of AAATT; ATTTT; TATT; TATTTTTT; TATATA; TTTT; TATTTT; ATATT; TTTA; AATTTTA; ATTTTT; and TATTTATT.

The present invention also provides isolated porcine adenovirus sequences essential for encapsidation that comprise a nucleotide sequence selected from the group consisting of:

Motif I represented by $X_I$AAATTY$_I$, wherein $X_1$ is selected from the group consisting of G, GG, CGG, GCGG, and GGCGG, and wherein Y$_I$ is selected from the group consisting of CCCGCACA, CCCGCAC, CCCGCA, CCCGC, CCCG, CCC, CC and C (SEQ ID NOS: 1, 2, 91, 103-139);

Motif II represented by $X_{II}$ATTTTY$_{II}$, wherein $X_{II}$ is selected from the group consisting of G, GG, GGG, CGGG, and GCGGG, and wherein Y$_{II}$ is selected from the group consisting of GTGCCCTCT, GTGCCCTC, GTGCCCT, GTGCCC, GTGCC, GTGC, GTG, GT and G (SEQ ID NOS: 3, 4, 95, 140-181);

Motif III represented by $X_{III}$TATTY$_{III}$, wherein $X_{III}$ is selected from the group consisting of G, GG, CGG, CCGG, and CCCGG, and wherein Y$_{III}$ is selected from the group consisting of CCCCACCTG, CCCCACCT, CCCCACC, CCCCAC, CCCCA, CCCC, CCC, CC, and C (SEQ ID NOS: 5, 6, 97, 182-223);

Motif IV represented by $X_{IV}$TATTTTTTY$_{IV}$, wherein $X_{IV}$ is selected from the group consisting of G, TG, GTG, GGTG, and GGGTG, and wherein Y$_{IV}$ is selected from the group consisting of CCCCTCA, CCCCTC, CCCCT, CCCC, CCC, CC, and C SEQ ID NOS: 7, 8, 100, 224-255);

Motif V represented by $X_V$TATATAY$_V$, wherein $X_V$ is selected from the group consisting of G, TG, GTG, AGTG, and CAGTG, and wherein Y$_V$ is selected from the group consisting of GTCCGCGC, GTCCGCG, GTCCGC, GTCCG, GTCC, GTC, GT and G (SEQ ID NOS: 9, 10, 101, 256-292); and Motif VI represented by $X_{VI}$TTTTY$_{VI}$, wherein $X_{VI}$ is selected from the group consisting of G, AG, GAG, AGAG, and TAGAG, Wherein Y$_{VI}$ is selected from the group consisting of CTCTCAGCG, CTCTCAGC, CTCTCAG, CTCTCA, CTCTC, CTCT, CTC, CT and C (SEQ ID NOS: 11, 12, 99, 102, 293-333).

The present invention further provides isolated porcine adenovirus sequences essential for encapsidation that comprise a nucleotide sequence selected from the group consisting of:

Motif 1 represented by $X_1$TATTTTY$_1$, wherein $X_1$ is selected from the group consisting of G, GG, TGG, and CTGG, and wherein Y$_1$ is selected from the group consisting of C, CC, CCA, and CCAC (SEQ ID NOS: 13, 334-348);

Motif 2 represented by $X_2$ATATTY$_2$, wherein $X_2$ is selected from the group consisting of G, TG, and GTG, and wherein Y$_2$ is selected from the group consisting of G and GG (SEQ ID NOS: 14, 349-353);

Motif 3 represented by $X_3$TTTAY$_3$, wherein $X_3$ is selected from the group consisting of C and CC, and wherein Y$_3$ is selected from the group consisting of C, CC, CCT, CCTG, CCTGG, and CCTGGG (SEQ ID NOS: 15, 354-364);

Motif 4 represented by $X_4$AATTTTAY$_4$, wherein $X_4$ is selected from the group consisting of C, TC, and CTC, and wherein Y$_4$ is selected from the group consisting of C, CC, CCA, and CCAC (SEQ ID NOS: 16, 365-375);

Motif 5 represented by $X_5$ATTTTTY$_5$, wherein $X_5$ is selected from the group consisting of G, CG, TCG, GTCG, and GGTCG, and wherein Y$_5$ is selected from the group consisting of C, CC, CCA, and CCAC (SEQ ID NOS: 17, 376-394); and Motif 6 represented by $X_6$TATTTATTY$_6$, wherein $X_6$ is selected from the group consisting of C, CC, and CCC, and wherein Y$_6$ is selected from the group consisting of C, CT, CTG, CTGC, CTGCG, CTGCGC, and CTGCGCG (SEQ ID NOS: 18, 20, 395-413).

In some examples, the porcine adenovirus sequence essential for encapsidation is a porcine adenovirus 3 sequence. In some examples, the porcine adenovirus sequence essential for encapsidation of porcine adenovirus type-3 is located between about nucleotide position 212 and about nucleotide position 531 (SEQ ID NO:414) at the left end of the genome. In other examples, the porcine adenovirus sequence essential for encapsidation is a porcine adenovirus 5 sequence. In other examples, an isolated porcine adenovirus sequence essential for encapsidation comprises a nucleotide sequence selected from the group consisting of:

CGGAAATTCCCGCACA;

GGCGGAAATTCCCGCACA;

GGGATTTTGTGCCCTCT;

GCGGGATTTTGTGCCCTCT

CGGTATTCCCCACCTG;

CCCGGTATTCCCCACCTG

GTGTATTTTTCCCCTCA;

GGGTGTATTTTTCCCCTCA

GTGTATATAGTCCGCGC;

CAGTGTATATAGTCCGCGC;

GAGTTTTCTCTCAGCG;

and

TAGAGTTTTCTCTCAGCG.

In other examples, an isolated porcine adenovirus sequence essential for encapsidation comprises a nucleotide sequence selected from the group consisting of:

CTGGTATTTTCCAC;
(SEQ ID NO: 13)

GTGATATTGG;
(SEQ ID NO: 14)

CCTTTACCTGGG;
(SEQ ID NO: 15)

CTCAATTTTACCAC;
(SEQ ID NO: 16)

GGTCGATTTTCCAC;
(SEQ ID NO: 17)

and

CCTATTTATTCTGCGCG.
(SEQ ID NO: 18)

In some examples a vector comprises at least one isolated porcine adenovirus sequence(s) essential for encapsidation. In other examples, a vector comprises at least 2, at least 3, at least 4, at least 5 or at least 6 isolated porcine adenovirus sequences essential for encapsidation. In some examples, a vector, comprises at least 2 porcine adenovirus sequences essential for encapsidation, wherein the at least 2 porcine adenovirus sequences essential for encapsidation are selected from the group consisting of Motif I, Motif II, Motif III, Motif IV, Motif V and Motif VI. In other examples, a vector comprises at least 2 porcine adenovirus sequences essential for encapsidation, wherein the at least 2 porcine adenovirus sequences essential for encapsidation are selected from the group consisting of Motif 1, Motif 2, Motif 3, Motif 4, Motif 5 and Motif 6. In some examples, a vector is an adenovirus vector. In some examples, the porcine adenovirus sequence(s) essential for encapsidation is heterologous to said vector. In some examples, the vector is a mammalian, non-porcine adenovirus vector. In some examples, adenovirus vectors comprise human adenoviral sequences. In other examples, recombinant adenovirus vectors comprise bovine adenoviral sequences. In other examples, recombinant adenovirus vectors further comprises at least one nucleic acid sequence encoding a transgene. In other examples, recombinant adenovirus vectors further comprises at least one inverted terminal repeat (ITR) sequence. In some examples, the ITR sequence is from a human adenovirus. In other examples, the ITR sequence is from a bovine adenovirus. In some examples, the present invention provides porcine adenovirus vectors deleted in a porcine adenovirus sequence(s) essential for encapsidation, wherein said adenovirus vector is optionally deleted in nucleic acid encoding adenoviral proteins necessary for replication.

The present invention also provides recombinant vectors, including adenovirus vectors, which comprise one or more porcine adenovirus sequence(s) essential for encapsidation, at least one inverted terminal repeat sequence, and nucleic acid encoding a transgene. In some examples wherein said vector is an adenovirus vector, the adenovirus vector is deleted in nucleic acid sequences encoding an adenoviral protein essential for replication. In some examples, the adenovirus vector is deleted in part or all of one or more or multiple nucleic acid sequence(s) encoding adenoviral proteins essential for replication. In some examples, the adenovirus vectors comprise human adenovirus sequences. In other examples, the adenovirus vectors comprise porcine adenovirus sequences and in yet other examples, the adenovirus vectors comprise bovine adenovirus sequences. In some examples, recombinant adenovirus vectors comprise nucleic acid sequences that encode an immunogenic polypeptide. In other examples, recombinant adenovirus vectors comprise nucleic acid sequences that encode an antigen of a pathogen, including a human antigen, porcine antigen, bovine antigen, canine antigen, feline antigen or equine antigen.

The present invention also provides isolated porcine E1 transcriptional control regions. In some examples, the E1 transcriptional control region is from about nucleotide 252 to about nucleotide 313 of the PAV3 sequence disclosed in Reddy et al. 1998, *Virology* 251:414-426. In some examples, the E1 transcriptional control region is from about nucleotide 382 to about nucleotide 433 of the PAV3 sequence disclosed in Reddy et al. 1998, *Virology* 251:414-426. In other examples, the E1 transcriptional control region is from about nucleotide 432 to about nucleotide 449 of the PAV3 sequence disclosed in Reddy et al. 1998, *Virology* 251:414-426. In yet other examples, the E1 transcriptional control region is from about nucleotide 312 to about nucleotide 382 of the PAV3 sequence disclosed in Reddy et al. 1998, *Virology* 251:414-426. In yet other examples, the E1 transcriptional control region is from about nucleotide 312 to about nucleotide 449 of the PAV3 sequence disclosed in Reddy et al. 1998, *Virology* 251:414-426. In yet other examples, the E1 transcriptional control region is from about nucleotide 252 to about nucleotide 449 of the PAV3 sequence disclosed in Reddy et al. 1998, *Virology* 251:414-426. In further examples, the E1 transcriptional control region is from about nucleotide 371 to about nucleotide 432 of the PAV3 sequence disclosed in Reddy et al. 1998, *Virology* 251:414-426. The present invention provides vectors, including adenovirus vectors, comprising an isolated porcine E1 transcriptional control region, as well as host cells and compositions comprising an isolated porcine E1 transcriptional control region The present invention provides recombinant porcine adenovirus vectors comprising a deletion in part or all of one or more E1 transcriptional control regions, including a deletion of nucleotides from about 252 to about 313, and/or a deletion of nucleotides from about 382 to about 433 and/or a deletion of nucleotides from about 432 to about 449, and/or a deletion of nucleotides from about 312 to about 382, and/or a deletion of nucleotides from about 312 to about 449, and/or a deletion of nucleotides from about 252 to about 449 and/or a deletion of nucleotides from about 371 to about 432 of the PAV3 sequence disclosed in Reddy et al. 1998, Virology 251:414-426. PAV3 nucleotides 371 to 490 are also shown herein in FIG. 13B.

The present invention also provides recombinant porcine adenovirus vectors comprising part or all of one or more additional E1 transcriptional control regions, including one or more additional region(s) of nucleotides from about 252 to about 313; and/or one or more additional region(s) of nucleotides from about 382 to about 433, and/or one or more additional regions of nucleotides from about 432 to about 449, and/or one or more additional regions of nucleotides from about 312 to about 382, and/or one or more additional regions of nucleotides from about 371 to about 432, and/or one or more additional region(s) of nucleotides from about 312 to about 449, and/or one or more additional regions of nucleotides from about 252 to about 449, of the PAV3 sequence disclosed in Reddy et al. 1998, Virology 251:414-426.

In some examples, the adenovirus vector further comprises transgenes or nucleic acid encoding a heterologous protein, and in some examples, the heterologous protein is an immunogenic polypeptide, such as an antigen of a mammalian pathogen.

The present invention also encompasses viral particles comprising adenovirus vectors of the present invention as well as compositions and host cells comprising adenovirus particles and adenovirus vectors of the present invention. In some examples, a composition further comprises a pharmaceutically acceptable carrier.

The present invention also provides compositions capable of inducing an immune response in a mammalian subject, said compositions comprising an adenovirus vector of the present invention and a pharmaceutically acceptable excipient. The present invention also provides methods for eliciting an immune response in a mammalian subject comprising administering a composition comprising an adenovirus vector of the present invention and a pharmaceutically acceptable excipient to said mammalian subject.

The present invention also provides methods of making an adenovirus vector of the present invention. In some examples, the present invention provides methods of preparing a porcine adenovirus comprising culturing a recombinant porcine adenovirus vector which is deleted in a porcine adenovirus sequence(s) essential for encapsidation, such that the vector is not capable of being encapsidated, wherein said adenovirus vector is optionally deleted in nucleic acid encoding adenoviral proteins necessary for replication; in the presence of a helper virus that comprises nucleic acid encoding the porcine adenovirus sequence essential for encapsidation and optionally any adenovirus protein necessary for replication of said adenovirus, and culturing the cell under conditions suitable for production of viral particles; and optionally recovering said viral particles. In some examples, the present invention provides methods of preparing an adenovirus comprising culturing an adenovirus vector which comprises a porcine adenovirus sequence(s) essential for encapsidation, wherein said porcine adenovirus sequence(s) essential for encapsidation is heterologous to said adenovirus vector under conditions suitable for production of viral particles; and optionally recovering said viral particles. In some examples, the vector is deleted in nucleic acid encoding adenoviral proteins necessary for replication and the vector is grown in the presence of a helper adenovirus that comprises the adenoviral proteins necessary for replication. In some examples, the present invention provides methods of preparing an adenovirus comprising the steps of introducing into a cell a) a recombinant adenovirus vector which comprises a porcine adenovirus sequence(s) essential for encapsidation, wherein said porcine adenovirus sequence(s) essential for encapsidation is heterologous to said adenovirus vector, wherein said adenovirus vector is deleted in nucleic acid encoding an adenoviral protein necessary for replication; and b) a helper virus that comprises nucleic acid encoding the adenovirus protein necessary for replication of said adenovirus; and culturing the cell under conditions suitable for production of viral particles; and optionally recovering said viral particles. In some examples of the method, the adenovirus vector comprises a mammalian ITR sequence. In some examples, the mammalian ITR sequence is a human ITR sequence and in other examples, is a bovine ITR sequence and in yet other examples is a porcine ITR sequence. In other examples, the adenovirus vector comprises a transgene. The present invention also provides methods of making a PAV comprising a modification of part or all of one or more E1 transcriptional control regions.

The present invention also provides vaccines for protecting a mammalian host against infection comprising a recombinant adenovirus vector or viral particles of the present invention and a pharmaceutically acceptable excipient.

BRIEF DESCRIPTION OF THE DRAWING(S)

FIGS. 1A-1B show the nucleotide sequence of PAV3 terminus. Numbers indicate the nucleotide position relative to the left terminus. Inverted terminal repeat(ITR) is shown by italic type. The cap site and ATG codon for E1A gene are shown in italic bold face. AT-rich motifs were underlined. FIG. 1A shows the nucleotide sequence of PAV3 left terminus (SEQ ID NO: 86). FIG. 1B shows the nucleotide sequence of PAV3 right terminus (SEQ ID NO: 87).

FIGS. 2A-2B provide a schematic diagram of PAV3 terminus. The ITR is shown by open box. AT-rich motifs are shown by filled box. The cap site and ATG codon for E1A gene are indicated by a filled circle and an arrow, respectively. The arrow also indicates the direction of transcription. Numbers indicate the nucleotide position relative to the left terminus. FIG. 2A shows a schematic diagram of PAV3 left terminus and FIG. 2B shows a schematic diagram of PAV3 right terminus.

Figures 3A, 3B:
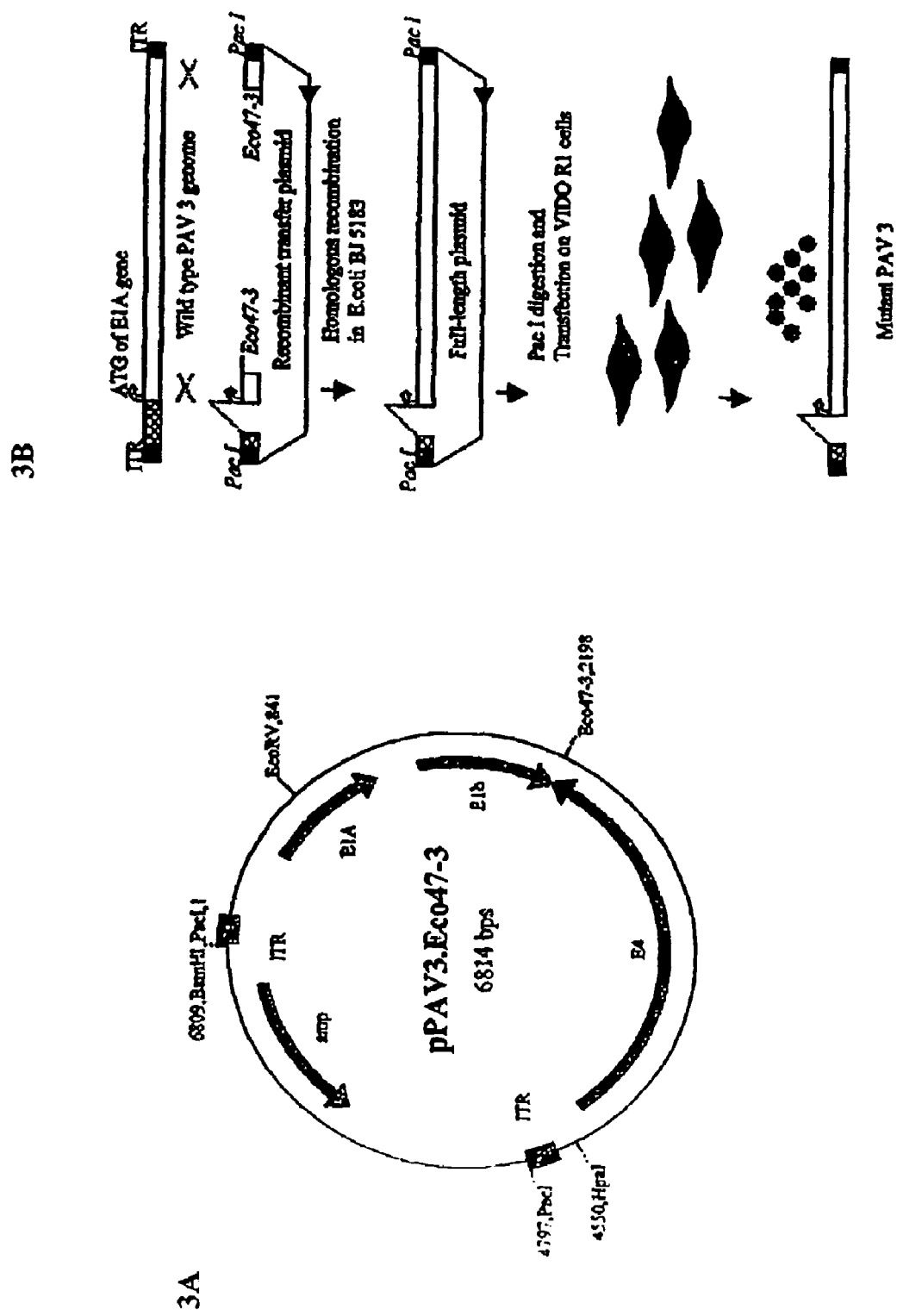

FIGS. 3A-3B show schematic diagrams of plasmid constructs. FIG. 3A shows a diagram of plasmid pPAV3.Eco47-3 used for producing deletion mutations. The left and right ITRs of PAV3 are indicated by filled boxes. PAV3 sequences are from the extreme left and right ends of the viral genome. The E1A, E1B, and E4 mRNAs, and their directions of transcription are shown by filled arrows. The numbers indicate the positions of restriction endonuclease cleavage sites used in this study in this plasmid relative to the first Pac I recognition site. FIG. 3B provides a schematic representation of the strategy used for the full-length plasmid and recombinant virus construction. The thin line indicates the plasmid DNA. PAV3 genomic DNA is indicated by open box. ITR is shown by filled box. Hatched boxes represent region in which deletion mutations were generated.

Figure 4:
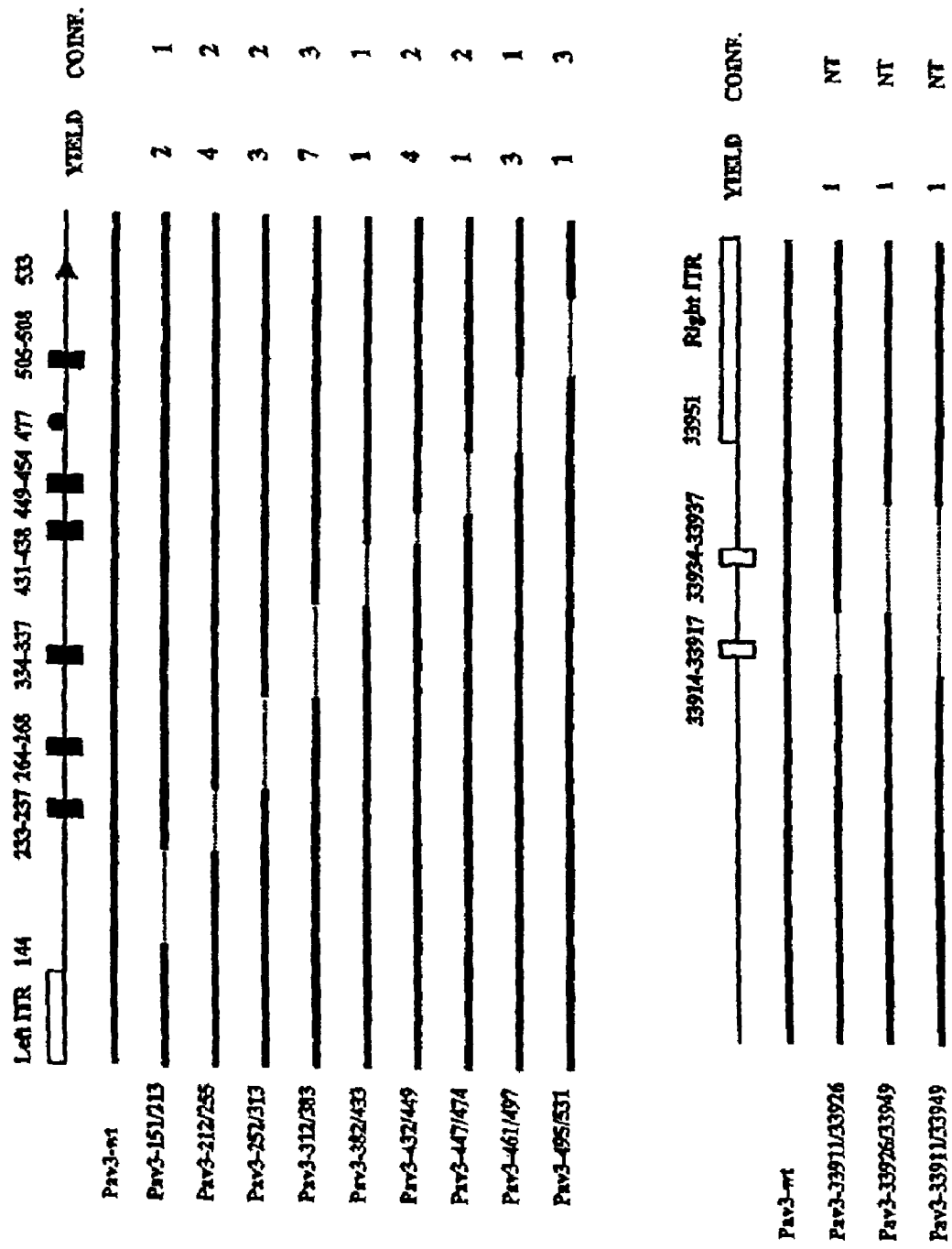
Figure 5:
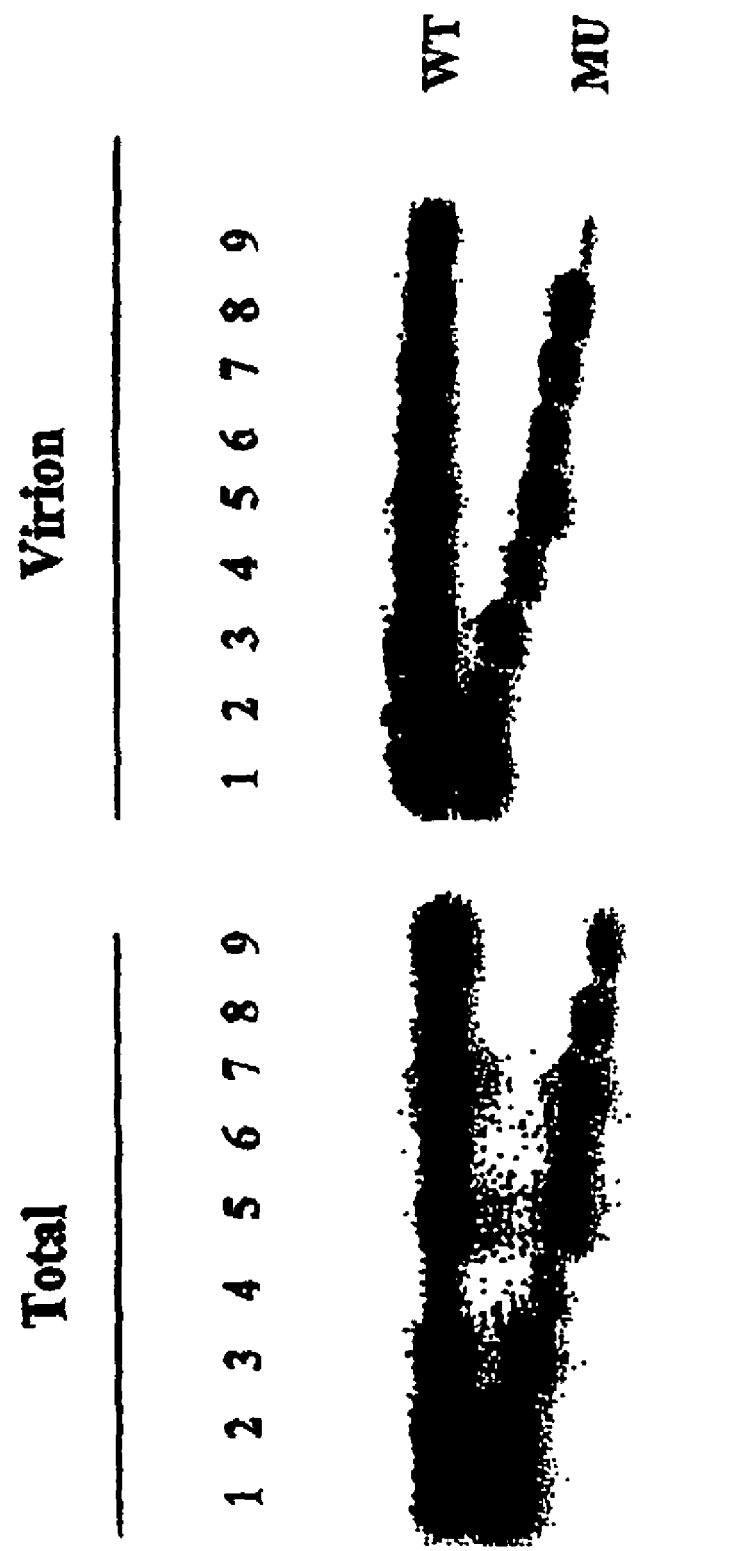

FIG. 4 provides a schematic view of viral mutants. The top of the figure shows the structure of the left terminus of PAV3 genome. The individual deletion mutant names are given on the left. The nucleotide numbers correspond to the first nucleotides present on either side of the deletion. The deleted sequences are indicated by dotted line. For single-virus infections, VIDO R1 cells were infected with the individual mutant viruses, and the infectious virus yield was determined by a plaque assay with cellular extracts prepared 48 h after infection. Mutant virus yields (YIELD) are expressed as the fold reduction in yield relative to that of the wild-type virus (Yield wild type/Yield mutant virus ratio). NV means nonviable mutant virus. In coinfection experiments, VIDO R1 cells were coinfected with a wild type virus and the individual mutant virus. At 48 h after infection, high-molecular-weight DNA was prepared from infected cells and encapsidated viral DNA was prepared from virion particles. Wild-type and mutant viral DNAs in each preparation were distinguished by restriction enzyme digestion and subsequent Southern hybridization analysis (FIG. 5). Mutant virus packaging efficiency (COINF.) is expressed as the fold reduction in packaged mutant DNA relative to the packaged coinfecting wild-type DNA. These data were normalized to the amount of each viral DNA (mutant and wild-type) present in total nuclear DNA. NT means no test.

FIG. 5 shows a southern hybridization analysis of viral DNA represented either in total DNA or in virion particles isolated from VIDO R1 cells coinfected with wild-type virus and the mutant viruses (FIG. 4). Total nuclear DNA and virion DNA were digested with Mfe I and EcoRV and subjected to Southern hybridization analysis using an PAV3 left end fragment between nucleotide (nt) 531 and 844 as a $^{32}$P-labeled probe. The corresponding wild-type (WT) and Mutant (Mu) left end DNA fragments are indicated. The mutant viruses tested were Pav3-151/213 (lane 1), Pav3-212/254 (lane 2), Pav3-252/313 (lane 3), Pav3-312/383 (lane 4), Pav3-382/433 (lane 5), Pav3-432/449 (lane 6), Pav3-447/474 (lane 7), Pav3-461/497 (lane 8), Pav3-495/531 (lane 9).

Figure 6:
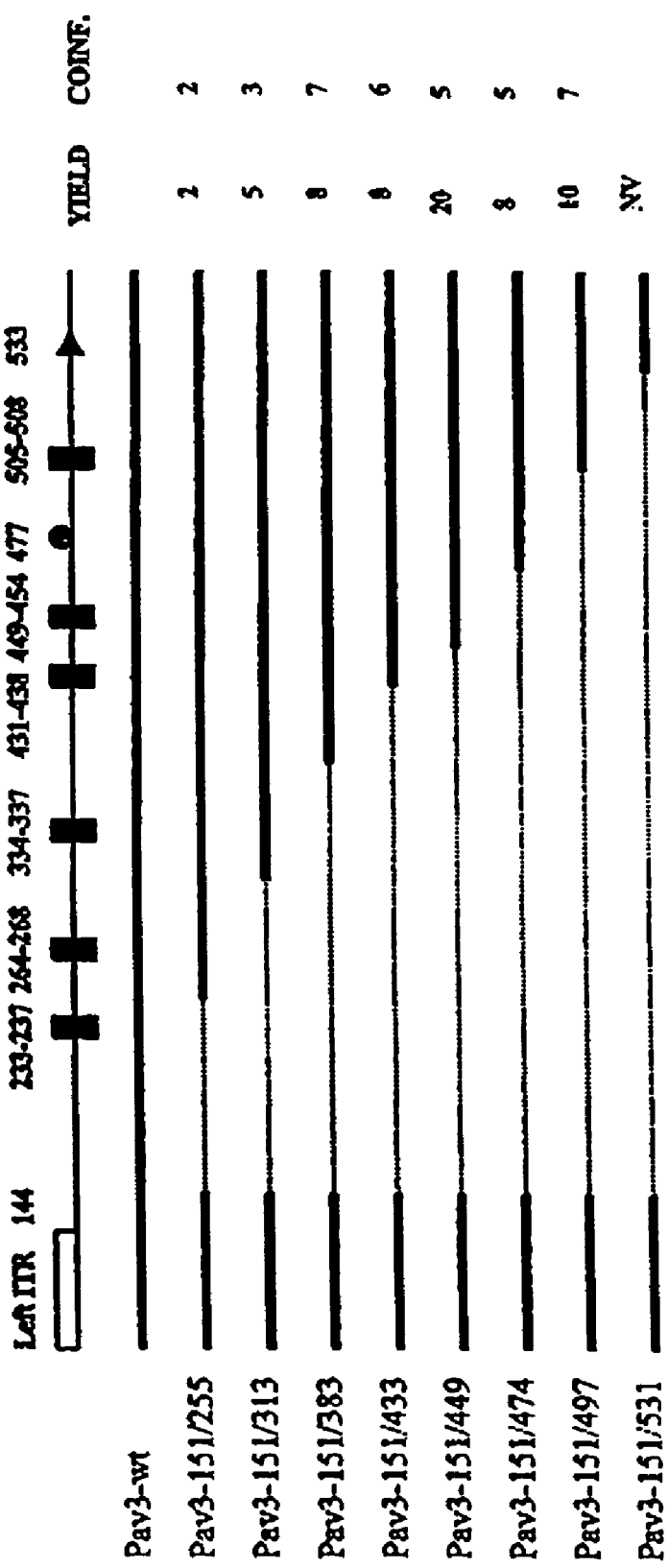

FIG. 6 provides a schematic view of viral mutants that carry deletions with a common start site at nt 151. The schematic, mutant names, endpoints of the deletion, and in vivo packaging analysis are as described in the legend to FIG. 4.

Figure 7:
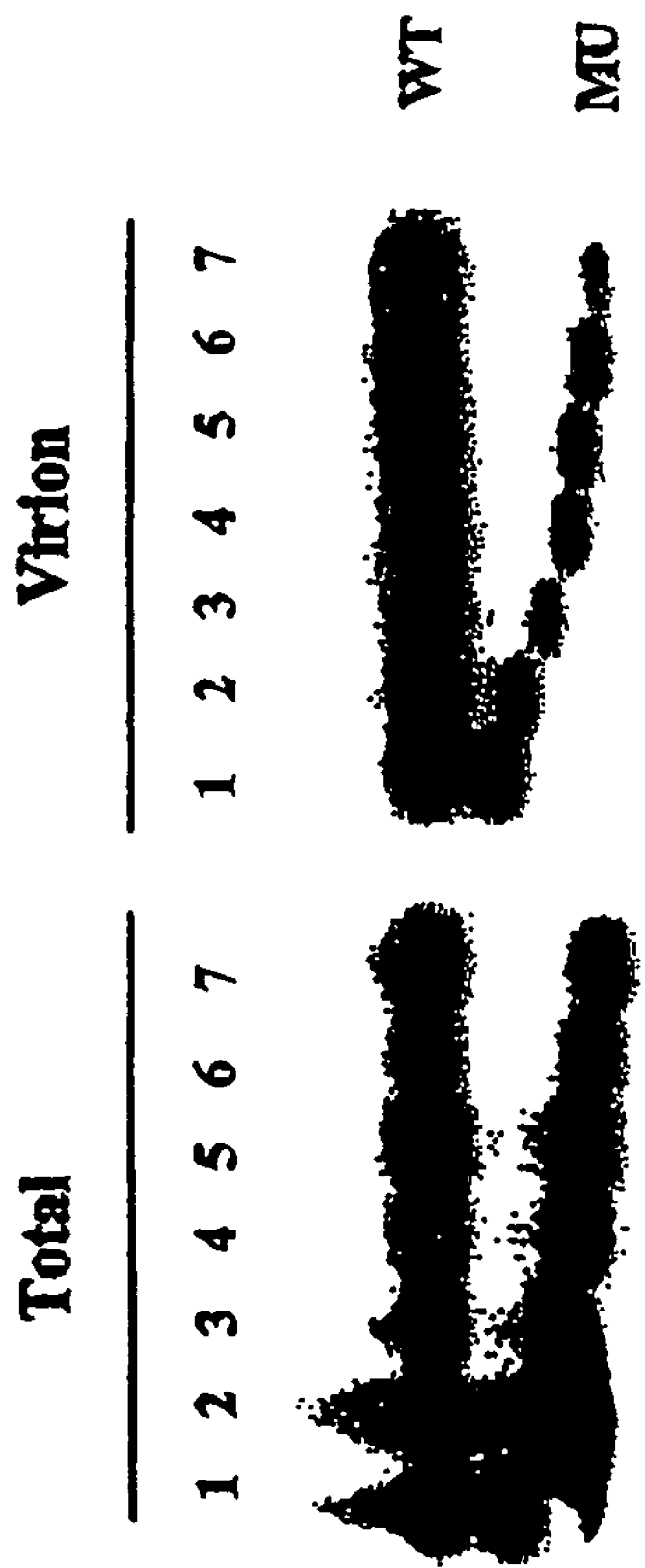

FIG. 7 shows a southern hybridization analysis of nuclear and virion DNA isolated from VIDO R1 cells coinfected with wild-type and individual mutant viruses (FIG. 6). Southern hybridization analysis of total nuclear DNA and virion DNA was performed as described in the legend to FIG. 5. The mutant viruses tested were Pav3-151/254 (lane 1), Pav3-151/313 (lane 2), Pav3-151/383 (lane 3), Pav3-151/433 (lane 4), Pav3-151/449 (lane 5), Pav3-151/474 (lane 6), Pav3-151/497 (lane 7).

Figure 8:
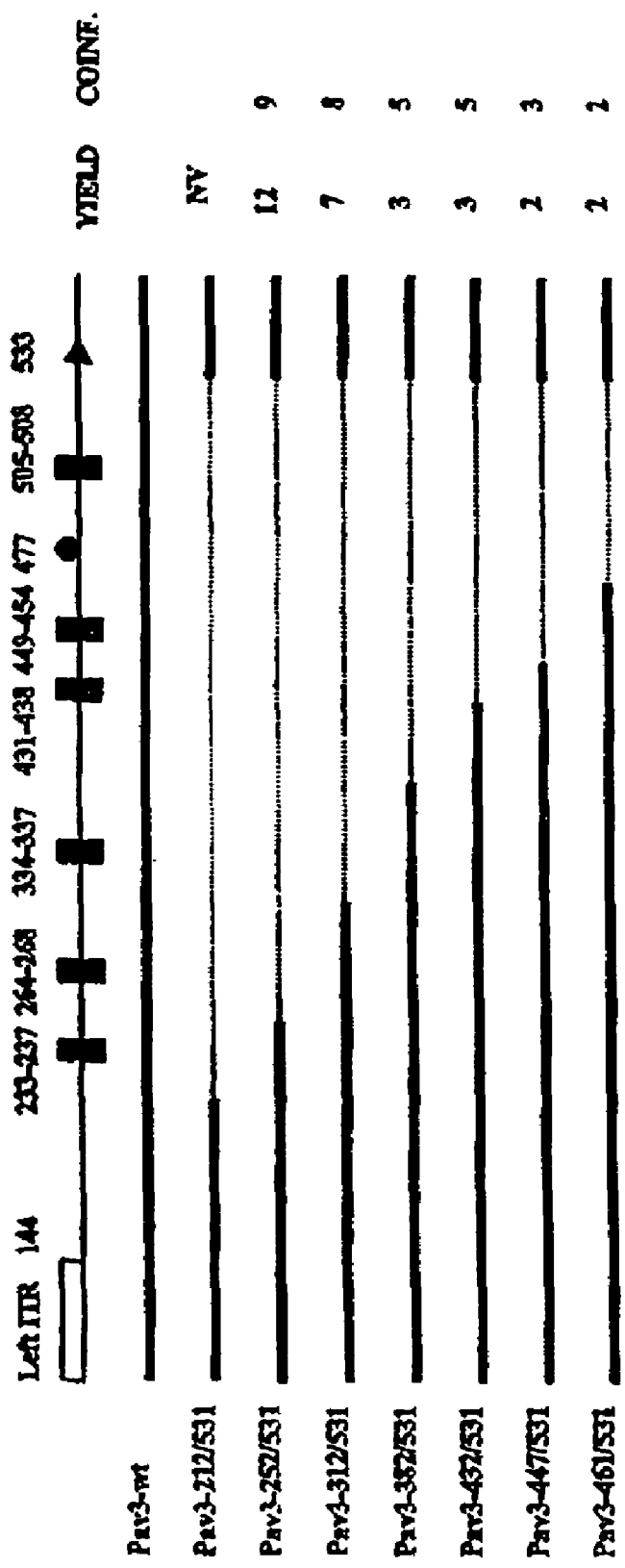

FIG. 8 shows a schematic view of viral mutants that carry deletions with a common start site at nt 531. The schematic, mutant names, endpoints of the deletion, and in vivo packaging analysis are as described in the legend to FIG. 4.

Figure 9:
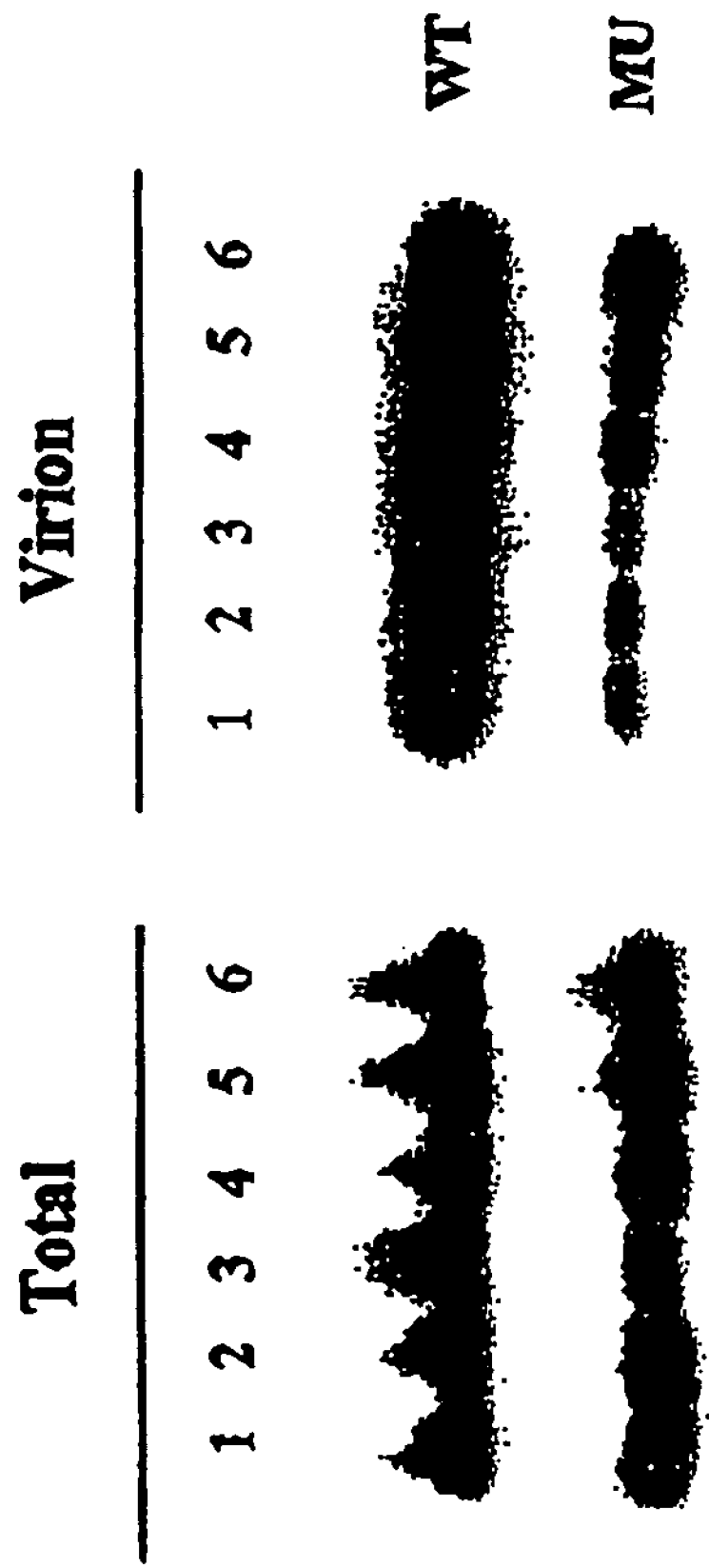

FIG. 9 provides a southern hybridization analysis of nuclear and virion DNA isolated from VIDO R1 cells coinfected with wild-type and individual mutant viruses (FIG. 6). Southern hybridization analysis of total nuclear DNA and virion DNA was performed as described in the legend to FIG. 5. The mutant viruses tested were Pav3-252/531 (lane 1), Pav3-312/531 (lane 2), Pav3-382/531 (lane 3), Pav3-432/531 (lane 4), Pav3-447/531 (lane 5), Pav3-461/531 (lane 6).

Figure 10:
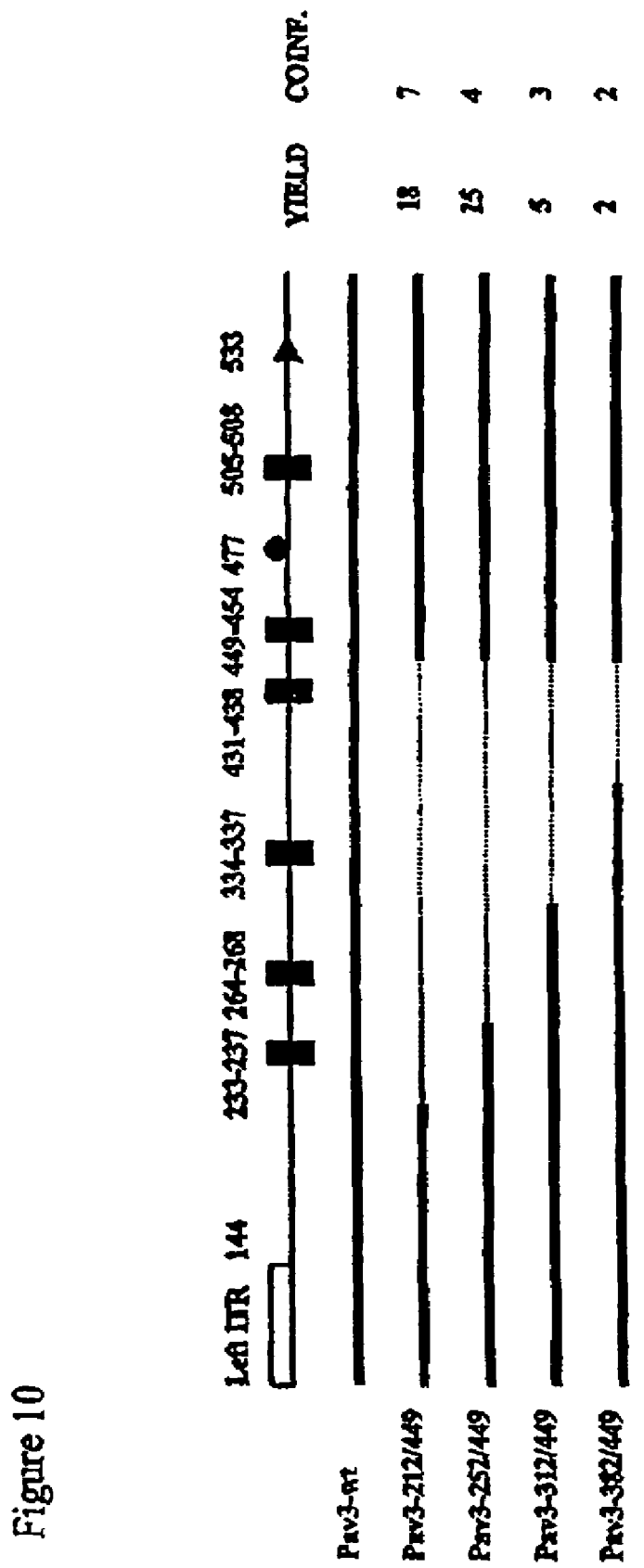

FIG. 10 provides a schematic view of viral mutants that carry deletions with a common start site at nt 449. The schematic, mutant names, endpoints of the deletion, and in vivo packaging analysis are as described in the legend to FIG. 4.

Figure 11:
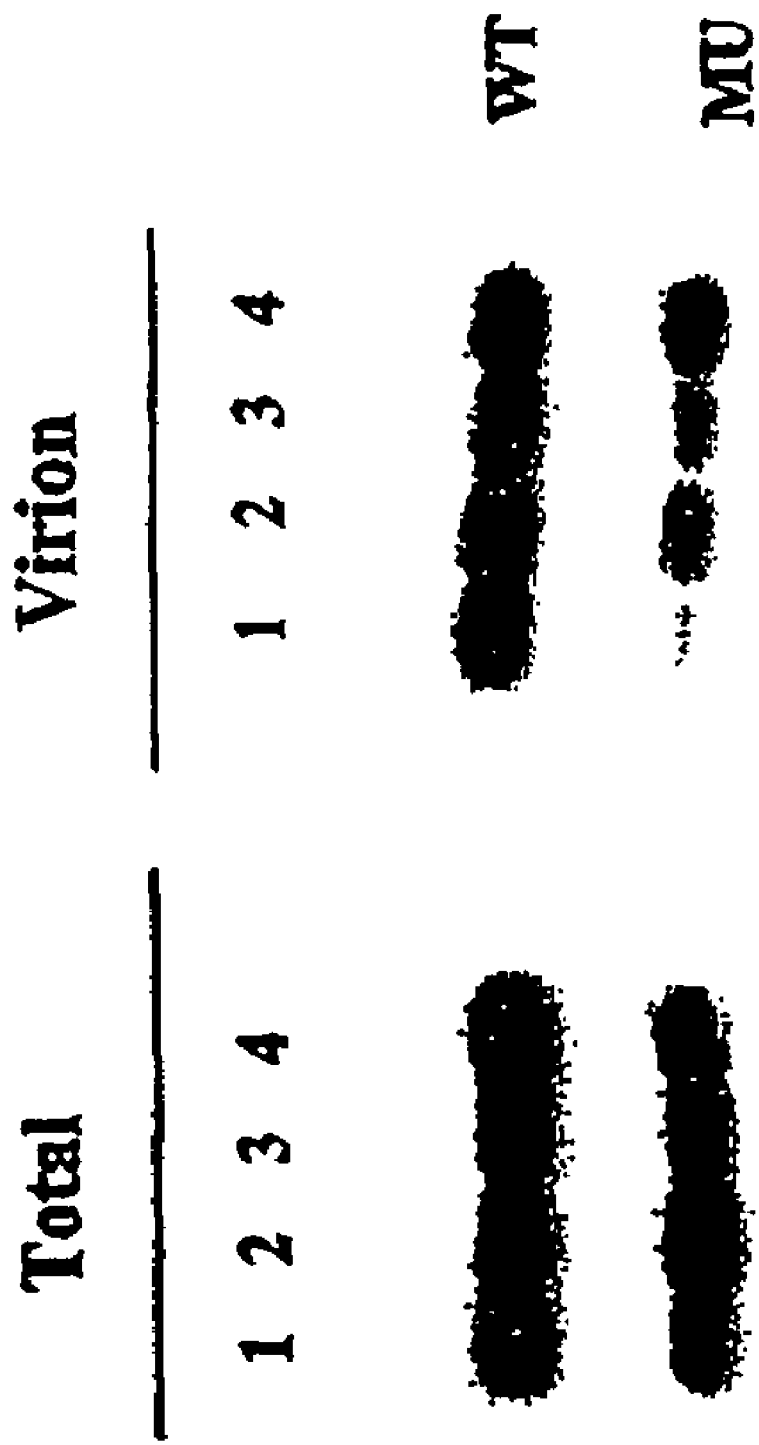

FIG. 11 provides a southern hybridization analysis of nuclear and virion DNA isolated from VIDO R1 cells coinfected with wild-type and individual mutant viruses (FIG. 6). Southern hybridization analysis of total nuclear DNA and virion DNA was performed as described in the legend to FIG. 5. The mutant viruses tested were Pav3-212/449 (lane 1), Pav3-252/449 (lane 2), Pav3-312/449 (lane 3), Pav3-382/449 (lane 4).

FIG. 12 shows a sequence alignment of packaging motifs of PAV3. Numbers indicate the position of AT sequences in the motifs relative to the left terminus of PAV3 genome (SEQ ID NOs: 1, 3, 5, 7, 9, 11).

Figure 13A:
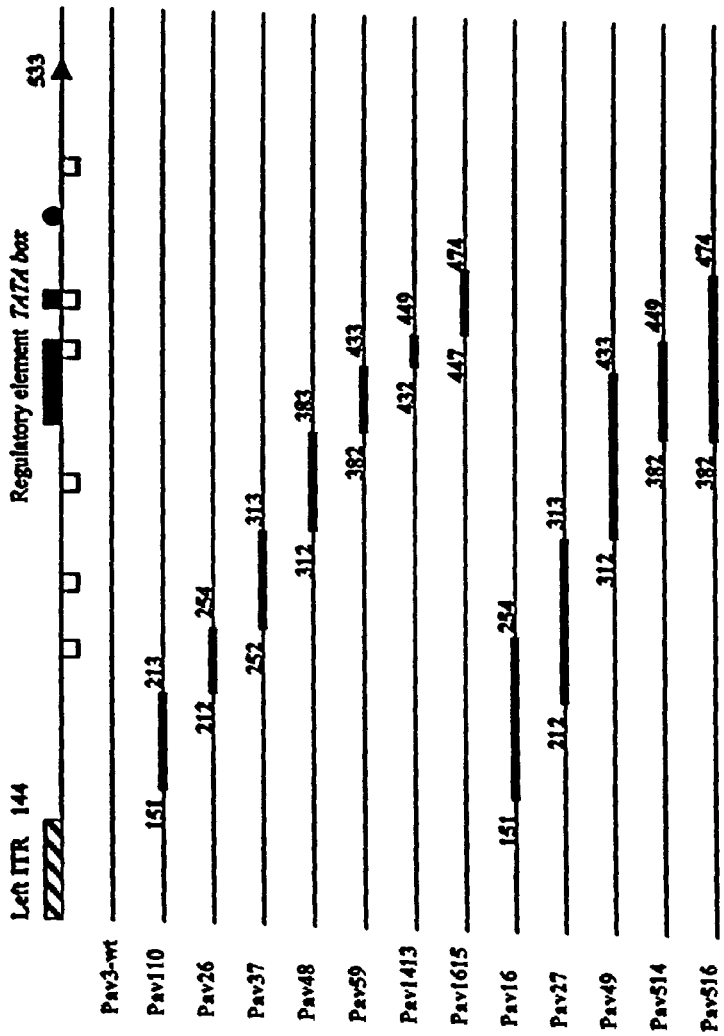
Figure 13B:
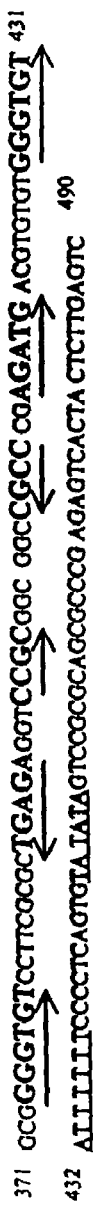

FIGS. 13A-13B. PAV-3 E1A transcriptional control region. (FIG. 13A). Schematic diagram of E1A transcriptional control region of PAV-3 and mutant viruses. The inverted terminal repeat (ITR) and potential cis-acting packaging domains are represented with hatched and open boxes, respectively. The E1A cap site and the translation start site (ATG) are indicated by the stippled circle and arrow, respectively. The individual deletion mutant names are given on the left. The deleted sequences are indicated with the bold lines. Nucleotide numbers relative to the left terminus of the genome designate the last base pair present on either side of deletions. (FIG. 13B). Nucleotide sequences (SEQ ID NO: 88) of the functionally two-faced regulatory element. Arrows designate repeated constituents located within regulatory element. Potential cis-acting packaging motifs were underlined.

FIGS. 14A-14F. Northern blot analysis. ST cells were infected with wild-type or mutant PAV-3s at a MOI of 40 PFU per cell and maintained in MEM containing 125 µg/ml AraC. The RNAs were isolated 7 h postinfection and then subjected to Northern blot analysis using [$^{32}$P]-labeled probes shown in Table 1. (A) E1A; (B) E1B; (C) E2A; (D) E3 and (E) E4. As a control, the RNAs stained with ethidium bromide in denaturing formaldehyde agarose gel were photographed (F). 18 s and 28 s rRNAs were indicated.

Figures 15A, 15B:
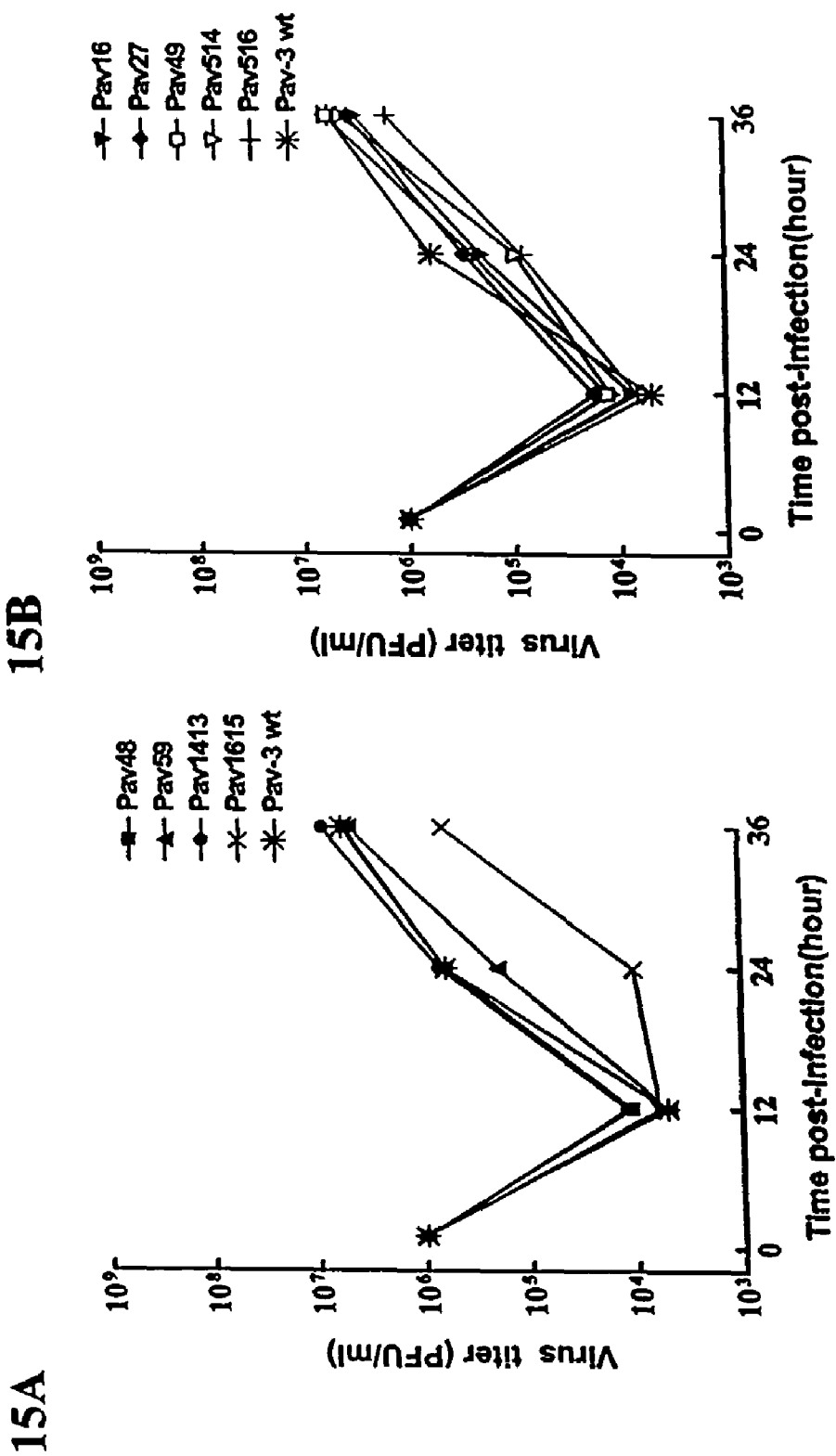

FIGS. 15A-15B. Growth kinetics of mutant viruses in ST cells. ST cells were infected with wild type or mutant PAV-3 at a MOI of 5 PFU per cell. Lysates were harvested at 12, 24, and 36 h postinfection. The titers were determined by plaque assay on VIDO R1 cells. The averaged values plus standard deviation (SD) are plotted and represented as PFU/ml.

Figure 16:
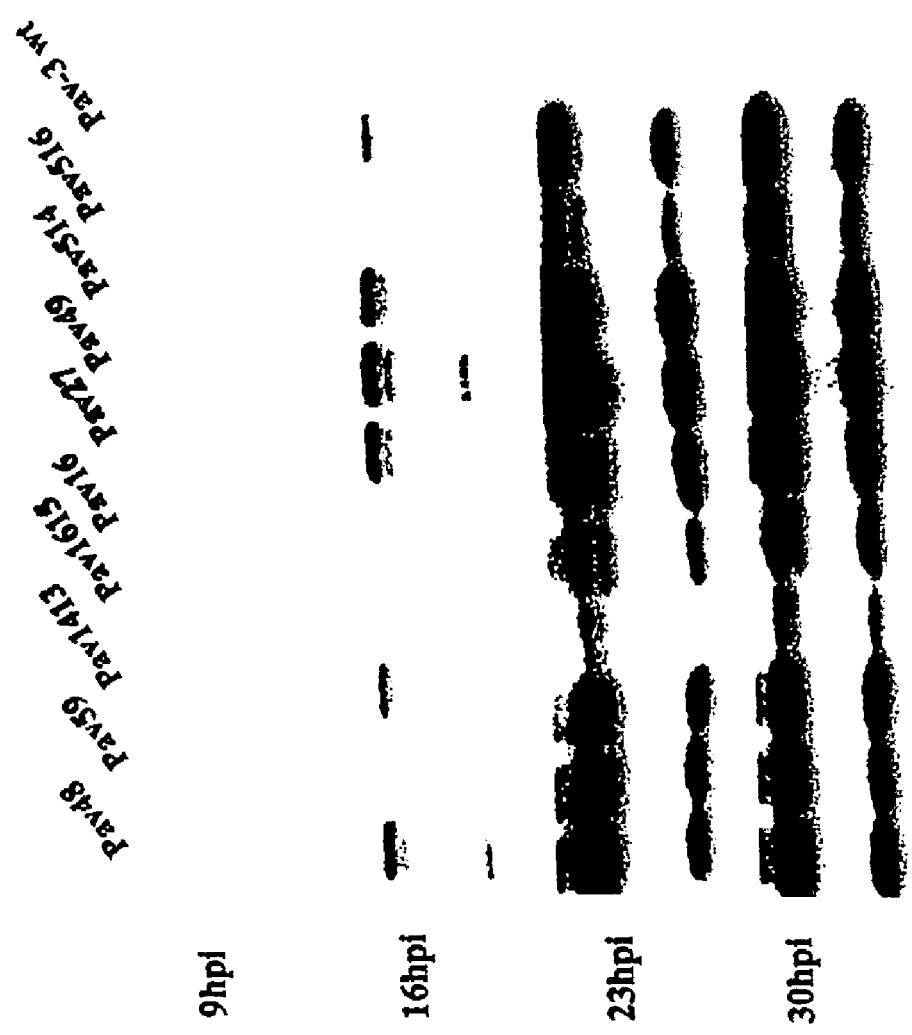

FIG. 16. Viral DNA accumulation in ST cells. ST cells were infected with the wild type or mutant PAV-3 at a MOI of 5 PFU per cell. The DNAs were prepared at 9, 16, 23, and 30 h postinfection. After digestion with HindIII, the agarose gel fractionated DNAs were subjected to Southern blot analysis using [$^{32}$P]-labeled PAV-3 genomic DNA fragment (nt 934 and 2190) as a probe.

Figure 17:
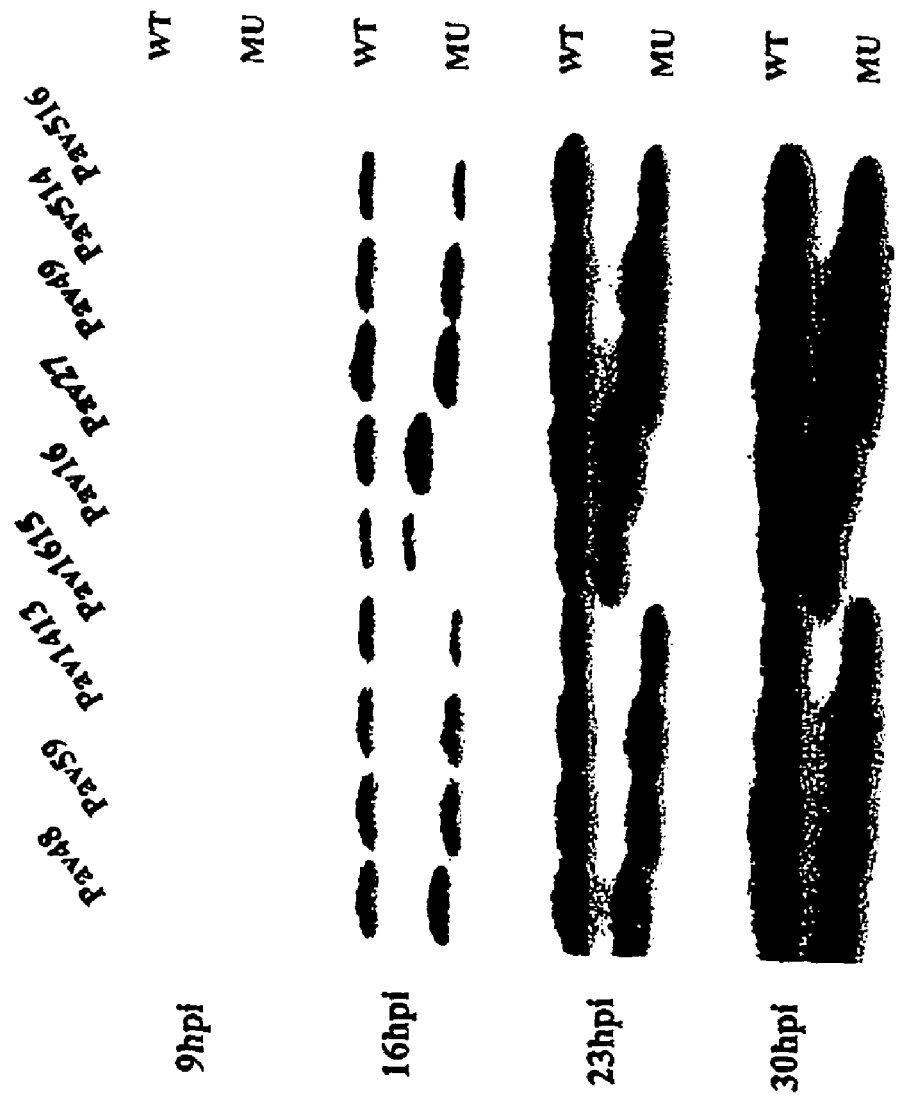

FIG. 17. Coinfection experiment. ST cells were co-infected with the wild type and mutant PAV-3 at a MOI of 5 PFU per cell each virus. The DNAs were prepared at 9, 16, 23, and 30 h postinfection. After digestion with KpnI/MfeI, Southern blot was performed using [$^{32}$P]-labeled PAV-3 genomic DNA fragment (nt 531 and 844) as a probe.

Figures 18A, 18B:
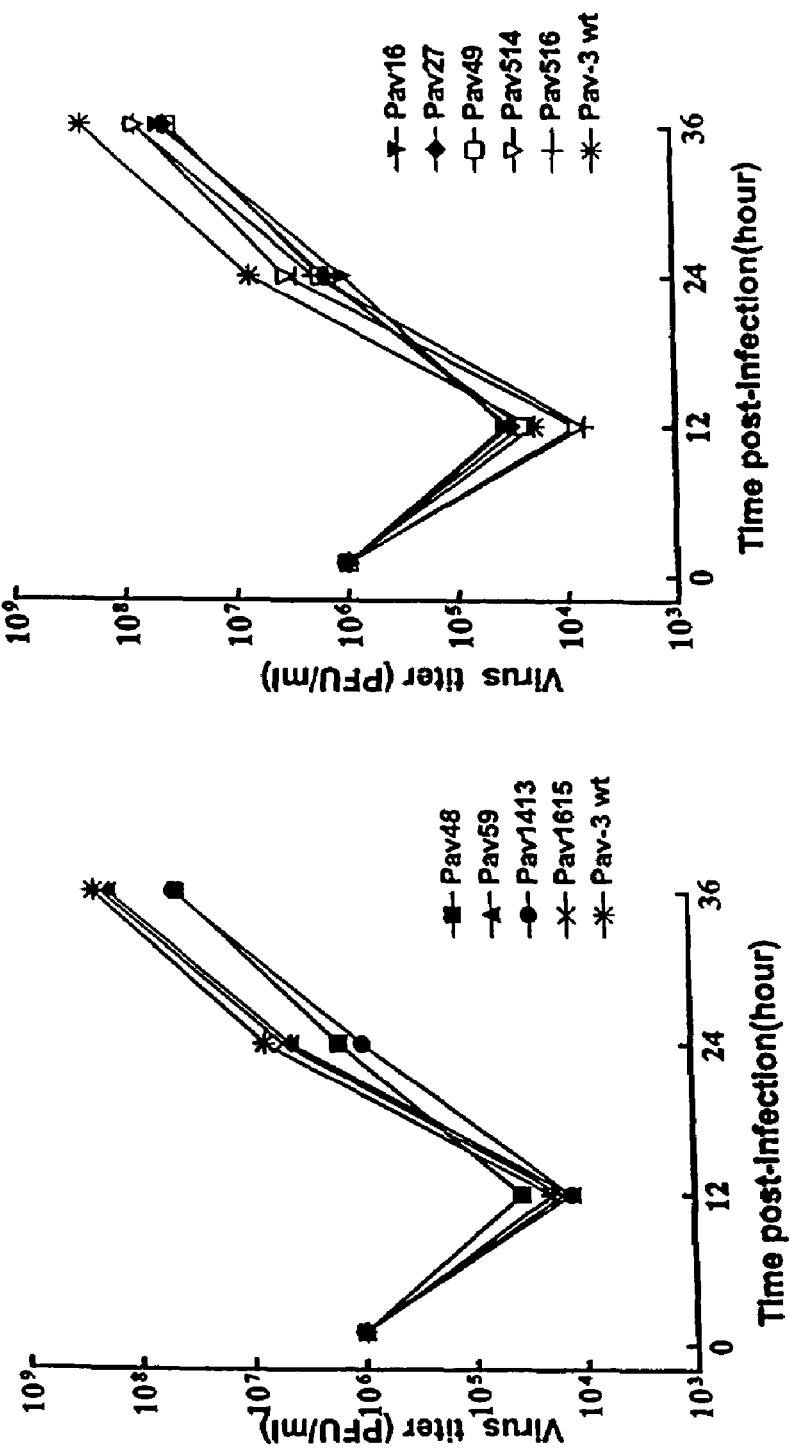

FIGS. 18A-18B. Growth kinetics of mutant viruses in VIDO R1 cells. The experiment conditions including virus infection, sample collection, and titer determination are as described in the legend of FIGS. 15A-15B.

Figure 19:
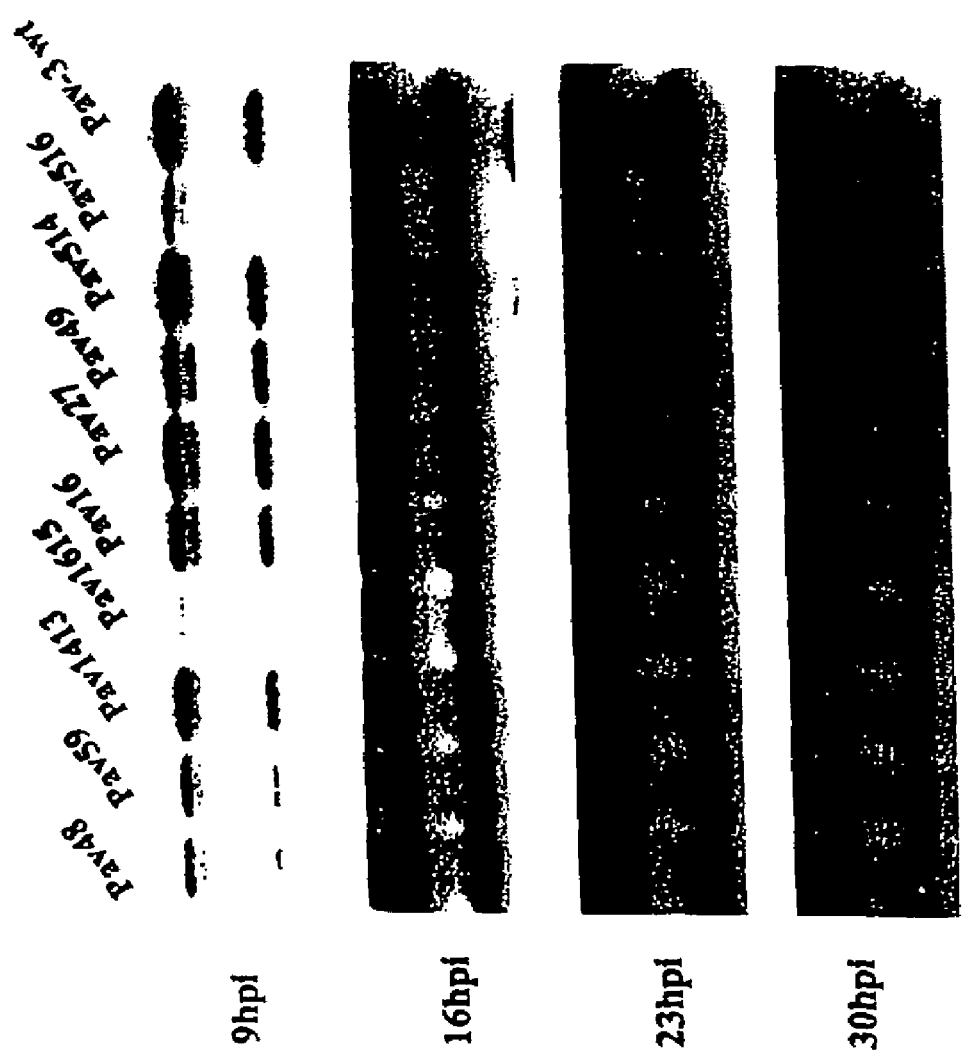

FIG. 19. Viral DNA accumulation in VIDO R1 cells. The experiment conditions including virus infection, DNA preparation, Southern hybridization are as described in the legend of FIGS. 16A-16B.

FIG. 20. Nucleotide sequence (SEQ ID NO: 89) of cis-acting packaging domain of PAV-3. Numbers indicate the nucleotide position relative to the left terminus of PAV-3 genome. The sequences analyzed in this study were in bold face and underlined. Packaging motifs were indicated with I, II, III, IV, V, and VI.

Figure 21A:
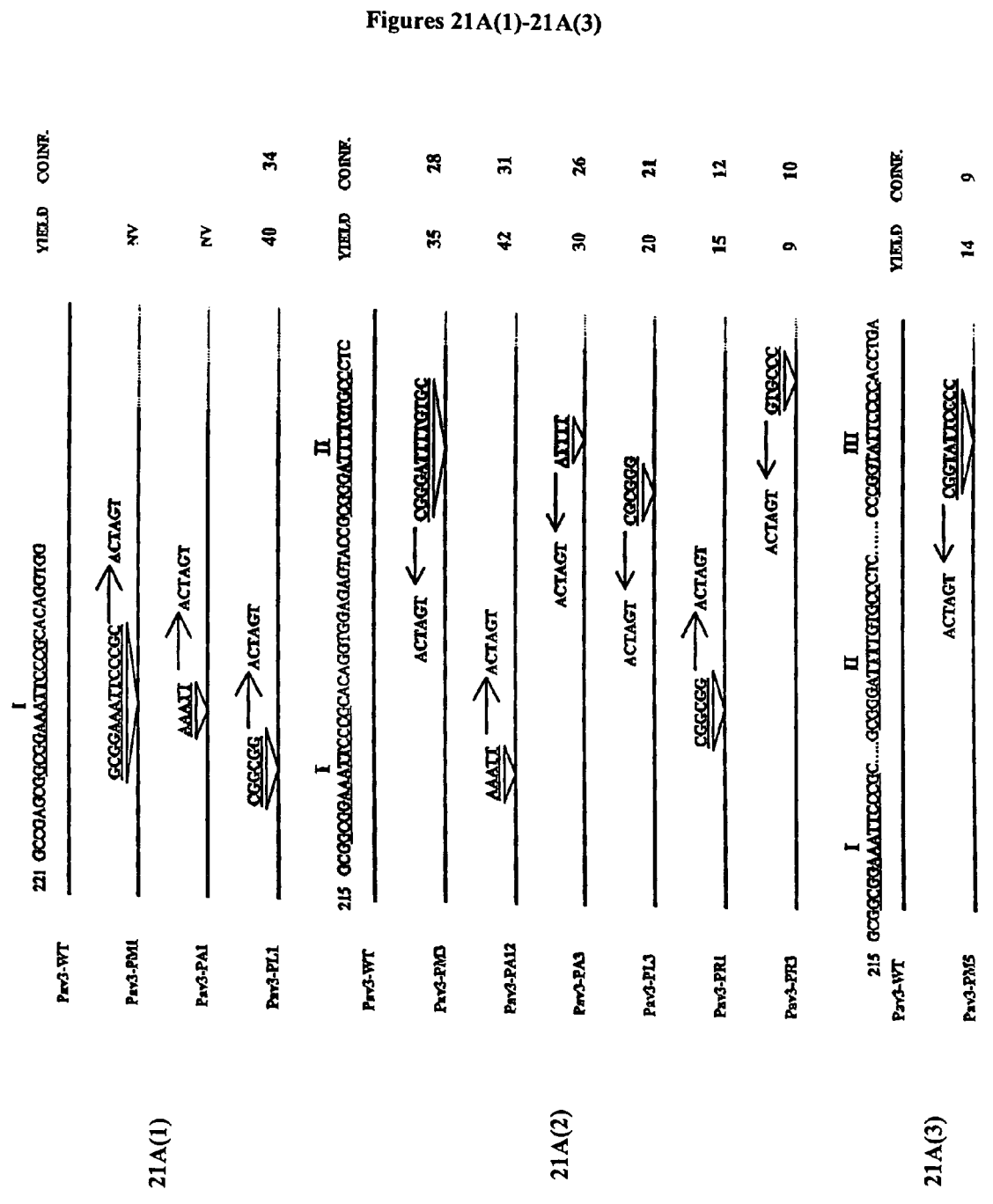
Figure 21B:
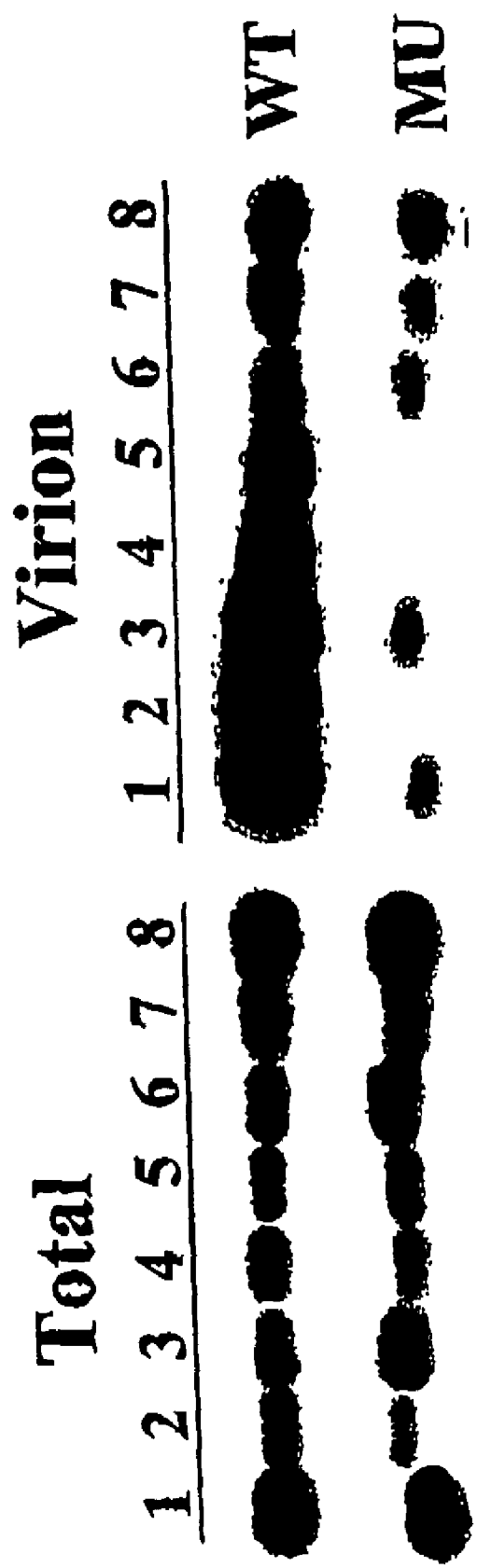

FIGS. 21A-21B. (SEQ ID NOs: 90-97) Analysis of viral mutants constructed in the background of Pav3-151/383 (1), Pav3-312/531 (2), and Pav3-382/531 (3). (A) The top of the figure shows the sequences analyzed. FIG. 21A (1) shows data from PAV3 packaging motif I. FIG. 21A (2) shows data for PAV3 packaging motif I and II. FIG. 21A (3) shows data for motif I, II, and III. The targeted sequences in this study were underlined. The SpeI linker replacing the targeted sequences was pointed with an arrow. The individual deletion mutant names are given on the left. The dotted lines indicate the sequences deleted are indicated by dotted line. Mutant virus yields (Yield) are expressed as the fold reduction in yield relative to that of wild-type virus. Mutant virus packaging efficiency (COINF) is expressed as the fold reduction in packaged mutant DNA relative to the packaged coinfecting wild type DNA. The data were normalized to the amount of each viral DNA (mutant and wild-type) present in total nuclear DNA. No viable virus (NV). (B) Southern hybridization analysis of viral DNA represented either in total DNA or in virion particles isolated from VIDO R1 cells coinfected with wild-type and the mutant viruses. Total nuclear DNA and virion DNA were digested with SpeI and KpnI and subsequently subjected to Southern hybridization analysis using PAV-3 left end fragment between nt 531 and 844 as a $^{32}$P-labeled probe. The corresponding wild-type (WT) and mutant (MU) left end DNA fragments are indicated. The mutant viruses tested were Pav3-PL1 (lane 1), Pav3-PM3 (lane 2), Pav3-PA12 (lane 3), Pav3-PA3 (lane 4), Pav3-PL3 (lane 5), Pav3-PR1 (lane 6), Pav3-PR3 (lane 7), Pav3-PM5 (lane 8).

Figure 22A:
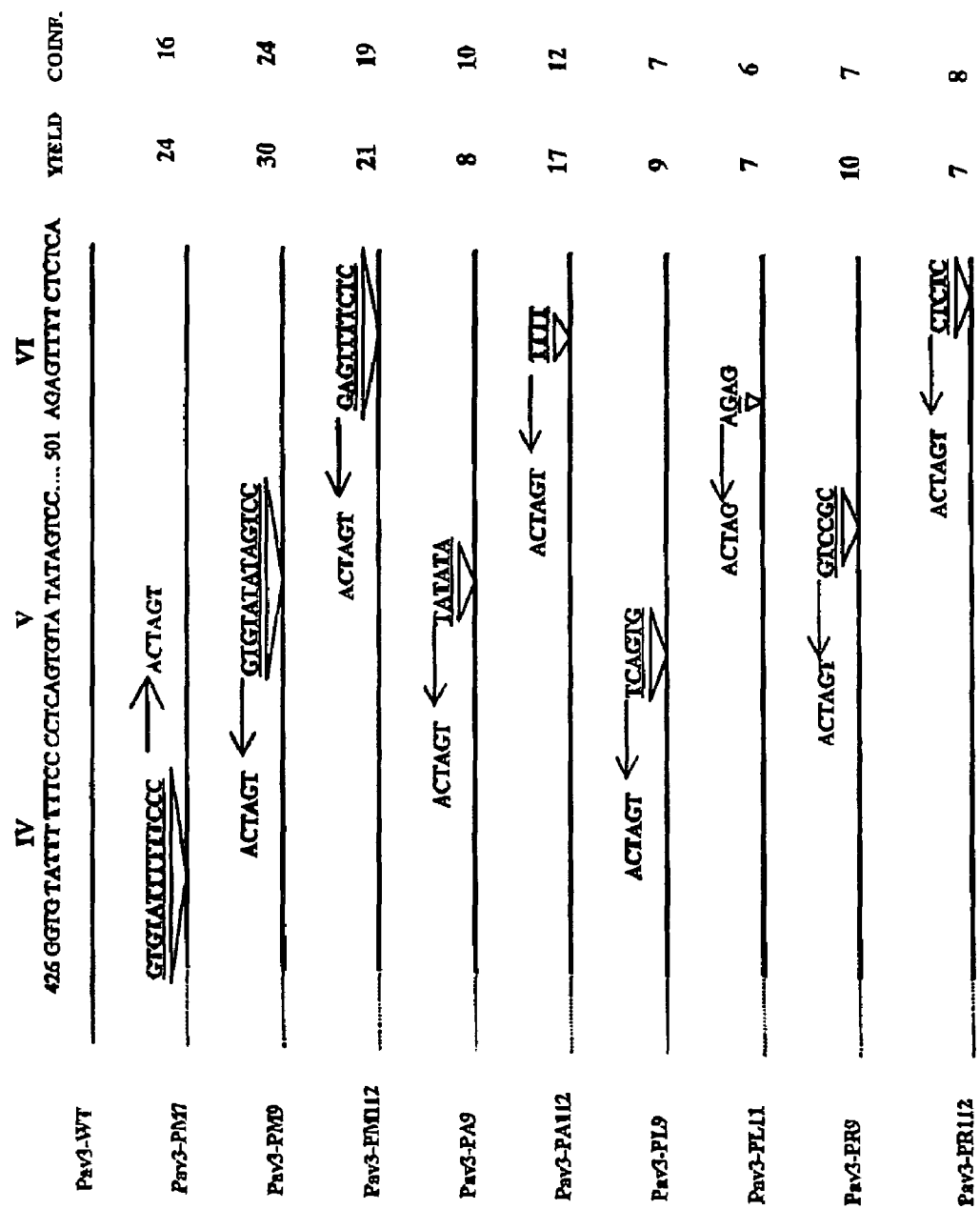
Figure 22B:
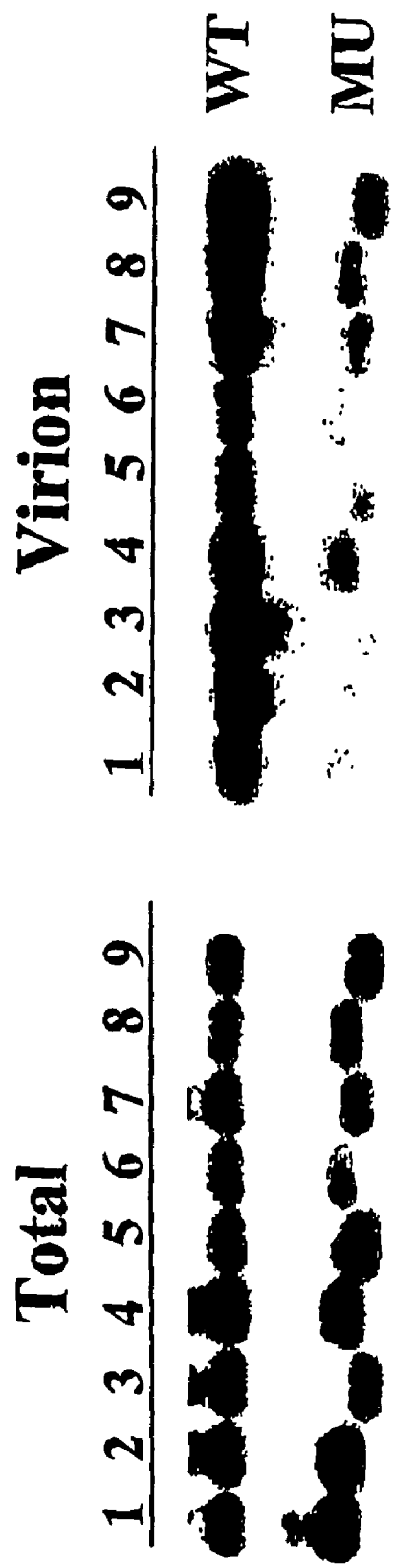

FIGS. 22A-22B. (SEQ ID NOs: 98-102) Analysis of viral mutants constructed in the background of Pav3-151/383. (A) The legend is as described for FIG. 21A. Data are shown for motifs PAV packaging motifs IV, V, and VI. (B) Southern hybridization analysis of nuclear and virion DNA isolated from VIDO R1 cells coinfected with wild-type and individual mutant viruses. Southern hybridization analysis of total nuclear DNA and virion DNA was performed as described in the legend to FIG. 21B. The mutant viruses tested were Pav3-PM7 (lane 1), Pav3-PM9 (lane 2), Pav3-PM112 (lane 3), Pav3-PA9 (lane 4), Pav3-PA112 (lane 5), Pav3-PL9 (lane 6), Pav3-PL11 (lane 7), Pav3-PR9 (lane 8), Pav3-PR112 (lane 9).

FIGS. 23A-23B. Analysis of virus mutant Pav3-PSR carrying packaging motif I through V at the right end of genome. (A). Diagramic view of wild-type and mutant viruses. ITR was indicated with open box. The filled and open arrows represent the start ATG colon of E1A gene and E4 gene, respectively, The packaging domain was shown with bold line. The deleted sequences were indicated by dotted line. Viral yield was determined as described in the legend to FIG. 21A. No viable virus (NV). (B). Southern hybridization analysis of nuclear and virion DNA isolated from VIDO R1 cells coinfected with wild-type and individual mutant viruses was performed as described in the legend to FIG. 21B.

DETAILED DESCRIPTION OF THE INVENTION

The present invention relates, in part, to the identification of porcine adenovirus (PAV) regions essential for encapsidation. The present invention provides vectors, such as adenovirus vectors, which comprise part or all of an isolated PAV sequence(s) essential for encapsidation. The present invention provides PAV vectors which comprise a deletion of part or all of an isolated PAV sequence(s) essential for encapsidation. The present invention also relates to expression systems, host cells and compositions comprising adenovirus vectors which comprise part or all of an isolated PAV sequence(s) essential for encapsidation as well as PAV vectors which comprise a deletion of part or all of an isolated PAV sequence(s) essential for encapsidation. An adenovirus vector comprising an isolated PAV sequence(s) essential for encapsidation can be used in a helper virus or helper plasmid for propagating recombinant adenovirus. An adenovirus vectors comprising an isolated PAV sequence(s) essential for encapsidation can be used in a recombinant adenovirus vector for propagation purposes. In some examples, an adenovirus vector comprising an isolated PAV sequence(s) essential for encapsidation is used to propagate a transgene. In other examples, an adenovirus vector comprising an isolated PAV sequence(s) essential for encapsidation is used to elicit an immune response in an individual. In other examples, an adenovirus vector comprising an isolated PAV region(s) essential for encapsidation is used to deliver a transgene to an individual.

Data shown herein demonstrate that the packaging motifs (sequences) of PAV3 are located between nucleotides 212 and 531 (SEQ ID NO:414) on the left end of the viral genome. There are at least six AT-rich motifs which can provide the packaging ability to PAV3. They overlap the promoter region of E1A gene of the virus. Packaging motifs of PAV3 have an AT-rich sequence followed by a GC-rich region. They appear to be functionally redundant, that is one or more encapsidation sequences can be deleted and viral DNA can still be encapsidated. Some of them alone can support the viral packaging and make PAV viable. The present invention also encompasses PAV sequence(s) essential for encapsidation of other PAVs such as for example, PAV5.

Transcriptional control regions of PAV E1 have been defined and are disclosed herein. The packaging domain between nucleotides 212 and 531 (SEQ ID NO:414) overlap with the transcriptional control region of E1. The present invention provides novel adenovirus vectors and adenovirus comprising modifications in the E1 transcriptional control regions disclosed herein.

The practice of the present invention employs, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984); Ausubel, et al., *Current Protocols In Molecular Biology*, John Wiley & Sons (1987, 1988, 1989, 1990, 1991, 1992, 1993, 1994, 1995, 1996); and Sambrook et al., *Molecular Cloning: A Laboratory Manual* (2$^{nd}$ Edition); vols. I, II & III (1989).

For general information related to mammalian adenovirus see "Fundamental Virology", second edition, 1991, ed. B. N. Fields, Raven Press, New York, pages 771-813; and "Fields Virology", third edition, 1995, ed. B. N. Fields, vol. 2, pages 2111-2172.

As used herein, "region(s) essential for encapsidation", an "encapsidation region", "sequence(s) essential for encapsidation", an "encapsidation sequence" and a "packaging domain" or "packaging motif" or "packaging sequence" (used interchangeably herein) refer to the sequence(s) of an adenovirus genome that is/are necessary for inserting the adenovirus DNA into adenovirus capsids. In further explanation, at least one porcine adenovirus sequence essential for encapsidation is necessary for inserting adenovirus DNA into adenovirus capsids. In some examples, an encapsidation sequence is cis-acting. A "porcine adenovirus" sequence(s) essential for encapsidation encompasses any porcine adenovirus sequence(s) essential for encapsidation as long as the sequence is capable of inserting the adenovirus DNA into adenovirus capsids. Illustrative examples are disclosed herein. As used herein, the phrase, "porcine adenovirus sequence(s) essential for encapsidation that is heterologous to the adenovirus vector", means that the adenovirus vector sequences are non-porcine adenovirus sequences. In some examples, the non-porcine adenovirus sequences are mammalian including but not limited to human, bovine, ovine, canine or feline sequences. The heterologous adenovirus vector sequences are not limited and can be any adenovirus sequence as long as the porcine adenovirus sequence(s) essential for encapsidation can function to insert the adenovirus DNA into an adenovirus capsid. In some examples, a porcine adenoviral sequence(s) essential for encapsidation is used in a recombinant adenovirus vector that comprises porcine adenovirus sequences, such as for example, a porcine adenovirus ITR. An adenovirus vector may be constructed to comprise multiple porcine adenovirus sequences essential for encapsidation, for example, multiple identical sequences or multiple different sequences, or the porcine adenovirus vector sequence may be heterologous, such as for example, of a different serotype, to the porcine adenovirus sequence essential for encapsidation. For example, the present invention encompasses an adenovirus vector comprising a PAV3 encapsidation sequence and PAV5 adenovirus sequence(s), such as a PAV5 ITR(s). In another example, the present invention encompasses an adenovirus vector comprising a PAV5 encapsidation sequence and PAV3 adenovirus sequence(s), such as a PAV3 ITR(s). An adenovirus vector may comprise one or more porcine adenovirus sequence(s) essential for encapsidation. In examples where the adenovirus comprises more than one porcine adenovirus sequence(s) essential for encapsidation, the sequences can be the same or different.

Under "transcriptional control" is a term well understood in the art and indicates that transcription of a polynucleotide sequence, usually a DNA sequence, can in some examples depend on its being operably (operatively) linked to an element which contributes to the initiation of, or promotes, transcription and in other examples, can act from a distance away, such as the case with enhancers. The adenovirus E1 transcriptional control regions described herein appear to act as enhancers and do not need to be operably linked to a promoter (or other control element) and can work at a distance from the promoter (or other control element) of the gene of interest. "Operably linked" refers to a juxtaposition wherein the elements are in an arrangement allowing them to function. The present invention provides isolated PAV E1 transcriptional control regions including nucleotides from about 252 to about 313; nucleotides from about 382 to about 433; nucleotides from about 432 to about 449; nucleotides from about 312 to about 382; nucleotides from about 312 to about 449; nucleotides from about 252 to about 449; and nucleotides from about 371 to about 432, all with respect to the PAV3 sequence disclosed in Reddy et al. 1998, *Virology* 251:414-426 and the sequence disclosed in FIG. 13B. Additional porcine adenovirus (PAV) E1 transcriptional control regions can be identified based on the PAV3 E1 transcription control regions disclosed herein. The present invention encompasses PAV and PAV vectors comprising a modification of one or more E1 transcriptional control regions, wherein the modification can be a deletion or addition of part or all of one or more E1 transcriptional control regions. The present invention encompasses PAV and PAV vectors comprising part or all of one or more additional E1 transcriptional control regions wherein the added sequence can be the same E1 transcriptional control region or a different E1 transcriptional control regions.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "gene" refers to a coding region of a polynucleotide. A "gene" may or may not include non-coding sequences and/or regulatory elements.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841-8; Chaturvedi et al. (1996) *Nucleic Acids Res.* 24: 2318-23; Schultz et al. (1996) *Nucleic Acids Res.* 24: 2966-73. A phosphorothioate linkage can be used in place of a phosphodiester linkage. Braun et al. (1988) *J. Immunol.* 141: 2084-9; Latimer et al. (1995) *Molec. Immunol.* 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes are provided herein.

In the context of adenovirus, a "heterologous" promoter is one which is not associated with or derived from an adenovirus gene.

In the context of adenovirus, an "endogenous" promoter is native to or derived from adenovirus. In the context of promoter, an "inactivation" means that there is a mutation of or deletion in part or all of the endogenous promoter, i.e., a modification or alteration of the endogenous promoter, such as, for example, a point mutation or insertion, which disables the function of the promoter.

In the context of an adenoviral vector, "inactivating" a viral function or a vector "lacking" a viral function means that there is a mutation of nucleic acid encoding the viral protein (e.g. for example, a point mutation, a deletion in part or all of the nucleic acid encoding the viral protein, an insertion within the nucleic acid encoding the viral protein), which reduces, disables or inactivates the viral protein function.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "individual" is a vertebrate, preferably a mammal, more preferably a human. Mammals include, but are not limited to, farm animals, such as cows, pigs and sheep; sport animals; rodents; primates; and pets, such as dogs and cats.

An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Porcine Adenovirus Encapsidation Sequences.

The transcriptional map and complete DNA sequence of PAV-3 genome was reported (Reddy et al., 1998, *Virus Res.* 58::97-106 and Reddy et al., 1998, *Virology* 251:414-426), specifically incorporated herein by reference. The genome termini share inverted terminal repeats (ITR) of 144 bp. Reddy et al., 1995, *Virology*, 212:237-239. PAV-3 expression and vaccine systems are disclosed in U.S. Pat. No. 6,492,343.

Studies using temperature sensitive mutants and pulse chase kinetics experiments established that adenovirus DNA is inserted into preformed, empty capsids late in the viral life cycle (D'Halluin, 1978, *J. Virol.* 26:344-357; D'Halluin, 1980, *J. Virol.* 33:88-89; D'Halluin, 1976, *J. Virol.* 26:357-363; Edvardsson, 1976, *J. Virol.* 19:539-547 and Edvardsson, 1978, *J. Virol.* 25:641-651). Other studies on viral incomplete particles containing DNA molecules of subgenomic length (Daniell, 1976, *J. Virol.* 19:685-708 and Tibbets, *Cell* 12:243-249) suggested that DNA packaging occurs in a polar fashion from left to right. Subsequent studies suggested that a cis-acting packaging domain located in the left end of in the adenovirus genome is required for the selective encapsidation of viral DNA (Hammarskjold, 1980, *Cell* 20:787-795 and Hearing, *J. Virol.*, 1987 61:2555-2558). However, the position and the orientation of this packaging domain is not strict as long as it is within first or last 600 bps.

The complete genome sequence of human adenovirus 5 is disclosed in GenBank accession number M73260 and the complete genome sequence of human adenovirus 2 is disclosed in GenBank accession number J01917, the sequences of which are incorporated herein by reference. The cis-acting packaging domain of human adenovirus -5 (HAV-5) is located in the left end 380 bp (Hearing, 1987,*J. Virol.* 61:2555-2558). It contains at least seven functionally redundant "A-repeat" domains, four of which (A1, AII, AV and AVI) are most relevant (Grable, 1990, *J. Virol.* 64:2047-2056). Mutational analysis of A-repeat consensus sequence (5'-TTTGN$_8$CG-3') (SEQ ID NO: 19) suggested that two elements 5'-TTTG-3' and 5'-CG-3' of the sequence, as well as the spacing (N$_8$) are critical for maximum packaging capacity (Schmid et al., 1997,*J. Virol.* 71:3375-3384). In addition to cis-acting sequences, a number of viral and/or cellular proteins are thought to be involved in adenovirus DNA packaging. Schmid and Hearing have detected some cellular proteins binding to the packaging sequences (Schmid, 1998, *J. Virol.* 72:6339-6347). Among viral proteins, the 52/55-kDa and IVa2 proteins have been shown to date to be required for viral DNA packaging (Zhang et al., 2000,*J. Virol.* 74:2687-2690; Gustin et al., 1998,*J. Virol.* 72:7860-7870). Interaction of IVa2 with the different components of the DNA packaging machinery has been shown to be serotype specific (Zheng et al., *J. Virol.* 75:10446-10459).

The present invention relates to the identification and characterization of PAV regions essential for encapsidation, also referred to herein as packaging domains. Based on the identification of cis-acting packaging domain of human adenovirus 5 (HAV5), 5' TTTGN8CG-3' (Schmid et al. 1997, *J. Virol.*

71:3375-3384) the PAV3 genome was searched to identify putative packaging domains. The packaging domain of porcine adenovirus type-3 is located between about nucleotide position 212 and about 531 (SEQ ID NO:414) at the left end of the genome. No regions were found that showed perfect homology with the consensus packaging domain of HAV5. As shown in the examples, a series of mutations were made in PAV-3 genome in order to determine the regions essential for PAV encapsidation. Data shown herein in the examples demonstrate that there are at least six AT-rich motifs which can provide the packaging ability to PAV3. Table 1 provides a listing of the regions.

TABLE 1

Alignment of Packaging sequences of PAV3 (numbering refers to the location of the A/T rich regions within the PAV-3 genome)

| | | | | |
|---|---|---|---|---|
| 233-237 | | CGG | AAATT (SEQ ID NO: 1) | CCCGCACA |
| 264-268 | | GGG | ATTTT (SEQ ID NO: 3) | GTGCCCTCT |
| 334-337 | | CGG | TATT (SEQ ID NO: 5) | CCCCACCTG |
| 431-438 | | GTG | TATTTTTT (SEQ ID NO: 7) | CCCCTCA |
| 449-454 | | GTG | TATATA (SEQ ID NO: 9) | GTCCGCGC |
| 505-508 | | GAG | TTTT (SEQ ID NO: 11) | CTCTCAGCG |
| 233-237 | GG | CGG | AAATT (SEQ ID NO: 2) | CCCGCACA |
| 264-268 | GC | GGG | ATTTT (SEQ ID NO: 4) | GTGCCCTCT |
| 334-337 | CC | CGG | TATT (SEQ ID NO: 6) | CCCCACCTG |
| 431-438 | GG | GTG | TATTTTTT (SEQ ID NO: 8) | CCCCTCA |
| 449-454 | CA | GTG | TATATA (SEQ ID NO: 10) | GTCCGCGC |
| 505-508 | TA | GAG | TTTT (SEQ ID NO: 12) | CTCTCAGCG |

Based on the identification of the PAV3 regions essential for encapsidation, the predicted packaging domains of PAV5 are shown in Table 2. PAV5 has at least six AT rich regions located between the left ITR (nt 1-154) and ATG (nt 418) of the E1A gene.

TABLE 2

Alignment of expected packaging sequences of PAV5 (numbering refers to the location of the A/T rich regions within the PAV-5 genome)

| | | | |
|---|---|---|---|
| 187-192 | (SEQ ID NO: 13) | CTGG | TATTTT | CCAC |
| 207-211 | | GTG | ATATT | GG |
| 217-220 | | CC | TTTA | CCTGGG |
| 272-277 | | CTC | AATTTTA | CCAC |
| 321-326 | | GGTCG | ATTTTT | CCAC |
| 349-356 | | CCC | TATTTATT | CTGCGCG |

Accordingly, the present invention provides isolated porcine adenovirus sequences essential for encapsidation that comprise a nucleotide sequence selected from the group consisting of AAATT; ATTTT; TATT; TATTTTTT; TATATA; TTTT; TATTTT; ATATT; TTTA; AATTTTA; ATTTTT; and TATTTATT.

The present invention also provides isolated porcine adenovirus sequences essential for encapsidation that comprise a nucleotide sequence selected from the group consisting of:

Motif I represented by $X_I$AAATT$Y_I$, wherein $X_I$ is selected from the group consisting of G, GG, CGG, GCGG, and GGCGG, and wherein $Y_I$ is selected from the group consisting of CCCGCACA, CCCGCAC, CCCGCA, CCCGC, CCCG, CCC, CC and C (SEQ ID NOS: 1, 2, 91, 103-139);

Motif II represented by $X_{II}$ATTTT$Y_{II}$, wherein $X_{II}$ is selected from the group consisting of G, GG, GGG, CGGG, and GCGGG, and wherein $Y_{II}$ is selected from the group consisting of GTGCCCTCT, GTGCCCTC, GTGCCCT, GTGCCC, GTGCC, GTGC, GTG, GT and G (SEQ ID NOS: 3, 4, 95, 140-181);

Motif III represented by $X_{III}$TATT$Y_{III}$, wherein $X_{III}$ is selected from the group consisting of G, GG, CGG, CCGG, and CCCGG, and wherein $Y_{III}$ is selected from the group consisting of CCCCACCTG, CCCCACCT, CCCCACC, CCCCAC, CCCCA, CCCC, CCC, CC, and C (SEQ ID NOS: 5, 6, 97, 182-223);

Motif IV represented by $X_{IV}$TATTTTTT$Y_{IV}$, wherein $X_{IV}$ is selected from the group consisting of G, TG, GTG, GGTG, and GGGTG, and wherein $Y_{IV}$ is selected from the group consisting of CCCCTCA, CCCCTC, CCCCT, CCCC, CCC, CC, and C (SEQ IDS NOS: 7,8, 100, 224-255);

Motif V represented by $X_V$TATATA$Y_V$, wherein $X_V$ is selected from the group consisting of G, TG, GTG, AGTG, and CAGTG, and wherein $Y_V$ is selected from the group consisting of GTCCGCGC, GTCCGCG, GTCCGC, GTCCG, GTCC, GTC, GT and G (SEQ ID NOS: 9, 10, 101, 256-292); and Motif VI represented by $X_{VI}$TTTT$Y_{VI}$, wherein $X_{VI}$ is selected from the group consisting of G, AG, GAG, AGAG, and TAGAG, wherein $Y_{VI}$ is selected from the group consisting of CTCTCAGCG, CTCTCAGC, CTCTCAG, CTCTCA, CTCTC, CTCT, CTC, CT and C (SEQ ID NOS: 11, 12, 99, 102, 293-333).

The present invention further provides isolated porcine adenovirus sequences essential for encapsidation that comprise a nucleotide sequence selected from the group consisting of:

Motif 1 represented by $X_1TATTTTY_1$, wherein $X_1$ is selected from the group consisting of G, GG, TGG, and CTGG, and wherein $Y_1$ is selected from the group consisting of C, CC, CCA, and CCAC (SEQ ID NOS: 13, 334-348);

Motif 2 represented by $X_2ATATTY_2$, wherein $X_2$ is selected from the group consisting of G, TG, and GTG, and wherein $Y_2$ is selected from the group consisting of G and GG (SEQ ID NOS: 14, 349-353);

Motif 3 represented by $X_3TTTAY_3$, wherein $X_3$ is selected from the group consisting of C and CC, and wherein $Y_3$ is selected from the group consisting of C, CC, CCT, CCTG, CCTGG, and CCTGGG (SEQ ID NOS: 15, 354-364);

Motif 4 represented by $X_4AATTTTAY_4$, wherein $X_4$ is selected from the group consisting of C, TC, and CTC, and wherein $Y_4$ is selected from the group consisting of C, CC, CCA, and CCAC (SEQ ID NOS: 16, 365-375);

Motif 5 represented by $X_5ATTTTTY_5$, wherein $X_5$ is selected from the group consisting of G, CG, TCG, GTCG, and GGTCG, and wherein $Y_5$ is selected from the group consisting of C, CC, CCA, and CCAC (SEQ ID NOS: 17, 376-394); and Motif 6 represented by $X_6TATTTATTY_6$, wherein $X_6$ is selected from the group consisting of C, CC, and CCC, and wherein $Y_6$ is selected from the group consisting of C, CT, CTG, CTGC, CTGCG, CTGCGC, and CTGCGCG (SEQ ID NOS: 18, 20, 395-413).

The present invention encompasses vectors, including adenovirus vectors, comprising a porcine adenovirus sequence(s) essential for encapsidation. At least one porcine adenovirus sequence essential for encapsidation is necessary for inserting adenovirus DNA into adenovirus capsids. In some examples, a vector, such as for example, an adenovirus vector comprises at least one porcine adenovirus sequence essential for encapsidation that comprises a nucleotide sequence selected from the group consisting of AAATT; ATTTT; TATT; TATTTTTT; TATATA; TTTT; TATTTT; ATATT; TTTA; AATTTTA; ATTTTT; and TATTTATT. In other examples, a vector, such as for example, an adenovirus vector, comprises at least one porcine adenovirus sequence essential for encapsidation that comprises a nucleotide sequence selected from the group consisting of:

Motif I represented by $X_IAAATTY_I$, wherein $X_I$ is selected from the group consisting of G, GG, CGG, GCGG, and GGCGG, and wherein $Y_I$ is selected from the group consisting of CCCGCACA, CCCGCAC, CCCGCA, CCCGC, CCCG, CCC, CC and C (SEQ ID NOS: 1, 2, 91, 103-139);

Motif II represented by $X_{II}ATTTTY_{II}$, wherein $X_{II}$ is selected from the group consisting of G, GG, GGG, CGGG, and GCGGG, and wherein $Y_{II}$ is selected from the group consisting of GTGCCCTCT, GTGCCCTC, GTGCCCT, GTGCCC, GTGCC, GTGC, GTG, GT and G (SEQ ID NOS: 3, 4, 95, 140-181);

Motif III represented by $X_{III}TATTY_{III}$, wherein $X_{III}$ is selected from the group consisting of G, GG, CGG, CCGG, and CCCGG, and wherein $Y_{III}$ is selected from the group consisting of CCCCACCTG, CCCCACCT, CCCCACC, CCCCAC, CCCCA, CCCC, CCC, CC, and C (SEQ ID NOS: 5, 6, 97, 182-223);

Motif IV represented by $X_{IV}TATTTTTTY_{IV}$, wherein $X_{IV}$ is selected from the group consisting of G, TG, GTG, GGTG, and GGGTG, and wherein $Y_{IV}$ is selected from the group consisting of CCCCTCA, CCCCTC, CCCCT, CCCC, CCC, CC, and C (SEQ ID NOS: 7, 8, 100, 224-255);

Motif V represented by $X_VTATATAY_V$, wherein $X_V$ is selected from the group consisting of G, TG, GTG, AGTG, and CAGTG, and wherein $Y_V$ is selected from the group consisting of GTCCGCGC, GTCCGCG, GTCCGC, GTCCG, GTCC, GTC, GT and G (SEQ ID NOS: 9, 10, 101, 256-292); and Motif VI represented by $X_{VI}TTTTY_{VI}$, wherein $X_{VI}$ is selected from the group consisting of G, AG, GAG, AGAG, and TAGAG, wherein $Y_{VI}$ is selected from the group consisting of CTCTCAGCG, CTCTCAGC, CTCTCAG, CTCTCA, CTCTC, CTCT, CTC, CT and C (SEQ ID NOS: 11, 12, 99, 102, 293-333).

In further examples, a vector, such as for example, an adenovirus vector, comprises at least one porcine adenovirus sequence essential for encapsidation that comprises a nucleotide sequence selected from the group consisting of:

Motif 1 represented by $X_1TATTTTY_1$, wherein $X_1$ is selected from the group consisting of G, GG, TGG, and CTGG, and wherein $Y_1$ is selected from the group consisting of C, CC, CCA, and CCAC (SEQ ID NOS: 13, 334-348);

Motif 2 represented by $X_2ATATTY_2$, wherein $X_2$ is selected from the group consisting of G, TG, and GTG, and wherein $Y_2$ is selected from the group consisting of G and GG (SEQ ID NOS: 14, 349-353);

Motif 3 represented by $X_3TTTAY_3$, wherein $X_3$ is selected from the group consisting of C and CC, and wherein $Y_3$ is selected from the group consisting of C, CC, CCT, CCTG, CCTGG, and CCTGGG (SEQ ID NOS: 15, 354-364);

Motif 4 represented by $X_4AATTTTAY_4$, wherein $X_4$ is selected from the group consisting of C, TC, and CTC, and wherein $Y_4$ is selected from the group consisting of C, CC, CCA, and CCAC (SEQ ID NOS: 16, 365-375);

Motif 5 represented by $X_5ATTTTTY_5$, wherein $X_5$ is selected from the group consisting of G, CG, TCG, GTCG, and GGTCG, and wherein $Y_5$ is selected from the group consisting of C, CC, CCA, and CCAC (SEQ ID NOS: 17, 376-394); and Motif 6 represented by $X_6TATTTATTY_6$, wherein $X_6$ is selected from the group consisting of C, CC, and CCC, and wherein $Y_6$ is selected from the group consisting of C, CT, CTG, CTGC, CTGCG, CTGCGC, and CTGCGCG (SEQ ID NOS: 18, 20, 395-413).

In other examples, a vector, such as for example, an adenovirus vector, comprises at least 2, at least 3, at least 4, at least 5, or at least 6 porcine adenovirus sequences essential for encapsidation. In some examples, when a vector, such as for example, an adenovirus vector, comprises at least 2 porcine adenovirus sequences essential for encapsidation, the at least 2 porcine adenovirus sequences essential for encapsidation are selected from the group consisting of Motif I, Motif II, Motif III, Motif IV, Motif V and Motif VI. In other examples, when a vector, such as for example, an adenovirus vector comprises at least 2 porcine adenovirus sequences essential for encapsidation, the at least 2 porcine adenovirus sequences essential for encapsidation are selected from the group consisting of Motif 1, Motif 2, Motif 3, Motif 4, Motif 5 and Motif 6. In some examples, the porcine adenovirus sequence(s) essential for encapsidation is heterologous to the adenovirus vector, i.e., is a non-porcine adenovirus, and in particular, a mammalian adenovirus. In some examples, the non-porcine adenovirus sequences are mammalian including but not limited to human, bovine, ovine, canine, feline or equine sequences. For example, the porcine adenovirus sequence(s) essential for encapsidation may be used in an adenovirus vector that comprises human adenovirus sequences, such as for example, human adenovirus inverted terminal repeat (ITR) sequences or other human adenoviral sequence(s), including human adenoviral sequences essential for replication or encapsidation. In another example, the porcine adenovirus sequence(s) essential for encapsidation may be used in an adenovirus vector that comprises bovine adenovirus sequences, such as, for example, bovine adenovirus inverted terminal repeat (ITR) sequences or other bovine sequence, including bovine adenoviral sequences essential for replication or encapsidation. In some examples, a porcine adenoviral sequence(s) essential for encapsidation is used in an adenovirus vector that comprises porcine adenovirus sequences. The heterologous adenovirus vector sequences are not limited and can be any adenovirus sequence as long as the porcine adenovirus sequence(s) essential for encapsidation can function to insert the adenovirus DNA into an adenovirus capsid. An adenovirus vector may be constructed to comprise multiple porcine adenovirus sequences essential for encapsidation, for example, multiple identical sequences or multiple different sequences, or the porcine adenovirus vector sequence may be heterologous, such as, for example, of a different serotype, to the porcine adenovirus sequence essential for encapsidation. In other examples, an adenovirus vector of the invention comprises a transgene.

In other examples of the present invention, an adenovirus vector comprises one or more porcine adenoviral sequences essential for encapsidation, wherein the mammalian adenovirus is heterologous to porcine, and the adenovirus vector lacks at least one adenoviral sequence encoding a viral protein function necessary for replication or has a mutation in at least one adenoviral sequence encoding a viral protein function necessary for replication. An adenovirus vector may have a deletion or part or all of an early gene, such as for example E1, such as E1A, E2, E3 or E4 or may have a deletion or part or all of late gene such as L1-L5. An adenovirus vector may have a deletion of multiple adenoviral sequences as long as sequences essential for replication and encapsidation are present on the adenovirus vector or provided by helper cells.

PAV E1 Transcriptional Control Regions

The present invention identifies PAV E1 transcriptional control regions. Accordingly, the present invention provides isolated PAV E1 transcriptional control regions as well as PAV and PAV vectors comprising modifications in part or all of one or more E1 transcriptional control region(s). In some examples, the modifications are deletions of part or all of one or more E1 transcriptional control region(s) and in other examples are additions of part or all of one or more of the same or different E1 transcriptional control region(s).

By analyzing porcine adenovirus type 3 (PAV-3) mutants containing deletion mutations in transcriptional control region of E1A transcription unit, a functionally two-faced regulatory element located upstream of TATA box of E1A promoter was defined. The E1 transcriptional control region overlaps the packaging domain between nucleotides(nt) 212 and 531 (SEQ ID NO:414) and is demonstrated herein to be between about nucleotide 212 to about nucleotide 449. All E1 transcriptional control region nucleotide numbering is based on the PAV3 nucleotide sequence disclosed in Reddy et al. 1998, *Virology* 251:414-426 and the sequence of PAV3 nucleotides 371 to 490 is disclosed in FIG. 13B.

A deletion of nucleotides from 432 to 449, alone increased E1B transcription and had no effect on E1A transcription. Deletion of the region of nucleotides 382 to 433 reduced the rate of E1A transcription, but increased that of E1B, which lies immediately downstream of E1A. A deletion of nucleotides 312 to 382 alone increased E1B transcription and had no effect on E1A transcription. A deletion of nucleotides 252 to 313 alone had no effect on E1A transcription and increased E1B transcription.

The virus mutant carrying the deletion of nucleotides 382 to 433, displayed defective replication at early times of infection, but replicated nearly as efficiently as wild-type PAV-3 at late times of infection. This defect was complemented with both co-infecting wild-type virus in a mixed infection and human adenovirus type 5 (HAV-5) E1A gene products constitutively expressed in VIDO R1 cells. The results indicated that the upstream activation sequences (UAS) of E1A transcription unit overlap the upstream repression sequences (URS) of E1B, although both units are transcribed from different promoters. Without being bound by theory, since the cooperation of E1A and E1B is essential for productive viral infection and transformation of primary cells in viral life cycle, the overlapping of regulatory sequences of E1A and E1B could represent a mechanism by which both genes are proportionally controlled at the transcriptional level.

FIG. 13B shows the region of PAV3 between nucleotides 371 and 490. The arrows designate repeated constituents in this nucleotide region. Hearing et al. (1986, Cell vol. 45:229-236) disclose adenovirus enhancer regions. The repeated constituents shown in FIG. 13B have the overall structural motif of adenovirus enhancer regions as described in Hearing et al, supra. One of skill in the art would be able to identify additional PAV E1 transcriptional control regions by aligning the PAV3 nucleotide sequence of Reddy et al., 1998, supra, with a PAV nucleotide sequence and identifying the structural motifs described in Hearing et al., supra, and disclosed herein in FIG. 13B that are upstream, that is, 5' to the E1 gene region. Such identified PAV E1 transcriptional control regions can be assayed for activity by methods known in the art and described herein in the examples. Such PAV E1 transcriptional control regions are encompassed within the invention.

In some examples where it is desirable to produce a PAV capable of growing for a period of time (such as for vaccine purposes or gene delivery purposes), a PAV E1 transcriptional control region corresponding to the PAV3 region from about nucleotide 382 to about nucleotide 433 is deleted, wherein E1A expression is decreased and E1B expression is increased. In some examples, for production of a lytic PAV (such as for use in methods for treating or ameliorating the symptoms of cancer, such as in reducing tumor growth or targeted killing of cancer cells) increasing expression of E1A and/or decreasing expression of E1B (which has anti-apoptotic activity) is desirable. For production of a lytic PAV, one or more PAV E1 transcription control region(s) corresponding to the PAV3 region from about nucleotide 432 to about 449 and/or from about nucleotide 312 to about nucleotide 382 and/or from about nucleotide 252 to about 313 are added to the PAV to suppress E1B function. In another example, for production of a lytic PAV, one or more PAV E1 transcriptional control regions corresponding to the PAV3 region from nucleotide 382 to about 433 are added to the virus. Such deletions and/or additions of PAV E1 transcriptional control regions should not inhibit encapsidation of the PAV.

Adenovirus genomes consist of a linear and double-stranded DNA molecules of about 36 kb which comprises about thirty genes involved in the viral cycle. The early genes (E1 to E4; E for early) are divided into 4 regions dispersed in the genome. The E1, E2 and E4 regions are essential for viral replication whereas the E3 region, which is involved in modulating the anti-adenovirus immune response in the host, is not.

The E1 region (E1A and E1B) encodes proteins responsible for the regulation of transcription of the viral genome. Expression of the E2 region genes (E2A and E2B) leads to the synthesis of the polypeptides needed for viral replication, including pTP (pre-Terminal Protein), pol (polymerase) and DBP (DNA Binding Protein) (Pettersson and Roberts, 1986, *In Cancer Cells* (Vol 4): DNA Tumor Viruses, Botchan and Glodzicker Sharp Eds pp 37-47, Cold Spring Harbor Laboratory, Cold Spring Harbor, N.Y.). The proteins encoded by the E3 region prevent cytolysis by cytotoxic T cells and tumor necrosis factor (Wold and Gooding, 1991, *Virology* 184, 1-8). The proteins encoded by the E4 region are involved in DNA replication, late gene expression and splicing and host cell shut off (Halbert et al., 1985, *J. Virol.* 56, 250-257).

The late genes (L1 to L5; L for late) encode predominantly the structural proteins, including the majority of the viral capsid proteins and partially cover the early transcription units. They are for the most part transcribed from the Major Late Promoter (MLP). In addition, the adenoviral genome carries, at its ends, cis-acting regions which are essential for encapsidation, consisting of inverted terminal repeats (ITR) situated at the 5' and 3' ends and an encapsidation region which follows the 5' ITR. The ITRs harbor origins of DNA replication whereas the encapsidation region is required for the packaging of adenoviral DNA into infectious particles. The viral DNA is associated with four polypeptides, namely V, VII, M and terminal protein (TP). The 55 kDa TP is covalently linked to the 5' ends of the DNA via a dCMP (Rekosh et al., 1977, *Cell* 11, 283-295; Robinson et al., 1973, *Virology* 56, 54-69). The other three polypeptides are noncovalently bound to the DNA and fold it in such a way as to fit into the small volume of the capsid. Sequences of ITRs are disclosed *Virology* 212:237-239; *Nucleic Acid Res.* 25:3495; and *Gene* 55:85-93.

PAV3 E1 and E4 regions have been characterized. E1A, E1B$^{large}$ and E4 ORF3 have been demonstrated to be essential for replication of PAV. For PAV3, the E1A region is from nucleotide 533 to nucleotide 1222, the E1B$^{small}$ all region is from nucleotide 1461 to nucleotide 2069, and the E1B$^{large}$ region is from nucleotide 1829 to nucleotide 3253. E1B$^{small}$ and E1B$^{large}$ nucleotide regions are overlapping and are differentially transcribed. Depending upon the intended use of the PAV vector, PAV constructs can be made comprising a deletion of part or all of the E1B$^{small}$ region. For example, if the entire E1B function is intended to be deleted, the entire E1B nucleotide region from nucleotides 1461 to 3253 can be deleted; or the region from nucleotides 1461 to 2069 can be deleted (which disrupts both E1B$^{small}$ and E1B$^{large}$ function); or the region from 1461 to 2069 and additionally, any portion of nucleotides 2069 through 3253 can be deleted. If it is intended to delete E1B$^{small}$ nucleotides while retaining E1B$^{large}$ function, nucleotides 1461 to 1829 are deleted, leaving the nucleotide region for E1B$^{large}$ intact. E4 ORF3 is essential for replication. E4 ORF 3 is from nucleotides (nt) 32681-33036. E4 ORF1 (nts 33436-33636), ORF2 (nts 33044-33404), ORF4 (nts 32264-32666), ORF5 (nts 32102-32248), ORF6 (nts 31834-32053), and ORF7 (nts 31303-31814) are non-essential for replication.

The present invention defines the PAV E1 transcriptional control region. The eukaryotic protein-coding gene is transcribed by the RNA polymerase II transcriptional machinery in which both RNA polymerase II and other protein factors are required for basal and regulated transcription, see Hampsey, M. (1998, *Microbiol. Mol. Biol. Rev.* 62:465-503). The transcription by RNA polymerase II is directed by cis-acting sequences termed RNA polymerase II transcriptional control region that consists of a complex variety of functional elements that are typically divided into core promoter elements and regulatory elements. Core promoter elements define the site for assembly of the transcription preinitiation complex (PIC) and include a TATA sequence located upstream of the transcription start site, and an initiator sequence (Inr) encompassing the start site. Regulatory elements are gene-specific sequences that are located upstream of the core promoter and control the rate of transcription initiation. They include both the upstream activation sequences (UAS) and the upstream repression sequences (IRS), which serve as binding sites for enhancers and repressors of transcription, respectively. Hampsey, M. supra.

The early region 1 (E1) of PAV-3 is located at the left end of genome, and contains E1A and E1B transcription units which map between 1.5 and 3.8 map units (mu), and between 4.0 and 12.2 mu, respectively. Reddy et al. (1998, *Virus Res.* 58:97-106), Reddy et al. (1998, *Virology.* 251:414-426). Both units are transcribed independently from different promoters where the TATA box of E1A promoter is located at nucleotide position (nt) 449 to 454, the TATA box of E1B promoter is located at nt 1331 to 1334, relative to the left terminus of viral genome.

As disclosed herein, the PAV-3 cis-acting packaging domain is located between about nucleotides 212 and 531 (SEQ ID NO:414). A packaging domain is required for encapsidation of PAV-3 DNA into virions late in the viral life cycle. Packaging domains overlap the transcriptional control region of E1A and consists of at least six AT-rich units with functional redundancy and importance hierarchy.

A functionally two-faced regulatory element in the transcriptional control region of E1A has been defined. This element lies upstream of TATA box of E1A promoter, and services as both UAS for E1A and URS for E1B. The element that is located upstream of E1A core promoter augments the transcription of E1A but represses the transcription of E1B. Deletion of the element reduced dramatically the steady state level of E1A-specific mRNAs early times post-infection, but led to an increase in the activity of the E1B transcription unit i.e. increased accumulation of E1B mRNA, which is located immediately downstream of E1A unit and led to the overexpression of E2A, E3 and E4mRNA.

Accordingly, as described herein, the present invention provides adenovirus vectors comprising a deletion and/or addition of part or all of one or more E1 transcriptional control regions described herein.

The present invention encompasses adenoviral vectors comprising transgenes. Transgenes of interest which are useful in the context of the present invention include genes coding for cytokines such as interferons and interleukins; genes encoding lymphokines; genes coding for membrane receptors such as the receptors recognized by pathogenic organisms (viruses, bacteria or parasites), including the HIV virus (human immunodeficiency virus); genes coding for coagulation factors such as factor VIII and factor IX; genes coding for dystrophins; genes coding for insulin; genes coding for proteins participating directly or indirectly in cellular ion channels, such as the CFTR (cystic fibrosis transmembrane conductance regulator) protein; genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene; genes coding for a protein inhibiting an enzyme activity, such as $\alpha_1$-antitrypsin or a viral protease inhibitor, for example; genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV; genes coding for antigenic epitopes in order to increase the host cell's immunity; genes coding for major histocompatibility complex classes I and II proteins, as well as the genes coding for the proteins which are inducers of these genes; genes coding for antibodies; genes coding for immunotoxins; genes encoding toxins; genes encoding growth factors or growth hormones; genes encoding cell receptors and their ligands; genes encoding tumor suppressors; genes coding for cellular enzymes or those produced by pathogenic organisms; and suicide genes. The HSV-1 TK suicide gene is mentioned as an example. This viral TK enzyme displays markedly greater affinity compared to the cellular TK enzyme for certain nucleoside analogues (such as acyclovir or gancyclovir). TK enzyme converts the analogues to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

This list is not restrictive, and any other transgene of interest can be used in the context of the present invention. In some cases the gene for a particular antigen can contain a large number of introns or can be from an RNA virus, in these cases a complementary DNA copy (cDNA) can be used. It is also possible that only fragments of nucleotide sequences encoding proteins can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above. Adenovirus vectors can be used to express antigens for provision of, for example, subunit vaccines. Antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). Antigenic polypeptide to be expressed by the virus systems of the present invention may contain full-length (or near full-length) sequences encoding antigens or, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. The peptide can encode a "protective epitope" that is capable of raising in the host a "protective immune response;" i.e., a humoral (ie. antibody-mediated), cell-mediated, and/or mucosal immune response that protects an immunized host from infection.

A gene of interest can be placed under the control of regulatory sequences suitable for its expression in a host cell. Suitable regulatory sequences are understood to mean the set of elements needed for transcription of a gene into RNA (ribozyme, antisense RNA or mRNA), for processing of RNA, and for the translation of an mRNA into protein. Among the elements needed for transcription, the promoter assumes special importance. It can be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention can be chosen to contain cell-specific regulatory sequences, or modified to contain such sequences. For example, a gene of interest for use in the present invention is placed under the control of an immunoglobulin gene promoter when it is desired to target its expression to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

Alternatively, targeting of a recombinant PAV vector to a particular cell type can be achieved by constructing recombinant hexon and/or fiber genes. The protein products of these genes are involved in host cell recognition; therefore, the genes can be modified to contain peptide sequences that will allow the virus to recognize alternative host cells.

For propagation of an adenovirus vector that lacks sequences encoding viral protein function necessary for replication, helper cell lines can be used to provide the missing or defective adenoviral function. For example, 293 cells provide E1 function, therefore, a human adenovirus having a deletion in E1 function can be propagated in 293 cells.

Parks et al., supra, describes a use of the Cre/lox system in adenovirus systems. In the present invention, a helper virus can be produced with loxP sites flanking portions of the helper virus genome that are to be deleted, such as a packaging domain of a helper adenovirus or other sequences, and a helper cell line is produced that expresses Cre recombinase. The Cre recombinase recognizes the loxP sites and deletes the portion of the helper virus flanked by the loxP sites.

The sequences for the porcine adenovirus regions essential for encapsidation and E1 transcriptional control regions may be isolated from a viral genome by conventional means (digestion with a restriction enzyme, PCR and the like) or may be produced by chemical synthesis. Optionally, in the context of the present invention, they may comprise mutations (deletion, substitution and/or addition of one or more nucleotides) compared with the native sequences as long as the mutations maintain the ability to encapsidate the virus. To determine if a mutation in a porcine adenovirus region essential for encapsidation maintains the ability to encapsidate virus, one of skill in the art would insert the sequence into an appropriate vector and determine the encapsidation properties in an appropriate cell line, for example, by determining the viral titer of the expression of a reporter gene. It is also possible to include other exogenous sequences (restriction sites and the like) along with the region essential for encapsidation. They may be inserted into the adenoviral vector according to the invention in addition to other sequences or as a replacement thereof. The insertion of porcine adenovirus regions essential for encapsidation into an adenovirus vector may take place in 5' or in 3' to adenovirus sequence, in a region of the adenovirus where an encapsidation site would be located or at a different site.

The present invention also encompasses kits containing the adenovirus vector(s) of this invention. These kits can be used for example for producing proteins for screening, assays and biological uses, such as for production of antigens for mammalian vaccine purposes. Procedures using these kits can be performed by clinical laboratories, experimental laboratories, medical practitioners, or private individuals.

The kits of the invention comprise an adenovirus vector described herein in suitable packaging. The kit may optionally provide additional components that are useful in the procedure, including, but not limited to, buffers, developing reagents, labels, reacting surfaces, means for detection, control samples, instructions, and interpretive information. The kit may include instructions for use of an adenovirus vector.

Construction of Recombinant Adenovirus Vectors

In one embodiment of the invention, a recombinant adenovirus vector comprising an isolated porcine adenovirus sequence essential for encapsidation and/or an E1 transcriptional control region and/or a transgene is constructed by in vivo recombination between a plasmid and an adenoviral genome. Generally, transgenes are inserted into a plasmid vector containing a portion of the desired adenovirus genome, and in some examples, the adenovirus genome is heterologous to porcine adenovirus sequence essential for encapsidation, wherein the adenovirus genome may possess a mutation of, for example, a deletion of one or more adenoviral sequences encoding viral proteins. In some examples, adenovirus sequences encoding protein function essential for viral replication, such as the E1 region, are mutated, such as for example, deleted in part or all of the sequence. The transgene is inserted into the adenovirus insert portion of the plasmid vector, such that the transgene is flanked by adenovirus sequences that are adjacent on the adenovirus genome. The adenovirus sequences serve as "guide sequences," to direct insertion of the transgene to a particular site in the adenovirus genome; the insertion site being defined by the genomic location of the guide sequences. Porcine adenovirus packaging sequences can be added into an adenovirus vector by means known to those of skill in the art.

The vector is generally a bacterial plasmid, allowing multiple copies of the cloned sequence to be produced. In one embodiment, the plasmid is co-transfected, into an appropriate host cell, with an adenovirus genome, or portion thereof. The adenovirus genome can be isolated from virions, or can comprise a genome that has been inserted into a plasmid, using standard techniques of molecular biology and biotechnology. In some examples, adenovirus vector sequences can be deleted in regions such as, for example, E1, E3, E4 and/or the region between E4 and the right end of the genome and/or late regions such as L1-L5. Adenovirus genomes can be deleted in essential regions, such as E1, if the essential function are supplied by a helper cell line. In some examples, the adenovirus vector is deleted in multiple nucleic acid sequences encoding viral proteins as long as any sequences essential for replication are provided by a helper virus.

Insertion of the cloned transgene into a viral genome occurs by in vivo recombination between a plasmid vector (containing transgene sequences flanked by adenovirus guide sequences) and an adenovirus genome following co-transfection into a suitable host cell. The adenovirus genome contains inverted terminal repeat (ITR) sequences required for initiation of viral DNA replication (Reddy et al. (1995), *Virology* 212:237-239). Incorporation of the cloned transgene into the adenovirus genome thus places the transgene sequences into a DNA molecule containing adenoviral sequences.

Incorporation of the cloned transgene into an adenovirus genome places these sequences into a DNA molecule that can be replicated and packaged in an appropriate helper cell line. Multiple copies of a single transgene sequence can be inserted to improve yield of the gene product, or multiple transgene sequences can be inserted so that the recombinant virus is capable of expressing more than one heterologous gene product. The transgene sequences can contain additions, deletions and/or substitutions to enhance the expression and/or immunological effect of the expressed gene product(s).

Attachment of guide sequences to a heterologous sequence can also be accomplished by ligation in vitro. In this case, a nucleic acid comprising a transgene sequence flanked by an adenovirus guide sequences can be co-introduced into a host cell along with the adenovirus genome, and recombination can occur to generate a recombinant adenovirus vector. Introduction of nucleic acids into cells can be achieved by any method known in the art, including, but not limited to, microinjection, transfection, electroporation, $CaPO_4$ precipitation, DEAE-dextran, liposomes, particle bombardment, etc.

In one embodiment of the invention, a recombinant adenovirus expression cassette can be obtained by cleaving a wild-type adenovirus genome with an appropriate restriction enzyme to produce an adenovirus restriction fragment representing a portion of the genome. The restriction fragment can be inserted into a cloning vehicle, such as a plasmid, and thereafter at least one transgene sequence (which may or may not encode a foreign protein) can be inserted into the adenovirus region with or without an operatively-linked eukaryotic transcriptional regulatory sequence. The recombinant expression cassette is contacted with the adenovirus genome and, through homologous recombination or other conventional genetic engineering methods, the desired recombinant is obtained. These DNA constructs can then undergo recombination in vitro or in vivo, with an adenovirus genome either before or after transformation or transfection of an appropriate host cell.

Deletion of adenovirus sequences, to provide a site for insertion of heterologous sequences or to provide additional capacity for insertion at a different site, or addition of sequences, such as an adenovirus E1 transcriptional control region, can be accomplished by methods well-known to those of skill in the art. For example, for adenovirus sequences cloned in a plasmid, digestion with one or more restriction enzymes (with at least one recognition sequence in the adenovirus insert) followed by ligation will, in some cases, result in deletion of sequences between the restriction enzyme recognition sites. Alternatively, digestion at a single restriction enzyme recognition site within the adenovirus insert, followed by exonuclease treatment, followed by ligation will result in deletion of adenovirus sequences adjacent to the restriction site. A plasmid containing one or more portions of the adenovirus genome with one or more deletions, constructed as described above, can be co-transfected into a bacterial cell along with a plasmid containing a full-length adenovirus genome to generate, by homologous recombination, a plasmid containing a adenovirus genome with a deletion at a specific site. Adenovirus virions containing the deletion (or addition) can then be obtained by transfection of appropriate mammalian cells, such as for example, mammalian cells comprising complementing adenovirus nucleotide sequences deleted from the adenovirus vector, with the plasmid containing an adenovirus genome with a deletion at a specific site.

Expression of an inserted sequence in a recombinant adenovirus vector will depend on the insertion site. Accordingly, insertion sites may be adjacent to and downstream (in the transcriptional sense) of adenovirus promoters. Locations of restriction enzyme recognition sequences downstream of adenovirus promoters, for use as insertion sites, can be easily determined by one of skill in the art from the adenovirus nucleotide sequences known in the art Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487-6500; Brennan et al. (1990) *Roux's Arch. Dev. Biol.* 199:89-96; and Kunkel et al. (1987) *Meth. Enzymology* 154:367-382) and PCR-mediated methods for insertion of longer sequences. See, for example, Zheng et al. (1994) *Virus Research* 31:163-186.

It is also possible to obtain expression of a transgene or heterologous sequence inserted at a site that is not downstream from an adenovirus promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned adenovirus genome; and the cloned adenovirus genome can be propagated as a plasmid. Infectious virus can be obtained by transfection of mammalian cells with the cloned adenovirus genome rescued from plasmid-containing cells.

Suitable host cells include any cell that will support recombination between an adenovirus genome and a plasmid containing adenovirus sequences, or between two or more plasmids, each containing adenovirus sequences. Recombination is generally performed in procaryotic cells, such as *E. coli*, while transfection of a plasmid containing a viral genome, to generate virus particles, is conducted in eukaryotic cells, preferably mammalian cells, most preferably porcine cell cultures. The growth of bacterial cell cultures, as well as culture and maintenance of eukaryotic cells and mammalian cell lines are procedures which are well-known to those of skill in the art. Accordingly, the present invention provides host cells comprising adenovirus vectors of the present invention.

In one example of the invention, a replication-defective recombinant adenovirus vector comprising one or more porcine adenovirus sequence(s) essential for encapsidation is used for expression of a transgene, such as for example, an antigen of a pathogen. In some examples, the replication-defective adenovirus vector lacks E1 region function. In other examples, the adenovirus vector lacks nucleic acid encoding multiple adenoviral genes. Transgene sequences can be inserted so as to replace deleted adenovirus region(s), and/or can be inserted at other sites in the genome. Replication-defective vectors with deletions in essential regions are grown in helper cell lines, which provide the deleted function. In other examples, a recombinant porcine adenovirus vector is deleted in a porcine adenovirus sequence(s) essential for encapsidation such that it is not capable of being encapsidated, and is grown in a helper cell line comprising porcine adenovirus sequence(s) essential for encapsidation.

Accordingly, the present invention provides recombinant helper cell lines, produced according to the present invention by constructing an expression cassette comprising an adenoviral region(s) necessary for complementation of adenovirus regions deleted in the adenovirus vector and transforming host cells therewith to provide complementing cell lines or cultures providing deleted functions. In some examples, the adenovirus vector lacks E1 regions essential for replication and the host cell is transformed with the adenovirus E1 region. The terms "complementing cell," "complementing cell line," "helper cell" and "helper cell line" are used interchangeably herein to denote a cell line that provides a viral function that is deficient in a deleted adenovirus vector. These recombinant complementing cell lines are capable of allowing a defective recombinant adenovirus to replicate and express one or more transgenes or fragments thereof. In other examples, a helper cell line comprises nucleic acid encoding porcine adenovirus sequences essential for encapsidation.

More generally, replication-defective recombinant adenovirus vectors, lacking one or more essential functions encoded by the adenovirus genome, can be propagated in appropriate complementing cell lines, wherein a particular complementing cell line provides a function or functions that is (are) lacking in a particular defective recombinant adenovirus vector. Complementing cell lines can provide viral functions through, for example, co-infection with a helper virus, or by integrating or otherwise maintaining in stable form a fragment of a viral genome encoding a particular viral function. In another embodiment of the invention, adenovirus function can be supplied (to provide a complementing cell line) by co-infection of cells with a virus which expresses the function that the vector lacks.

Uses of Adenovirus Vectors of the Present Invention

The use of adenoviral vectors in therapeutic and prophylactic methods is well documented. There are limitations to the use of adenovirus vectors, including for example limited insertion capacity of adenovirus vectors. Also, one problem that has arisen in the use of adenovirus vectors intended for immunization and gene delivery in mammals, such as humans, is the development of an immunological response (or in some cases, a pre-existing immunity) to the adenovirus, including to human adenovirus (HAVs). The expression of viral gene products from adenovirus vectors may contribute to the induction of a host immune response against transduced cells. Also, the presence of low levels of helper-independent vectors in the batches of helper-dependent human adenoviruses that are grown in complementing human cell lines has been reported. Fallaux et al. (1998) *Human Gene Therapy* 9:1909. This occurs as a result of recombination events between the viral DNA and the integrated adenoviral sequences present in the complementing cell line. Hehir et al. (1996) *J. Virol.* 70:8459-8467. This type of contamination constitutes a safety risk, which could result in the replication and spread of the virus.

The present invention provides adenovirus vector constructs that provide for increased insertion capacity. The present invention encompasses adenovirus vectors comprising one or more porcine adenovirus sequence(s) essential for encapsidation and deleted in one or more or multiple viral proteins, thereby allowing for increased insertion capacity. In some examples of the present invention, adenovirus vectors comprising porcine adenovirus sequences necessary for encapsidation can be used in therapeutic or prophylactic methods to decrease or minimize host immune response to the adenovirus proteins. The present invention encompasses porcine adenovirus vectors deleted in sequences essential for encapsidation, such that said vector is not capable of encapsidating, wherein a helper cell line provides the porcine adenovirus sequence(s) essential for encapsidation. In other examples, the present invention encompasses adenovirus vectors comprising one or more porcine adenovirus sequence(s) essential for encapsidation and non-porcine mammalian adenovirus sequences for use in treating or immunizing non-porcine mammals. In some examples, the adenovirus vector lacks one or more or multiple non-porcine mammalian viral proteins thereby providing an opportunity to minimize host immune response to adenovirus proteins. The present invention provides adenovirus vectors and methods for elimination of helper-independent adenoviruses in the batches of helper-dependent vectors by providing for the use of porcine adenovirus packaging domains in non-porcine mammalian adenovirus vectors, such as human adenovirus vectors.

The present invention encompasses PAV having a modification in one or more E1 transcriptional control regions. In some examples where it is desirable to produce a PAV capable of growing for a period of time (such as for vaccine purposes or gene delivery purposes), a PAV E1 transcriptional control region corresponding to the PAV3 region from about nucleotide 383 to about nucleotide 433 is deleted, wherein E1A expression is decreased and E1B expression is increased. In some examples, for production of a lytic PAV (such as for use in methods for treating or ameliorating the symptoms of cancer, such as in reducing tumor growth or targeted killing of cancer cells) increasing expression of E1A and/or decreasing expression of E1B (which has anti-apoptotic activity) is desirable. For production of a lytic PAV, one or more PAV E1 transcription control region(s) corresponding to the PAV3 region from about nucleotide 432 to about 449 and/or from about nucleotide 312 to about nucleotide 382 and/or from about nucleotide 252 to about 313 are added to the PAV to suppress E1B function. In another example, for production of a lytic PAV, one or more PAV E1 transcriptional control regions corresponding to the PAV3 region from nucleotide 382 to about 433 are added to the virus. Such deletions and/or additions of PAV E1 transcriptional control regions should not inhibit encapsidation of the PAV.

Also, the adenovirus vectors of the invention can be used for regulated expression of foreign polypeptides encoded by transgenes. Standard conditions of cell culture, such as are known by those of skill in the art, will allow for expression of recombinant polypeptides. They can be used, in addition, for regulated expression of RNAs encoded by heterologous nucleotide sequences, as in for example, antisense applications and expression of ribozymes. The adenovirus vectors of the present invention can be used for the expression of polypeptides in applications such as in vitro polypeptide production, vaccine production, nucleic acid immunization and gene delivery, for example. Polypeptides of therapeutic and/or diagnostic value include, but are not limited to, coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

In some examples of the present invention adenovirus vectors will comprise heterologous sequences encoding protective determinants of various pathogens of mammals, including for example humans, swine, sheep, or other mammals, for use in subunit vaccines and nucleic acid immunization. Representative human pathogen antigens include but are not limited to HIV virus antigens and hepatitis virus antigens. Representative swine pathogen antigens include, but are not limited to, pseudorabies virus (PRV) gp50; transmissible gastroenteritis virus (TGEV) S gene; porcine rotavirus VP7 and VP8 genes; genes of porcine respiratory and reproductive syndrome virus (PRRS), in particular ORFs 3, 4 and 5; genes of porcine epidemic diarrhea virus; genes of hog cholera virus; genes of porcine parvovirus; and genes of porcine influenza virus. Representative bovine pathogen antigens include bovine herpes virus type 1; bovine diarrhea virus; and bovine coronavirus.

Various foreign genes or nucleotide sequences or coding sequences (prokaryotic, and eukaryotic) can be inserted into an adenovirus vector, in accordance with the present invention, particularly to provide protection against a wide range of diseases.

A heterologous (i.e., foreign) nucleotide sequence can consist of one or more gene(s) of interest, and may have therapeutic or diagnostic value. In the context of the present invention, a gene of interest can code either for an antisense RNA, a ribozyme or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to be secreted and accordingly comprising a signal peptide, a chimeric protein originating from the fusion of sequences of diverse origins, or a mutant of a natural protein displaying improved or modified biological properties. Such a mutant can be obtained by deletion, substitution and/or addition of one or more nucleotide(s) of the gene coding for the natural protein, or any other type of change in the sequence encoding the natural protein, such as, for example, transposition or inversion.

Among genes of interest which are useful in the context of the present invention include but are not limited to genes coding for cytokines such as interferons and interleukins; genes encoding lymphokines; genes coding for membrane receptors such as the receptors recognized by pathogenic organisms (viruses, bacteria or parasites), including the HIV virus (human immunodeficiency virus); genes coding for coagulation factors such as factor VIII and factor IX; genes coding for dystrophins; genes coding for insulin; genes coding for proteins participating directly or indirectly in cellular ion channels, such as the CFTR (cystic fibrosis transmembrane conductance regulator) protein; genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene; genes coding for a protein inhibiting an enzyme activity, such as $\alpha_1$-antitrypsin or a viral protease inhibitor, for example; genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV; genes coding for antigenic epitopes in order to increase the host cell's immunity; genes coding for major histocompatibility complex classes I and II proteins, as well as the genes coding for the proteins which are inducers of these genes; genes coding for antibodies; genes coding for immunotoxins; genes encoding toxins; genes encoding growth factors or growth hormones; genes encoding cell receptors and their ligands; genes encoding tumor suppressors; genes coding for cellular enzymes or those produced by pathogenic organisms; and suicide genes. The HSV-1 TK suicide gene is mentioned as an example. This viral TK enzyme displays markedly greater affinity compared to the cellular TK enzyme for certain nucleoside analogues (such as acyclovir or gancyclovir). TK enzyme converts the analogues to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

In some cases the gene for a particular antigen can contain a large number of introns or can be from an RNA virus, in these cases a complementary DNA copy (cDNA) can be used. It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

Recombinant PAV vectors can be used to express antigens for provision of, for example, subunit vaccines. Antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). An antigenic polypeptide to be expressed by the virus systems of the present invention may contain full-length (or near full-length) sequences encoding antigens or shorter sequences that are antigenic (i.e., encode one or more epitopes). The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., a humoral (i.e. antibody-mediated), cell-mediated, and/or mucosal immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammal.

With the recombinant adenovirus vectors of the present invention, it is possible to elicit an immune response against disease antigens and/or provide protection against a wide variety of diseases affecting swine, cattle, humans and other mammals. Any of the recombinant antigenic determinants or recombinant live viruses of the invention can be formulated and used in substantially the same manner as described for the antigenic determinant vaccines or live vaccine vectors.

The present invention also includes compositions comprising a therapeutically effective amount of a recombinant adenovirus vector of the present invention, recombinant virus of the present invention or recombinant protein, prepared according to the methods of the invention, in combination with a pharmaceutically acceptable vehicle or carrier and/or an adjuvant. Such a composition can be prepared and dosages determined according to techniques that are well-known in the art. The pharmaceutical compositions of the invention can be administered by any known administration route including, but not limited to, systemically (for example, intravenously, intratracheally, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The vaccines of the invention carrying foreign genes or fragments can be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity (which plays an important role in protection against pathogens infecting the gastrointestinal tract) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to individuals the vaccine composition(s) of the present invention are within the skill of the art in view of the present disclosure. Those skilled in the art will select a concentration of the vaccine composition in a dose effective to elicit antibody, cell-mediated and/or mucosal immune responses to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1-10 ml. Preferably, the dosage in a single immunization will deliver from about 1 to about 500 micrograms of subunit antigen, more preferably about 5-10 to about 100-200 micrograms (e.g., 5-200 micrograms).

The timing of administration may also be important. For example, a primary inoculation preferably may be followed by subsequent booster inoculations, for example, several weeks to several months after the initial immunization, if needed. To insure sustained high levels of protection against disease, it may be helpful to re-administer booster immunizations at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between approximately $10^3$ pfu and $10^8$ pfu can be used. As with in vitro subunit vaccines, additional dosages can be given as determined by the clinical factors involved.

A problem that has beset the use of adenovirus vectors for immunization and gene delivery in humans is the rapid development of an immunological response (or indeed in some cases existing immunity) to human adenoviruses (HAVs). The recombinant adenovirus vectors of the present invention, are likely to be less immunogenic in humans and, for this and other reasons, will be useful either as a substitute for HAV vectors or in combination with HAV vectors. For example, an initial immunization with a HAV vector can be followed by booster immunizations using an adenovirus vector of the present invention; alternatively, initial immunization with a recombinant adenovirus vector of the present invention can be followed by booster immunizations with an HAV vector.

The invention also encompasses a method of treatment, according to which a therapeutically effective amount of an adenovirus vector comprising nucleic acid encoding a transgene, recombinant adenovirus expressing a transgene, or a host cell comprising such vectors or virus is administered to a mammalian subject requiring treatment.

When the heterologous sequences encode an antigenic polypeptide, adenovirus vectors comprising insertions of heterologous nucleotide sequences can be used to provide large quantities of antigen which are useful, in turn, for the preparation of antibodies. Methods for preparation of antibodies are well-known to those of skill in the art. Briefly, an animal (such as a rabbit) is given an initial subcutaneous injection of antigen plus Freund's complete adjuvant. One to two subsequent injections of antigen plus Freund's incomplete adjuvant are given at approximately 3 week intervals. Approximately 10 days after the final injection, serum is collected and tested for the presence of specific antibody by ELISA, Western Blot, immunoprecipitation, or any other immunological assay known to one of skill in the art.

Adenovirus E1 gene products transactivate many cellular genes; therefore, cell lines which constitutively express E1 proteins can express cellular polypeptides at a higher levels than other cell lines. The recombinant mammalian, particularly porcine, cell lines of the invention can be used to prepare and isolate polypeptides, including those such as (a) proteins associated with adenovirus E1A proteins: e.g. p300, retinoblastoma (Rb) protein, cyclins, kinases and the like; (b) proteins associated with adenovirus E1B protein: e.g. p53 and the like; growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IGF-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity) and the like; (f) other cellular proteins such as actins, collagens, fibronectins, integrins, phosphoproteins, proteoglycans, histones and the like, and (g) proteins involved in regulation of transcription such as TATA-box-binding protein (TBP), TBP-associated factors (TAFs), Sp1 binding protein and the like.

The invention also includes a method for delivering a gene to a mammal, such as a porcine, human or other mammal in need thereof, to control a gene deficiency. In one embodiment, the method comprises administering to said mammal a recombinant adenovirus of the present invention containing a heterologous nucleotide sequence encoding a non-defective form of said gene under conditions wherein the recombinant virus vector genome is incorporated into said mammalian genome or is maintained independently and extrachromosomally to provide expression of the required gene in the target organ or tissue. In some examples, the adenovirus vector is replication-competent and in other examples, is replication-defective. These kinds of techniques are currently being used by those of skill in the art to replace a defective gene or portion thereof. Examples of foreign genes, such as transgenes, heterologous nucleotide sequences, or portions thereof that can be incorporated for use in gene therapy include, but are not limited to, cystic fibrosis transmembrane conductance regulator gene, human minidystrophin gene, alpha-1-antitrypsin gene and the like.

In particular, the practice of the present invention in regard to gene delivery in humans is intended for the prevention and/or treatment of symptoms diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection) and the like. For the purposes of the present invention, the vectors, cells and viral particles prepared by the methods of the invention may be introduced into a subject either ex vivo, (i.e., in a cell or cells removed from the patient) or directly in vivo into the body to be treated. In some examples, the host cell is a human cell and, may be a lung, fibroblast, muscle, liver or lymphocytic cell or a cell of the hematopoietic lineage.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

EXAMPLES

Example 1

Materials and Methods
Cells and Viruses

VIDO R1 cells (Reddy et al., 1999, *J. Gen Virol.* 80:2909-2916) are porcine retinal cells expressing human E1 function and are deposited with the ATCC as accession number PTA-155) were grown and maintained in Eagle's minimum essential medium (MEM) supplemented with 10% fetal bovine serum (FBS). All the mutant porcine adenovirus 3 (PAV3) and wild-type PAV3 (strain 6618) were propagated and titrated in VIDO R1 cells. Wild-type PAV3 genomic DNA was extracted from CsCl equilibrium centrifugation-purified virions.

PCR Amplification

Plasmid PAV3.Eco47-3 containing the both ends of PAV3 genome was used as templates in PCR. The following conditions were used for PCR in a total volume of 50 ul: 0.5 g of template DNA, 1×PCR buffer (10 mM KCl, 10 mM $(NH_4)_2SO_4$, 20 mM Tris-Cl (pH 8.75), 2 mM $MgSO_4$, 0.1% Triton®X-100, 0.1 mg/ml BSA) (Stratagene), 0.4 mM dNTPs, 10 pmol of each primer, 2.0 U of cloned pfu DNA polymerase (Stratagene). The cycling conditions were: 94° C. for 70 s to denaturate the DNA, followed by 30 cycles consisting of 94° C. for 40 s, 50° C. for 40 s, 72° C. for 40 s, and finally, renaturation at 72° C. for 2 min. The products of PCR were loaded onto a 2% agarose gel and visualized by ethidium bromide (EtBr) staining. The primers used in this study are shown in Table 3.

Construction of Recombinant Plasmids

DNA fragments were developed by PCR and a unique Mfe I cleavage site was introduced into these fragments. DNA fragments were digested with Mfe I and BamH I or Mfe I and EcoR V, respectively, and then were inserted into BamH I/EcoR V site of plasmid PAV3.Eco47-3 by a three way ligation to create the recombinant transfer plasmids containing deletion mutations between left-end ITR and ATG codon of early region E1A gene of PAV3.

To construct the recombinant plasmids containing deletion mutations between right end ITR and early region E4 gene of PAV 3, Hpa I and Pac I cleavage sites were utilized in plasmid PAV3.Eco47-3.

The full-length plasmids containing the full-length genome of PAV3 with deletion mutations in the putative packaging domain were generated by homologous recombination in *E. coli* BJ5183 (2) between Eco47-3-linearized recombinant transfer plasmids and the genomic DNA from wild-type PAV3. Full-length plasmids were mini-prepared and then were transformed into *E. coli* DH5α for large-scale plasmid preparation. These plasmids were characterised by restriction endonuclease analysis. The endpoints of deletion mutations introduced into plasmids were determined by nucleotide sequence analysis.

Isolation of Recombinant PAV3

VIDO R1 cell monolayers were seeded in a 35 mm dish in diameter and were transfected with 5 μg of PacI-digested full-length plasmid DNA using the Lipofectin methods according to the instruction of manufacturer (Gibco BRL). After 10 to 15 days of incubation at 37° C., the transfected cells were collected and freezing-thawing for three times. The lysates were used to infect the freshly prepared VIDO R1 cells until cytopathic effect appeared. Finally, the recombinant viruses were characterized by PCR and restriction analysis and then expanded and titrated on VIDO R1 cells.

Determination of Virus Yields and Packaging Efficiency

All viral infections were performed at a multiplicity of infection of 5 plaque forming units (PFU) per cell at 37° C. for 1 h, and then the fresh medium was added. For the determination of viral yield in single-virus infections, infected VIDO R1 cells were harvested 48 h after infection and then lysed by three cycles of freezing and thawing, and infectious virus yields in cleared lysates were determined by plaque assay on VIDO R1 cells. The data presented for virus yields from single infections represent the averages of three independent experiments.

Packaging efficiency of the mutant viruses was determined in a coinfection of VIDO R1 cells with both mutant and wild type PAV3, according to the method described by Graeble et al (1990, *J. Virol.* 64:2047-2056 and 1992, *J. Virol.* 66:723-731) with a few modifications. VIDO R1 cells were infected with 5 PFU of each virus per cell as described above. Forty-eight hours post-infection, one-half of the cells were used to isolate high-molecular-weight DNA, and the other half of the cells were used to prepare viral DNA from virions. For the isolation of infected cell high-molecular-weight DNA, the cells were lysed by the addition of Nonidet P-40 to 0.4%, and then digested with proteinase K at 50° C. for several hours. The high-molecular-weight DNA was isolated as described by Sambrooke et al., 1989, Molecular Cloning, 2$^{nd}$ ed. Cold Spring Harbor Laboratory Press, Cold Spring Harbor, N.Y.). For the isolation of viral DNA from virions, infected cells were precipitated and suspended in lysis buffer (20 mM Tris-Cl[pH8.0], 0.2% deoxycholate, 10% ethanol). After incubation for 60 min at room temperature, the lysate was cleared at 10,000×g for 30 min. The supernatant was adjusted to 2 mM CaCl$_2$ and 2 mM MgCl2, and was digested with 40 μg of RNase A per ml and 10 μg of DNase I per ml at 37° C. for 30 min. The reaction was stopped by the addition of EDTA and EGTA to a final concentration of 50 mM each. Virus particles were lysed by the addition of Sarkosyl to 0.5%, and the samples were digested with 1 mg of proteinase K per ml at 50° C. for 1 h to several hours. After two times of phenol and one time of chloroform extraction, the viral DNA was precipitated with ethanol. DNAs isolated from nuclei or virions were digested with Mfe I and EcoR V, and then analysed by Southern hybridization.

Southern Hybridization

MfeI and EcoR V-digested DNAs were run on 1.5% agarose gel to separate the DNA fragments and then transferred onto Gene Screen Plus hybridization transfer membrane (Perkin Elmer Life Science Ico. Boston, Mass. 02118-2512) by high salt capillary transfer method according to the instruction of manufacturer. The DNA fragment corresponding to that between nucleotides (nt) 531 and 844 was developed by PCR with primers P2 and P20. It was labeled with $^{32}$P-dCTP by the random primer method using Random Primers DNA labeling system (Gibco. BRL), and was used as probes in Southern hybridization analysis. The blots were prehybridized in ULTRAhyb ultrasensitive hybridization buffer (Ambion® RNA company) at 42° C. for 30 min, and then $^{32}$P-labeled probes were added. Hybridization was performed at 42° C. overnight. After extensively washing with 0.1×SSC and 0.1% SDS, the blots were exposed to X-ray film (Koda) without an intensifying screen. The bands in autoradiograms were scanned and their relative intensities were determined and analysed by Computing Densitometer using Alphamager program. The data presented for packaging efficiency based on coinfection experiments represent the averages of three independent experiments.

Example 2

Analysis of the PAV3 Genomic Sequences

The inverted terminal repeat (ITR) of PAV3 is 144 bp in length (Reddy et al., 1998, *Virology*, 251:414-426). Based on the consensus sequences of cis-acting packaging motif of human adenovirus 5,5'-TTTGN8CG-3' (Schmid et al., 1997, *J. Virol.* 71:3375), the PAV3 genome was searched for identification of putative motifs required for packaging PAV3 genomic DNA into preformed empty capsids in the two regions of viral genome. One is between left ITR and E1A gene, another is located between right ITR and E4 gene. However, we could not find any motif that showed perfect homology with the consensus packaging motifs of HAV5 between left ITR and E1A gene of PAV3. There are at least six AT-rich motifs in this region, and one of them is the TATA box of E1A gene promoter of PAV3. There are two AT-rich motifs containing TTTG sequences between right ITR and PAV3 E4 gene. To characterize which of them could function in cis as packaging motifs for PAV3, deletion mutations were introduced into intact viral genome to delete these candidate motifs in single fashion or in combinations.

Construction and Characterization of Mutant Viruses

Deletion mutations in PAV3 genome were initially constructed in a recombinant transfer plasmid PAV3.Eco47-3 by dropping DNA sequences located between two PCR DNA fragments through insertion of two PCR DNA fragments into BamH I/EcoRV site of PAV3.Eco47-3 in a three way ligation. The deletion mutations were then rebuilt into intact viral genome by homologous recombination between wild-type PAV3 genomic DNA and Eco47-3-linearized recombinant shuttle plasmids in *E. coli* BJ5183 cells. The resulting plasmids were digested with Pac I and then were used to transfect VIDO R1 cells to rescue the viable virus containing deletion mutations. The mutant PAV3 was characterized by PCR with primers P2 and PSR32.

We noticed that most of deletion mutations in this study were located between nucleotide position (nt) 151 and 531, which was also the regulatory region of PAV3 E1A transcription unit (6). The mutation in this region could probably affect the expression of E1A gene and then resulted in the changes in viral growth of mutant PAV3, or even make the virus nonviable. Some evidences showed that E1 gene products from human adenovirus type 5 could complement the defect of PAV3 E1 gene expression. VIDO R1 cells express human adenovirus E1 gene, so that this cell line was chosen and used throughout this study.

Two independent assays were used to analyze the efficiency of packaging with the viral recombinants. First, the mutant viruses were used in single infections on VIDO R1 cells, and the infectious virus yields obtained after 2 days were determined by a plaque assay. As mentioned above, deletion mutations may affect the E1 gene expression and then affect the growth of mutant viruses although human E1 gene products can complement the defect of PAV3 E1 gene expression. To completely exclude this possible effect, another assay was employed, in which VIDO R1 cells were coinfected with wild-type and mutant PAV3 at the same time at the same multiplicities of infection. At 2 days after infection, the nuclei high-molecular-weight DNA and viral DNA from virion particles were prepared. The coinfecting viral genomes can be distinguished by double digestion with MfeI and EcoRV, and then Southern hybridization analysis.

Example 3

Packaging Domain of PAV3 is Located at the Left End of Viral Genome

In the first set of mutant viruses (FIGS. 4 and 5), the deletion mutations were targeted at different regions on PAV3 genome. The data in single infection in VIDO R1 cells showed that deletion in regions between nt 151 and 213, 212 and 254, 252 and 313, 312 and 383, 432 and 449, 461 and 497, reduced the growth level of PAV3 by 2 to 7 fold. However, in coinfection assays, deletions between nt 151 and 213, 461 and 497, had no effect on the packaging abilities of viruses. Deletion between nt 495 and 531 resulted in reduction in packaging ability. In single infection, mutant viruses containing deletions between nt 33911 and 33949 at the right end of viral genome grew as well as wild-type virus, so that we did not further test the packaging ability with these recombinants in coinfection assay. These results suggested that the packaging domains of PAV3 were located at the left end of viral genome, but not right end, and were possibly functionally redundant as described for human adenovirus type 5 (Grable et al., 1990, J. Virol. and Grable et al., 1992, J. Virol., supra and Schmid et al. 1997, supra). They appeared to overlap the promoter region of E1A gene.

To further define the packaging domain of PAV3, we constructed two other sets of mutant viruses. One set of mutant viruses contains deletions which progress from a common site at nt 151 towards the downstream border of the packaging domain. The data obtained with these virus mutants are shown in FIGS. 6 and 7. Mutant carrying deletion between nt 151 and 254, has a reduced growth level in single infection and a reduced packaging ability by 2 fold in coinfection. On the basis of this mutant, the additional deletions between nt 254 and 313, 313 and 383, resulted in a two-to five and eight fold reduction in viral yields in single infection, and a two-to three and seven fold reduction in packaging ability in coinfections. These results suggested that there are packaging motifs located between nt 254 and 313, 313 and 383. On the basis of deletion between nt 151 and 383, the further deletions between nt 383 and 497 did not result in the further reduction in viral growth in single infection and in packaging ability in coinfection. Surprisingly, the mutant with a deletion between 151 and 449 showed the lowest growth in VIDO R1 cells in single infection. The reasons for this phenomenon remain unclear. Deletion between nt 151 and 531 made the virus nonviable. This suggested that there would be a packaging motif between nt 497 and 531, which is also critical to the viral packaging, and this motif alone can support the virus packaging. This motif probably represented the downstream border packaging motif.

Another set of virus mutants contain deletions which progress from a common site at nt 531 towards the upstream border of the packaging domain (FIGS. 8 and 9). When a deletion was located between nt 212 and 531 (SEQ ID NO:414), virus was not obtained. The results suggested that the packaging domain of PAV3 probably existed between nt 212 and 531 (SEQ ID NO:414). The existence of DNA sequences between nt 212 and 252 made the virus viable and suggested that there should be a packaging motif in this region, which was probably the upstream border packaging motif of PAV3. The PAV3-252/531 showed a lower level of growth in VIDO R1 cells in single infection and a lower packaging ability in coinfection when compared with mutant PAV3-151/497 (FIG. 6). The result showed that the downstream border packaging motif between nt 474 and 497 can provide the stronger packaging ability to PAV3 than the upstream border packaging motif between nt 212 and 252. From PAV3-252/531 to PAV3-382/531, the sequential addition of DNA sequences between nt 252 and 382 resulted in the increase in both the viral growth level and packaging ability. Results suggested that there would be two packaging motifs between nt 252 and 382. Pav3-382/531 has the same growth property and packaging ability as compared with PAV3-432/531. The addition of DNA sequences between nt 382 and 432 has no effect on the viral packaging. The further addition of DNA sequences between nt 432 and 447 made both the viral growth and packaging ability increase. This suggested that the AT-rich motif between nt 432 and 447 could function as a packaging motif.

The TATA box for E1A gene of PAV3 is located between nt 447 and 474. As shown in FIG. 4, the single deletion of this region had no obvious effect on the viral growth in VIDO R1 cells which can complement the defect in PAV3 E1A gene expression due to expression of human adenovirus 5 E1 gene products. However, in coinfection assay, we detected the decrease in the packaging ability by 2 fold. The data from this set of mutants also showed that addition of TATA box sequences in case of PAV3-461/531 made the viral packaging ability increase slightly as compared with PAV3-447/531. These results suggested that PAV3 used these sequences as a packaging motif.

As described above (FIGS. 6 and 7), the mutant virus PAV3-151/449 has a similar packaging ability as compared with PAV3-151/433 and PAV3-151/474. However, this virus showed a reduction in growth in VIDO R1 cells by 20 fold. To confirm these data, we constructed another set of mutants which have the deletions progressing from a common site at nt 449 towards the upstream border of packaging domain (FIGS. 10 and 11). From PAV3-212/449 to PAV3-382/449, the sequential addition of DNA sequences between nt 212 and 252, 252 and 312, and between 312 and 382, the packaging abilities of viruses increased correspondingly in a coinfection assay. These data showed that the trend is in good agreement with that described above (FIGS. 8 and 9), and confirmed that there were packaging motifs in these three regions. However, PAV3-212/449 and PAV3-252/449 still remained a significant reduction in growth on VIDO R1 cells in a single infection assay when compared with their reduction in packaging ability in a coinfection assay. The addition of DNA sequences between nt 252 and 312 enhanced significantly the viral growth in VIDO R1 cells, although it made the viral packaging ability increase slightly. These data suggested that DNA sequences between nt 252 and 312 maybe have other unknown functions in viral life cycle.

In conclusion, the packaging domain of PAV3 is located between nt 212 and 531 (SEQ ID NO:414) on the left end of viral genome. There are at least six AT-rich motifs which can provide the packaging ability to PAV3. They overlap the promoter region of E1A gene of the virus. Packaging motifs of PAV3 have an AT-rich sequence followed by GC-rich region. They are functionally redundant and show an importance hierarchy. Some of them alone can support the viral packaging and make virus viable.

TABLE 3

Primers used in this study. The restriction endonuclease cleavage sites are underlined. Numbers indicate the nucleotide position relative to the left terminus of PAV3 genome. PAV3 nucleotide sequences are indicated in boldface type.

| | | |
|---|---|---|
| P1: | 5'-CGT CTT CAA GGA TCC TTA-3' (SEQ ID NO: 21) | (sense, BamH I) |
| P2: | 5'-CGC GCT GAT ATC CTC CTC-3' (SEQ ID NO: 22) | (anti sense, EcoR V, 827-844) |
| P3: | 5'-CCG CAA TTG GTC ATC ACA CGT CAT TTT C-3' (SEQ ID NO: 23) | (antisense, Mfe I, 133-151) |
| P4: | 5'-CCG CAA TTG GGG GCG GGG CCG AGC GGC-3' (SEQ ID NO: 24) | (sense, Mfe I, 213-230) |
| P5: | 5'-CCG CAA TTG GCG GAG GAC CGC CCC AGG-3' (SEQ ID NO: 25) | (antisense, Mfe I, 195-212) |
| P6: | 5'-CCG CAA TTG ATA CCG CGG GAT TTT GT-3' (SEQ ID NO: 26) | (sense, Mfe I, 255-271) |
| P7: | 5'-CCG CAA TTG CTC CAC CTG TGC GGG AAT-3' (SEQ ID NO: 27) | (antisense, Mfe I, 235-252) |
| P8: | 5'-CCG CAA TTG CAC CAC ACG TCC GCG G-3' (SEQ ID NO: 28) | (sense, Mfe I, 313-328) |
| P9: | 5'-CCG CAA TTG CGG AAG TGC CAC ACC GGA-3' (SEQ ID NO: 29) | (antisense, Mfe I, 295-312) |
| P10: | 5'-CCG CAA TTG TCG CGC TGA GAG GTC CGC G-3' (SEQ ID NO: 30) | (sense, Mfe I, 383-401) |
| P11: | 5'-CCG CAA TTG AGG ACA CCC CGC TCA GGT-3' (SEQ ID NO: 31) | (antisense, Mfe I, 365-382) |
| P12: | 5'-CCG CAA TTG TTT TTT CCC CTC AGT GTA TA-3' (SEQ ID NO: 32) | (sense, Mfe I, 433-452) |
| P13: | 5'-CCG CAA TTG TAC ACC CAC ACA CGT CAT-3' (SEQ ID NO: 33) | (antisense, Mfe I, 415-432) |
| P14: | 5'-CCG CAA TTG TAT ATA GTC CGC GCA-3' (SEQ ID NO: 34) | (sense, Mfe I, 449-463) |
| P15: | 5'-CCG CAA TTG ACT GAG GGG AAA AAA TAC-3' (SEQ ID NO: 35) | (antisense, Mfe I, 430-447) |
| P16: | 5'-CCG CAA TTG GTC ACT ACT CTT GAG TCC-3' (SEQ ID NO: 36) | (sense, Mfe I, 474-491) |
| P17: | 5'-CCG CAA TTG CGC GGA CTA TAT ACA CTG-3' (SEQ ID NO: 37) | (antisense, Mfe I, 444-461) |
| P18: | 5'-CCG CAA TTG GAG TAG AGT TTT CTC TCA-3' (SEQ ID NO: 38) | (sense, Mfe I, 497-514) |
| P19: | 5'-CCG CAA TTG CTT CGG ACT CAA GAG TAG-3' (SEQ ID NO: 39) | (antisense, Mfe I, 478-495) |
| P20: | 5'-CCG CAA TTG ACA TGG CGA ACA GAC TTC-3' (SEQ ID NO: 40) | (sense, Mfe I, 531-548) |
| PR1: | 5'-CCG CCT CCG CGT TAA CGA TTA ACC-3' (SEQ ID NO: 41) | (sense, Hpa I, 33838-33861) |
| PR2: | 5'-AGC TTT TAA TTA ACA TCA TC-3' (SEQ ID NO: 42) | (antisense, Pac I, 34088-34094) |

TABLE 3-continued Primers used in this study. The restriction endonuclease cleavage sites
are underlined. Numbers indicate the nucleotide position relative to the
left terminus of PAV3 genome. PAV3 nucleotide sequences are indicated
in boldface type.

| | | | |
|---|---|---|---|
| PR3: | 5'-CCG CAA TTG CGC AGG TCG CGG CGG AGC-3' (SEQ ID NO: 43) | | (antisense, Mfe I, 33894-33911) |
| PR4: | 5'-CCG CAA TTG CCT CGG ACT TTG ACC GT-3' (SEQ ID NO: 44) | | (sense, Mfe I, 33926-33942) |
| PR5: | 5'-CCG CAA TTG GGC GGG GTC AAA GTC GCA-3' (SEQ ID NO: 45) | | (antisense, Mfe I, 33908-33926) |
| PR6: | 5'-CCG CAATTG CCA CGT CAT TTT CCC A-3' (SEQ ID NO: 46) | | (sense, Mfe I, 33949-33965) |
| PSR32: | 5'-CGG CGG GAT CCT TAA TTA ACA TCA TCA ATA ATA TAC CGC ACA CTT TT-3' (SEQ ID NO: 47) | | (1-18) |

Example 4

Identification of Regulatory Elements of PAV
Materials and Methods
Viruses and Cells The mutant and wild-type PAV-3 Clarke et al. (1967, *Arch. Ges. Virusforsch.* 21:91-97); Derbyshire et al. (1975, *J. Comp. Pathol.* 85:437-443) (strain 6618) were cultivated in swine testis (ST) and VIDO R1 cells (U.S. Pat. No. 6,492,343). VIDO R1 is a transformed fetal porcine retina cell (FPRC) line expressing the E1A and E1B proteins of human adenovirus type 5 (HAV-5) under the control of mouse phosphoglycerate kinase gene promoter. The cells were grown and maintained in Eagle's minimum essential medium (MEM) supplemented with 10% heat-inactivated fetal bovine serum (FBS) and antibiotics. The viral titres were determined by plaque assay on VIDO R1 cells.

Construction and Propagation of Virus Mutants

Construction and propagation of PAV-3 mutants are described below. Briefly, deletions in PAV-3 E1A transcriptional control region between the end of left inverted terminal repeat (ITR) and the start ATG codon of E1A gene were initially constructed in a plasmid pPAV3.Eco47-3 using PCR method. Plasmid pPAV3.Eco47-3 contains both the left 6.4% (nt 1-2192) and the right 7.6% end (nt 31499-34094) of the viral genome. DNA sequences located between two PCR products were deleted through insertion of two PCR products into BamHI-EcoRV site of pPAV3.Eco47-3 in a three-way ligation. Deletions were then rebuilt into intact viral genomes using the *E. coli* BJ5183 homologous recombination system Chartier et al. (1996, *J. Virol.* 70:4805-4810) to create the deletion mutation-containing full-length plasmids. The exact endpoints of each deletion were determined by nucleotide sequence analysis. Virus mutants were rescued by transfection of PacI-digested individual full-length plasmids into VIDO R1 cells using Lipofectin methods according to the instructions of manufacturer (Gibco BRL). Mutant viruses were plaque-purified and characterized by PCR and restriction enzyme analysis. Virus stocks were prepared in VIDO R1 cells, titrated by plaque assay, and then preserved in −80° C.

DNA Probes.

[$^{32}$P]-dCTP labeled DNA probes used in Northern and Southern hybridizations were generated by using Random primers DNA labeling system according to the instructions of manufacturer (Invitrogen). PAV-3 DNA fragments used for preparation of probes are summarized in Table 4.

Polymerase-Chain Reaction (PCR).

The wild-type PAV-3 genomic DNAs were used as templates in PCR amplifications. The following conditions were used for PCR in a total volume of 50 µl: 0.5 µg of template DNA, 1×PCR buffer (10 mM KCl, 10 mM $(NH_4)_2SO_4$, 20 mM Tris-Cl (pH 8.75), 2 mM $MgSO_4$, 0.1% Triton®X-100, 0.1 mg/ml BSA) (Stratagene), 0.4 mM dNTPs, 10 pmol of each primer, 2.0 U of cloned pfu DNA polymerase (Stratagene). The cycling conditions were: 94° C. for 2 min to denature the DNA, followed by 35 cycles consisting of 94° C. for 40 s, 50° C. for 40 s, 72° C. for 40 s, and finally, extension at 72° C. for 2 min.

RNA Preparation and Northern Blot

To prepare RNAs, ST cells were infected with virus at a multiplicity of infection (MOI) of 40 plaque-forming units (PFU) per cell for 2 h at 37° C. and incubated in MEM containing 10% heat-inactivated FBS and 125 µg/ml AraC. The infected cells were harvested at 7 h postinfection and the total RNA was isolated with TRIzol reagent (Gibco BRL) according to the manufacturer's instructions.

For Northern blot analysis, 20 µg of total RNAs were separated in denaturing 1% agarose-2.2 M formaldehyde gels by electrophoresis for 3 h, and then were blotted onto the Gene Screen Plus hybridization transfer membrane (Perkin Elmer Life Science Inc.) according to the manufacturer's instruction. The membranes were baked for 2 h at 80° C. in a vacuum oven and then soaked in hybridization buffer [UL-TRAhyb ultrasensitive hybridization solution (Ambion RNA company)] for 0.5 h at 42° C. Northern hybridization was performed with hybridization buffer containing [$^{32}$P]-labeled DNA probes synthesized by using Random primers DNA labeling system (Invitrogen). After hybridization at 42° C. overnight, the membranes were washed twice with 2×SSC and 0.1% SDS at room temperature, followed by washing twice with 0.1×SSC and 0.1% SDS at 50° C. for 30 min. Finally, the membranes were dried and exposed to X-ray film (Kodak). The RNA bands on the autoradiograms were quantitated using computer-assisted Alphamager program.

DNA Preparation and Southern Blot

To prepare DNA, ST and VIDO R1 cells were infected with wild-type or mutant viruses at a MOI of 5 PFU per cell for 2 hr at 37° C. In coinfection experiments, ST cells were infected with both wild-type and mutant PAV-3 at a MOI of 5 PFU per cell (each virus). The infected cells were harvested at 9, 16, 23, and 30 h postinfection, and resuspended in extraction buffer (10 mM Tris-Cl, 0.1 M EDTA, 20 µg RNase per ml, 0.5% SDS, pH8.0) containing proteinase K at the concentration of 100 µg per ml. After incubation for 2 h at 50° C., phenol and chloroform extractions were performed. Finally, the DNAs were precipitated by ethanol and dissolved in TE buffer (10 mM Tris-Cl, 1 mM EDTA, pH 8.0)

In single virus infection, the DNA was digested with HindIII. In coinfection experiments, the DNA was digested with MfeI and KpnI to distinguish the coinfecting wild-type and mutant viruses. Southern blot analysis was performed using a standard procedure. Sambrook et al. (1989. *Molecular cloning: a laboratory manual*, 2nd ed. Cold Spring Harbor Laboratory Press. Cold Spring Harbor, N.Y.). The relative intensities of the DNA bands on the autoradiograms were measured by computer-assisted Alphamager program.

Viral Growth Curves

To determine the growth kinetics of virus mutants, VIDO R1 and ST sells were infected with wild-type or mutant viruses at a MOI of 5 PFU per cell for 2 h at 37° C. After washing with phosphate-buffered saline (PBS), MEM containing 10% FBS was added. Infected cells were harvested at indicated times postinfection. Viral progeny was released into medium by freezing-thawing infected cells three times. The titers of infectious viral progeny were determined by plaque assay on VIDO R1 cells and expressed as plaque-forming unit (PFU) per ml.

Experiments

Construction and Propagation of Virus Mutants

Initially, deletions in the PAV-3 E1A transcriptional control region were constructed in a transfer plasmid pPAV3.Eco47-3 containing the 2192 bp left end fragment and 2595 bp right end fragment of PAV-3 genome Reddy et al., (1998, *Virus Res.* 58:97-106). with the aid of PCR by deleting DNA sequences located between two PCR products. A select group of deletions (FIG. 13A) were introduced into intact viral genome by homologous recombination between individual deletion mutation-containing transfer plasmid and the wild-type PAV-3 genomic DNA in *E. coli* BJ5183 cells. Chartier et al. (1996, *J. Virol.* 70:4805-4810). The exact site of each deletion was determined by nucleotide sequences analysis. Resulting plasmid DNA containing the full-length PAV-3 genome with the deletions in the desired region were digested with PacI and transfected individually into VIDO R1 cells to rescue the viable PAV-3 mutants.

The mutations cover a 323 bp region from the end of PAV-3 left ITR through most of the 5'-noncoding region of E1A gene (FIG. 13A). The construction and characterization of PAV-3 mutants designated as Pav110 (Pav3-151/213), Pav26 (Pav3-212/254), Pav37 (Pav3-252/313), Pav48 (Pav3-312/383), Pav59 (Pav3-382/433), Pav1413 (Pav3-432/449), Pav1615 (Pav3-447/474), Pav16 (Pav3-151/254), and Pav514 (Pav3-382/449). In addition, three new virus mutants designated as Pav27 (nt 212-313), Pav49 (nt 312-433), and Pav516 (nt 382-474) (FIG. 13A) were constructed with the mutant virus construction procedure by using primer pairs P1-P5 and P2-P8, P1-P9 and P2-P12, and P1-P11 and P2-P16, respectively. The identity of virus mutant was confirmed by restriction enzyme analysis, PCR analysis and DNA sequence analysis of mutant viral DNA. To verify that each of the mutant stocks was titrated accurately so that we use the same viral input in subsequent viral infection for each virus mutant, ST cells were infected with the virus mutants, and viral DNA present in the nucleus at 6 h after infection was isolated and analyzed by Southern hybridization. Each of the mutant viruses displayed comparable levels of nuclear DNA at early times after infection.

A Regulatory Element Augments E1A Transcription But Represses the E1B

Figures 14A, 14B, 14C, 14D, 14E, 14F:
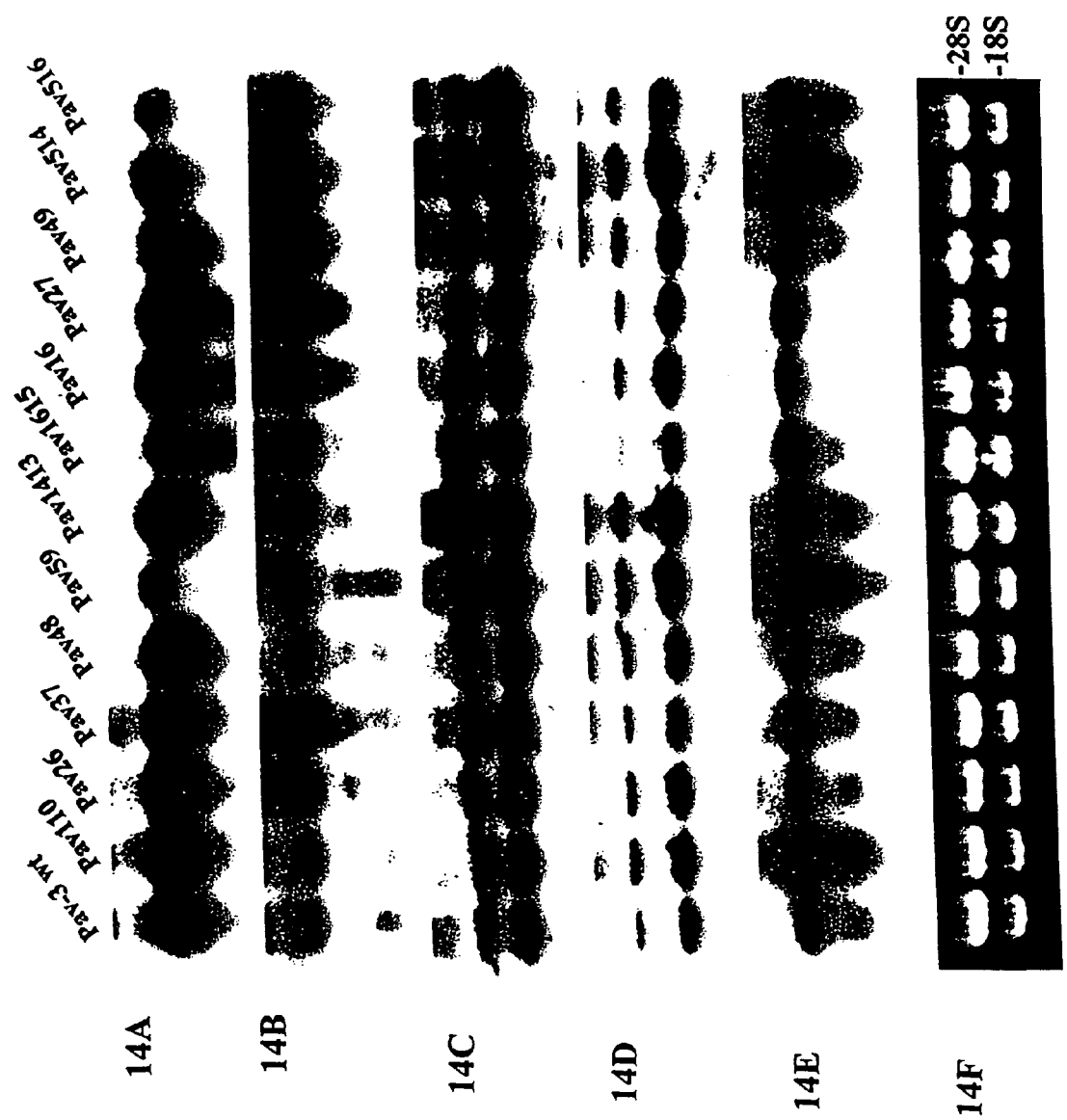

To determine the effect of the deletions on the E1A transcription, ST cells were infected with wild-type or mutant viruses at a MOI of 40 PFU per cell. The cytoplasmic total RNA was isolated early (7 h) postinfection and the steady-state levels of E1A mRNAs were determined by Northern hybridization using [$^{32}$P]-labeled E1A-specific (nt 531-844) DNA probe. The wild-type PAV-3 was included as a control throughout the study. As shown in FIG. 14A, the deletions between nt 151 and 383 (Pav110, Pav26, Pav37, and Pav48) had no effect on the steady-state levels of E1A mRNAs when compared with that of wild-type virus. In contrast, a deletion between nt 382 and 433 (Pav59) resulted in significant reduction in the level of E1A mRNA. The results indicated that the sequences between nt 382 and 433 contain a cis-acting regulatory element(s) that could augment the transcription of E1A. The TATA box located between nt 449 and 454 Reddy et al. (1998, *Virus Res.* 58:97-106) is one core promoter element of PAV-3 E1A and was deleted in Pav1615 (nt 447-474). As expected, Pav16115 displayed a dramatic reduction in E1A transcription. The reduction in the E1A transcription was also evident with the mutant Pav514 and Pav516, which carried the deletions between nt 382 and 449, and nt 382 and 474, respectively. The results confirmed the existence of a regulatory element, which is located upstream of TATA box of E1A promoter, and critical for normal transcription of E1A genes in virus-infected cells.

The E1B transcription unit of PAV-3 lies directly downstream of the E1A unit Reddy et al. (1998, *Virus Res.* 58:97-106). It was reported previously that the E1A enhancer element enhances in cis the expression of E1B in human adenovirus type 5 (HAV-5). Hearing et al. (1983, *Cell.* 33: 695-703). To test if the transcriptional regulatory element of PAV-3 E1A could also modulate the transcription of E1B, the steady-state level of E1B mRNAs was assayed with Northern hybridization using a [$^{32}$P]-labeled probe (nt 1411-3077). As shown in FIG. 14B, deletion between nt 447 and 474 (Pav1615) resulted in slight reduction in the level of E1B mRNA than that of wild-type virus. In contrast, deletion between nt 382 and 433 (Pav59) caused a slight increase in the level of E1B mRNAs. However, both mutant viruses displayed the significant reduction in transcription of E1A. The results demonstrated that the deletion of TATA box of E1A promoter has the same effects on the transcription of E1A and E1B, but the deletion of regulatory element has opposite effects on the transcription of E1A and E1B. This suggested that the regulatory element between nt 382 and 433 showed two-faced functions: enhances the E1A and represses the E1B.

Deletion between nt 432 and 449 (Pav1413) has no effects on E1A transcription, but increased the level of E1B mRNAs. This deletion is located between regulatory element and TATA box of E1A promoter and contains a potential cis-acting packaging motif. It appears that the upstream activation sequences (UAS) of E1A overlap at least in part with the upstream repression sequences (URS) of E1B. As expected, the increase in the level of E1B mRNAs and decrease in the level of E1A mRNAs were evident with the mutant viruses Pav514 (nt 382-449) and Pav516 (nt 382-474), which carried the deletions containing the regulatory element. The results suggested that the influences of deletion mutations in Pav59, Pav514, and Pav516 on the transcription of E1B are independent of the E1A and are cis-acting effects. A deletion between nt 252 and 313 (Pav37) did not affect the transcription of E1A, it caused an increased level of E1B mRNAs.

The transcription of other early genes of adenovirus including E2, E3, and E4 is controlled by E1 gene products. Berk et al. (1979, *Cell*. 17:935-944), Jones et al. (1979, *Proc. Natl. Acad. Sci. USA*. 76:3665-3669). In addition, an enhancer element in the transcriptional control region of E1A regulates directly the transcription of all early genes in HAV-5. Hearing et al. (1986, *Cell*. 45:229-236). Therefore, we tested the effects of the deletion mutations in PAV-3 E1A transcriptional control region on the transcription from other early regions. The cytoplasmic RNAs isolated early (7 h) postinfection were probed in Northern hybridization with [$^{32}$P]-labeled E2A (nt 22667-23736)-, E3 (nt 27587-29011)-, and E4 (nt 32504-33873)-specific DNA probes, respectively. The representative results were shown in FIGS. 14C, D, and E. Deletion of sequences between nt 447 and 474 (Pav1615) containing the TATA box of E1A promoter resulted in the lower levels of E2A (FIG. 14C), E3 (FIG. 14D), and E4 (FIG. 14E) mRNAs when compared with that of wild-type and other mutant viruses in each experiment. The result suggests that the E1A gene products are required for normal transactivation of other early gene promoter (Berk et al. (1979, *Cell*. 17:935-944); Jones et al. (1979, *Proc. Natl. Acad. Sci. USA*. 76:3665-3669); Zhou et al. (2001, *Virology*. 291:68-76). In contrast, deletions between nt 382 and 433 (Pav59), nt 382 and 449 (Pav514), and nt 382 and 474 (Pav516) containing the regulatory element caused overexpression of E2A, E3, and E4 genes compared with that of wild-type PAV-3.

The Regulatory Element is Required in Trans, But Not in Cis for Efficient Adenoviral DNA Replication To investigate the influences of deletion of a regulatory element on the PAV-3 DNA replication in virus-infected cells, the viral growth and DNA accumulation were examined with a select group of mutant viruses. The growth of mutant viruses relative to that of wild-type PAV-3 was determined by a one-step growth curve on ST cells. Virus infection with wild-type or mutant PAV-3 was performed at a MOI of 5 PFU per cell. At 12, 24, and 36 h postinfection, infected cells were harvested and subjected to three cycles of freezing and thawing. The viral titers of cleared lysates were determined by plaque assay on VIDO R1 cells (FIGS. 15A-15B). The loss of regulatory element between nt 382 and 433 (Pav59) resulted in a lag in virus growth at early times (12 to 24 h) postinfection. Deletion of sequences between nt 447 and 474 (Pav1615) that contain the TATA box of E1A promoter resulted in about 11 fold reduction in viral growth at 36 h postinfection (Pav1615). However, the growth of Pav516 (nt 382-474), that carried the deletion of both regulatory element and E1A TATA box (between nt 382 and 474) displayed a reduction when compared with that of wild-type PAV-3, but an increase when compared with that of Pav1615 in which only TATA box was deleted and regulatory element was left intact. We noticed that the deletion of sequences between nt 432 and 449 (Pav1413) led to 2 fold increase in viral growth than that of wild-type virus at 36 h postinfection.

The PAV-3 cis-acting packaging domain is located between nt 212 and 531 (SEQ ID NO:414) and overlaps the transcriptional control region of E1A. Because packaging efficiency directly determines the production of infectious viral progeny, the growth phenotypes of mutant viruses might be complicated by packaging defect. To exclude the effects of deletion of cis-acting packaging motif(s) on the viral growth, DNA accumulation in virus-infected cells was examined by Southern blot analysis. ST cells were infected with wild-type or mutant virus at a MOI of 5 PFU per cell. At 9, 16, 23 and 30 h postinfection, the cells were collected and high-molecular DNA was isolated. After digestion with HindIII, DNA fragments were separated by agarose gel electrophoresis and subjected to Southern hybridization. Representative results are shown in FIG. 17 Pav1615 (nt 447-474) and Pav516 (nt 382-474) displayed the defective DNA accumulation throughout the infection (16, 23 and 30 h postinfection). The results are in good agreement with their growth properties (FIG. 16). Pav59 (nt 382-433) carrying the deletion of regulatory element showed the similar rate of DNA accumulation at the late times (23 and 30 h) postinfection, but displayed a lower rate of DNA accumulation at the early time (16 h) postinfection compared with that of wild-type virus. However, Pav1413 (nt 432-449), Pav514 (nt 382-449), and wild-type PAV-3 showed the similar rate of DNA accumulation. These results suggested that the regulatory element appears to affect the onset of DNA replication. Surprisingly, Pav16 (nt 151-254) grew to titers 3 fold less than wild-type PAV-3. In addition, Pav16 showed a lower rate of DNA accumulation at early (16 h) and late times (23 and 30 h) postinfection.

To investigate the mechanisms by which the viral DNA replication was affected in mutant viruses, a coinfection experiment was performed in which the ST cells were infected by wild-type PAV-3 along with individual mutant virus at a MOI of 5 PFU (each virus) per cell. At 9, 16, 23, and 30 h postinfection, the high-molecular weight DNA was isolated and analyzed by Southern hybridization. The wild-type and mutant virus DNA fragments were distinguished by double digestion with KpnI and MfeI. The relative intensities of DNA bands on the autoradiograms were quantitated. As shown in FIG. 17, all of the mutant viruses replicated as efficiently as the co-infecting wild-type virus, suggesting that the sequences deleted in the tested mutant viruses including the regulatory element and TATA box, are not required in cis for efficient viral DNA replication. However, the defect in DNA replication in ST cells (FIG. 16) is due to the transacting effects and can be complemented by co-infecting wild-type PAV-3.

E1A Proteins of HAV-5 Complemented the Defective Replication of PAV-3 Mutants

VIDO R1 cell line isolated by transfection of fetal porcine retina cells (FPRC) with the complete E1 region (nt 505-4034) of HAV5 under the control of a constitutive promoter of mouse phosphoglycerate kinase gene promoter has been demonstrated to complement the E1A-deleted recombinant PAV-3. In this study, we also determine the rate of viral DNA accumulation and the growth of mutant viruses in VIDO R1 cells using similar experiments and conditions as used in ST cells described above. The results are shown in FIGS. 18A-18B and 19. Pav59 (nt 382-433) and Pav1615 (nt 447-474), which carry deletions of regulatory element and TATA box of E1A promoter respectively, displayed growth characteristics similar to that of wild-type PAV-3. All of the other tested mutant viruses showed a defective growth (4 to 8 fold reduction) compared with that of wild-type virus. However, in DNA accumulation experiments, all the tested mutant viruses replicated as efficiently as the wild-type virus, with the exception of Pav48, Pav59, Pav1615, and Pav516, which displayed a lag (3 to 6 fold reduction) in DNA accumulation at 9 h postinfection compared with that of wild type virus.

Results

Analysis of mutations in the transcriptional control region of PAV-3 E1A is provided herein and without being bound by theory, suggests a functionally two-faced regulatory element. As described herein, an element that is located upstream of E1A core promoter augments the transcription of E1A but represses the transcription of E1B. Deletion of the regulatory element resulted in a) dramatic reduction in the steady state level of E1A mRNA early times postinfection, b) the increased accumulation of E1B mRNA, and c) the over expression of E2A, E3, and E4 mRNAs.

The regulatory element is not required in cis for efficient viral DNA replication, but can affect in trans the viral growth. Its removal produced a defective virus in terms of both viral DNA accumulation and production of infectious viral progeny at early stage of infection. At the late times postinfection, both the rate of viral DNA accumulation and the infectious viral progeny production displayed nearly the same efficiency as wild-type virus. The defect in virus growth was efficiently complemented in trans with both wild-type PAV-3 in coinfection and the HAV-5 E1A protein constitutively expressed in VIDO R1 cells.

The viral transcription enhancer regions usually exhibit a long tandem repeat (Khoury et al., 1983, Cell. 33:313-314); (Laimins et al. 1984, J. Virol. 49:183-189). In HAV-5, the enhancer element I of E1A contains an 11 bp repeated element which is a critical component of the modulatory sequences (Hearing et al. (1983, Cell. 33: 695-703). When analyzing the sequences of functionally two-faced regulatory element of PAV-3 E1A, we also found repeated elements which displayed a mirror symmetric structure located between nt 374 and 432 relative to the left end of genome and spanned 58 nucleotides. As shown in FIG. 13B, two 'GGGTGT' sequences located at both ends of the structure were separated by repeated 'TGAGA' and 'CCGC' sequences. In addition, there is no potential cis-acting packaging motif(s) overlapping the regulatory element.

Deletion between nt 382 and 433 (Pav59) down-regulated the transcription of E1A, but upregulated that of E1B. The additional deletion of the sequences between nt 312 and 382 (Pav49: nt 312 and 433) (FIG. 13A) did not correspondingly result in the downregulation of E1A, although the E1B was still upregulated as Pav59 did (FIGS. 14A-14F). The results reflected that the sequences between nt 312 and 382 are probably involved in the regulation of E1A transcription, and are associated with the function of regulatory element by an unknown mechanism. It is possible that the sequences between nt 312 and 433 serve as the binding sites for different protein factors which can cooperate and/or counteract with each other. Alternatively, the additional deletion may change the conformation of the left end genome of PAV-3, thereby putting the unknown regulatory element(s) into function to keep the transcription of E1A at the normal level. The results also suggest that the upregulation of E1B and downregulation of E1A are functionally dissociated and accomplished by different mechanisms, although these functions were mediated by the same cis-acting sequences. Deletion of the sequences between nt 432 and 449 (Pav1413), located between the regulatory element and TATA sequences of E1A promoter has no effect on E1A transcription, but up-regulated the transcription of E1B. The results indicated that the deletion (nt 432 and 449) alone could affect the E1B transcription and provided further evidence to support the hypothesis that the regulatory element-mediated regulation of transcription of E1A and E1B was accomplished by different mechanisms.

The level of E1A mRNAs produced by Pav514 (nt 382-449) and Pav516 (nt 382-474), which carried the extended deletions on the background of deletion between nt 382 and 433(Pav59), were not correspondingly reduced further but was increased when compared with that of Pav59 (FIG. 14A). It is possible that the E1A mRNA can be produced under control of a different promoter such as ITR of PAV-3. It has been established that the ITR in adenovirus has the promoter activity (Hatfield et al. (1991, Virology. 184:265-276). The sequence analysis of cDNA clones representing the E1A region of PAV-3 has revealed that the transcription start site is heterogeneous and often lies upstream of the TATA box of the E1A, suggesting the use of PAV-3 ITR as a promoter (Reddy et al., 1998, Virus Res. 58:97-106). It is also possible that the inactivation of the original regulatory control region led to active participation of another control region. The E1A mRNAs detected in ST cells infected with Pav514 and Pav516 probably represent the activity of other unknown regulatory element or even promoter, such as the left ITR.

Although Pav514 displayed the reduced transcription of the E1A, it showed the strongest activity of E2A promoter (FIG. 14C) and replicated as efficiently as the wild-type PAV-3. We do not know the mechanism of upregulation of E2A and how the E1 and E2 regions cooperatively regulate the viral DNA replication since proteins encoded by the E2 region are directly involved in viral DNA synthesis (Reddy et al. 1-998, Virology. 251:414-426); (Russell, W. C., 2000, J. Gen. Virol. 81:2573-2604). It is possible that the up-regulated expression of E2 genes could complement the viral growth defect resulted from the reduced transcription of E1A gene in term of viral DNA replication. The cis-acting packaging domain of PAV-3 overlaps the transcriptional control region of E1A. It is believed that two kinds of regulatory elements could influence each other (Hearing et al., 1983, Cell. 33: 695-703); (Hearing et al., 1986, Cell. 45: 229-236). Active utilization of the enhancer element could delay the onset of packaging, and the onset of packaging could in turn decrease E1A transcription (Hearing et al., 1983, Cell. 33: 695-703). However, it is not clear how these two regulatory elements influence each other. It appears that the growth properties of mutant PAV-3 in ST cells could represent the combined effects of deficiency in both packaging ability and early gene expression. However, the loss of regulatory element and/or TATA box of E1A promoter can be complemented with HAV-5 E1 proteins constitutively expressed in VIDO R1 cells, the viral growth defect in VIDO R1 cells appears to result mainly from the deficiency in packaging efficiency.

Like HAV (Russell, W. C., 2000, J. Gen. Virol. 81:2573-2604), the E1A and E1B of PAV-3 are transcribed from different promoters (Reddy et at. (1998, Virus Res. 58:97-106). It appears that the regulatory element for E1A overlaps with that for E1B and share some of the common DNA sequences to regulate the transcription by different mechanisms. For adenoviral productive infection, E1A is used to stimulate the cell cycle into S phase (Boulanger et at. (1991, Biochem. J. 275:281-299). This regulation of cell cycle subsequently activates a premature cell death (apoptosis) (Chiou et at., 1997, J. Virol. 71:3515-3525); (Lowe et al., 1993, Genes Dev. 7:535-545). In contrast, the proteins encoded by E1B including 19 kDa and 55 kDa can function independently to inhibit apoptosis induced by E1A. (Debbas et at., 1993, Genes Dev. 7:546-554); (Goodrum et at., 1997, T J. Virol. 71:548-561). In addition, E1A and E1B have opposite functions in transactivation of other early promoters. For instance, the E2 late promoter is repressed by E1A (Guilfoyle et al., 1985, EMBO J. 4:707-713), but is induced by E1B 55kDa (Holm et at., 2002, J. Biol. Chem. 277:10427-10434). To manipulate the cells for productive viral infection, it is required that virus expresses the proteins with counteracting functions in a proper proportion. Therefore, the balanced expression of E1A and E1B is important to the viral life cycle. The overlapping of gene-specific regulatory elements of PAV-3 could facilitate to achieve this at the transcriptional level.

TABLE 4

Probes used for Northern and Southern hybridizations.

| Probes | Nucleotide position[a] |
|---|---|
| E1A[b] | 531-844 |
| E1B[c] | 1411-3077 |
| E2A[d] | 22667-23736 |
| E3[e] | 27587-29011 |
| E4[f] | 32504-33873 |
| Southern blot in single infection[g] | 934-2190 |
| Southern blot in coinfection[h] | 531-844 |

[a]Numbers indicate the nucleotide position (nt) relative to the left terminus of wild-type PAV-3 genome (GenBank accession No. AF083132). PAV-3 nucleotide sequences are indicated in boldface type.
[b,h]0.3 Kb DNA fragment was generated by PCR using primers P20 (5'-CCG-CAATTGACATGGCGAACAGACTTC-3', sense, nt 531-548) (SEQ ID NO: 40) and P2 (5'-CGCGCTGATATCCTCCTC-3', antisense, nt 827-844) (SEQ ID NO: 22).
[c]1.6 Kb PstI fragment released from plasmid pPAV3.XhoIRL containing the left end (nt 1-4161) of PAV-3 genome.
[d]1.0 Kb DNA fragment was generated by PCR using primers PDBP-4 (5'-GCGTCGACTCAAAACAGGCTCTCAT-3', sense, nt 22667-22684) (SEQ ID NO: 48) and PDBP-3 (5'-CGGGATCCGGCCGCTGCTGCAGCT-3', antisense, nt 23719-23736) (SEQ ID NO: 49).
[e]1.4 Kb PstI fragment released from plasmid pGEM32 containing KpnI/BamHI fragment (nt 26716-31064) of PAV-3 genome.
[f]1.3 Kb SmaI fragment released from pPAV3.XhoIRL.
[g]1.2 Kb KpnI/Eco47-3 fragment from pPAV3.XhoIRL.

EXAMPLE 5

Confirmation of Packaging Domains of PAV

Materials and Methods

Cells and viruses. VIDO R1 a transformed fetal porcine retina cell (FPRC) line expressing the E1A and E1B proteins of human adenovirus type 5 (HAV-5) under the control of mouse phosphoglycerate kinase gene promoter, was used in the below experiments. The cells were grown and maintained in Eagle's minimum essential medium (MEM) supplemented with 10% fetal bovine serum (FBS). Wild-type (6618 strain) (Derbyshire et al., 1975, Supra) and mutant PAV-3s were propagated and titrated in VIDO R1 cells.

PCR amplification. PCR was performed in a total volume of 50 l in the following conditions: 0.5 μg of template DNA, 1×PCR buffer (10 mM KCl, 10 mM $(NH_4)_2SO_4$, 20 mM Tris-Cl (pH 8.75), 2 mM $MgSO_4$, 0.1% Triton®X-100, 0.1 mg/ml BSA) (Stratagene), 0.4 mM dNTPs, 10 pmol of each primer, 2.0 U of cloned pfu DNA polymerase (Stratagene). The cycling conditions were: 94° C. for 2 min to denature the DNA, followed by 30 cycles consisting of 94° C. for 40 s, 50° C. for 40 s, 72° C. for 40 s, and finally, extension at 72° C. for 2 min. The products of PCR were separated on a 2% agarose gel and visualized by ethidium bromide (EtBr) staining. The primers used in PCR are shown in Table 5.

Construction of recombinant plasmids. To construct the mutant PAV-3, the deletions or linker-scanning mutations were constructed in recombinant plasmids by virtue of PCR method as described herein. The genomic DNAs isolated from mutant viruses Pav3-252/531, Pav3-312/531, Pav3-382/531, and Pav3-151/383, which carry deletions of sequences between nt 252 and 531, nt 312 and 531, nt 382 and 531, and, nt 151 and 383 respectively, were used as templates in PCR amplification. These plasmids were characterized by restriction endonuclease analysis.

Isolation of PAV3 mutants. VIDO R1 cell monolayers cultured in a 35 mm dish in diameter were transfected with 5 μg of PacI-digested individual full-length plasmid DNA by using the Lipofectin methods according to the instructions of manufacturer (Invitrogen). After 10 to 15 days of incubation at 37° C., the transfected cells were collected and freeze-thawed three times. The lysates were used to infect the freshly prepared VIDO R1 cells until cytopathic effect appeared. Finally, the recombinant viruses were characterized by PCR and DNA sequence analysis, and then expanded and titrated on VIDO R1 cells.

Determination of virus yields and packaging efficiency. As described herein, virus infection was performed at an multiplicity of infection (MOI) of 5 plaque forming unit (PFU) per cell at 37° C. for 1 h. The cells were washed and then fresh medium was added. To determine viral yield in single-virus infections, infected VIDO R1 cells were harvested 48 h postinfection and then lysed by three cycles of freezing and thawing. The infectious virus yields in cleared lysates were determined by plaque assay on VIDO R1 cells. The data presented for virus yields from single infections represent the averages of three independent experiments.

To determine the packaging efficiency of the mutant viruses, we employed a coinfection experiment in which VIDO R1 cells were infected with individual mutant virus along with the wild-type PAV-3 at a MOI of 5 PFU each virus per cell. Forty-eight hours postinfection, one-half of the cells were used to isolate high-molecular-weight; DNA, and the other half of the cells were used to prepare viral DNA from virions. For the isolation of infected cell high-molecular-weight DNA, the cells were lysed by the addition of Nonidet P-40 to 0.4%, and then digested with proteinase K at 50° C. for at least 2 hr. The high-molecular-weight DNA was isolated as described by (Sambrook, et al, 1989, Supra). For the isolation of viral DNA from virions, infected cells were reprecipitated and suspended in lysis buffer (20 mM Tris Cl[pH8.0], 0.2% deoxycholate, 10% ethanol). After incubation for 60 min at room temperature, the lysate was cleared at 10,000×g for 30 min. The supernatant was adjusted to 2 mM $CaCl_2$ and 2 mM $MgCl_2$, and was digested with 40 μg of RNase A per ml and 10 μg of DNase I per ml at 37° C. for 30 min. The reaction was stopped by the addition of EDTA and EGTA to a final concentration of 50 mM each. Virus particles were lysed by the addition of Sarkosyl to 0.5%, and the samples were digested with 1 mg of proteinase K per ml at 50° C. for 1 h to 2 hr. After phenol and chloroform extraction, the viral DNA was precipitated with ethanol. The DNAs isolated from nuclei or virions were digested with SpeI and KpnI, and then analysed by Southern hybridization.

Southern hybridization. The SpeI and KpnI digested DNAs were separated on 1.5% agarose gel and then transferred to Gene Screen Plus hybridization transfer membrane (Perkin Elmer Life Science) by high salt capillary transfer method according to the instructions of manufacturer. The 314 by DNA fragment corresponding to nt 531 and 844 was amplified by PCR with primers P2 and PR12, labeled with $^{32}P$-dCTP by the random primer method using Random Primers DNA labelling system (Invitrogen), and was used as a probe in Southern hybridization analysis. The blots were prehybridized in ULTRAhyb ultrasensitive hybridization buffer (Ambion® RNA) at 42° C. for 30 min, and then $^{32}P$-labeled probes were added. Hybridization was performed at 42° C. overnight. After extensively washing with 0.1×SSC and 0.1% SDS, the blots were exposed to X-ray film (Kodak) without an intensifying screen. The bands in autoradiograms were scanned and their relative intensities were determined and analysed by Computing Densitometer using PhosphoImager programme (Bio-Rad), The data presented for packaging efficiency based on coinfection experiments represent the averages of three independent.

TABLE 5

PRIMERS USED IN PCR EXPERIMENTS IN EXAMPLE 5.

| Primer | Sequences[a] | Nucleotide Position[b] (nt) |
|---|---|---|
| P1: | 5'-CGTCTTCAAGGATCCTTA-3'<br>(SEQ ID NO: 21) | sense, BamHI |
| P2: | 5'-CGCGCTGATATCCTCCTC-3'<br>(SEQ ID NO: 22) | (827-844) antisense |
| PSR32: | 5'-CGGCGGGATCCTTAATTAACATCATCAATAA<br>TATACCGCACACTTTT-3'<br>(SEQ ID NO: 47) | (1-29) |
| PA1: | 5'-CGGACTAGTCCGCCGCTCGGCCC-3'<br>(SEQ ID NO: 50) | (219-233) antisense |
| PA2: | 5'-CGGACTAGTCCCGCACAGGTGGAGAGT-3'<br>(SEQ ID NO: 51) | (237-255) sense |
| PA3: | 5'-CGGACTAGTCCCGCGGTACTCTCCACC-3'<br>(SEQ ID NO: 52) | (246-264) antisense |
| PA4: | 5'-CGGACTAGTGTGCCCTCTGGACCGGAC-3'<br>(SEQ ID NO: 53) | (268-286) sense |
| PA9: | 5'-CGGACTAGTCACTGAGGGGAAAAAATACA-3'<br>(SEQ ID NO: 54) | (429-448) antisense |
| PA10: | 5'-CGGACTAGTGTCCGCGCAGCGCCCGAGA-3'<br>(SEQ ID NO: 55) | (455-473) sense |
| PA11: | 5'-CGGACTAGTCTCTACTCCCTTCGGACT-3'<br>(SEQ ID NO: 56) | (487-504) antisense |
| PA12: | 5'-CGGACTAGTCTCTCAGCGGAACAGACCC-3'<br>(SEQ ID NO: 57) | (508-527) sense |
| PL1: | 5'-CGGACTAGTCTCGGCCCCGCCCG-3'<br>(SEQ ID NO: 58) | (212-226) antisense |
| PL2: | 5'-CGGACTAGTAAATTCCCGCACAGGTGG-3'<br>(SEQ ID NO: 59) | (233-250) sense |
| PL3: | 5'-CGGACTAGTGTACTCTCCACCTGTGCG-3'<br>(SEQ ID NO: 60) | (240-257) antisense |
| PL4: | 5'-CGGACTAGTATTTTGTGCCCTCTGGAC-3'<br>(SEQ ID NO: 61) | (264-281) sense |
| PL9: | 5'-CGGACTAGTGGGGAAAAAATACACCCACA-3'<br>(SEQ ID NO: 62) | (423-442) antisense |
| PL10: | 5'-CGGACTAGTTATATAGTCCGCGCAGCGC-3'<br>(SEQ ID NO: 63) | (449-467) sense |
| PL11: | 5'-CGGACTAGTACTCCCTTCGGACTCAAG-3'<br>(SEQ ID NO: 64) | (483-501) antisense |
| PL12: | 5'-CGGACTAGTTTTTCTCTCAGCGGAACAG-3'<br>(SEQ ID NO: 65) | (505-523) sense |
| PR1: | 5'-CGGACTAGTAATTTCCGCCGCTCG-3'<br>(SEQ ID NO: 66) | (223-237) antisense |
| PR2: | 5'-CGGACTAGTACAGGTGGAGAGTACCGC-3'<br>(SEQ ID NO: 67) | (243-260) sense |
| PR3: | 5'-CGGACTAGTAAAATCCCGCGGTACTCT-3'<br>(SEQ ID NO: 68) | (251-268) antisense |
| PR4: | 5'-CGGACTAGTTCTGGACCGGACCTTCGC-3'<br>(SEQ ID NO: 69) | (275-292) sense |
| PR9: | 5'-CGGACTAGTTATATACACTGAGGGGAAAA-3'<br>(SEQ ID NO: 70) | (435-454) antisense |

TABLE 5-continued

PRIMERS USED IN PCR EXPERIMENTS IN EXAMPLE 5.

| Primer Sequences[a] | Nucleotide Position[b] (nt) | |
|---|---|---|
| PR10: | 5'-CGG<u>ACTAGT</u>GCAGCGCCCGAGAGTCACT-3' (SEQ ID NO: 71) | (461-479) sense |
| PR11: | 5'-CGG<u>ACTAGT</u>AAAACTCTACTCCCTTCG-3' (SEQ ID NO: 72) | (491-508) antisense |
| PR12: | 5'-CGG<u>ACTAGT</u>AGCGGAACAGACCCTCGAC-3' (SEQ ID NO: 73) | (514-532) sense |
| PM1: | 5'-CGG<u>ACTAGT</u>CGCTCGGCCCCGCC-3' (SEQ ID NO: 74) | (215-228) antisense |
| PM2: | 5'-CGG<u>ACTAGT</u>CACAGGTGGAGAGTACC-3' (SEQ ID NO: 75) | (242-258) sense |
| PM3: | 5'-CGG<u>ACTAGT</u>CGGTACTCTCCACCTGTG-3' (SEQ ID NO: 76) | (242-259) antisense |
| PM4: | 5'-CGG<u>ACTAGT</u>CCTCTGGACCGGACCTTC-3' (SEQ ID NO: 77) | (273-290) sense |
| PM5: | 5'-CGG<u>ACTAGT</u>GCCGCGGACGTGTGGTGC-3' (SEQ ID NO: 78) | (312-329) antisense |
| PM6: | 5'-CGG<u>ACTAGT</u>ACCTGACGACGGTGACAC-3' (SEQ ID NO: 79) | (342-359) sense |
| PM7: | 5'-CGG<u>ACTAGT</u>CCACACACGTCATCTCGG-3' (SEQ ID NO: 80) | (410-427) antisense |
| PM8: | 5'-CGG<u>ACTAGT</u>CTCAGTGTATATAGTCC-3' (SEQ ID NO: 81) | (442-458) sense |
| PM9: | 5'-CGG<u>ACTAGT</u>TGAGGGGAAAAAATACAC-3' (SEQ ID NO: 82) | (428-445) antisense |
| PM10: | 5'-CGG<u>ACTAGT</u>GCGCAGCGCCCGAGAGTCA-3' (SEQ ID NO: 83) | (459-477) sense |
| PM11: | 5'-CGG<u>ACTAGT</u>TACTCCCTTCGGACTCAA-3' (SEQ ID NO: 84) | (484-501) antisense |
| PM12: | 5'-CGG<u>ACTAGT</u>TCAGCGGAACAGACCCTCG-3' (SEQ ID NO: 85) | (512-530) sense |

[a]The restriction endonuclease cleavage sites are underlined.
[b]Numbers indicate the nucleotide position relative to the left terminus of PAV-3 (Reddy et al., 1998) genome, PAV-3 nucleotide sequences are indicated in boldface type.

Results

Results

Mutational analysis of motif I, II, and 111. As described herein, the deletion of sequences between nt 212 and 254, nt 252 and 313, at 312 and 383, at 432 and 449, and nt 447 and 474, and nt 495 and 531 resulted in reduction in packaging efficiency of PAV3. The common character of these regions in DNA sequence is that each contains a AT-rich unit which was presumably the potential packaging motif. To define the PAV-3 packaging domain in detail and obtain the direct evidence showing that these AT-rich units can function as cis-acting packaging motifs, the continuous A/T nucleotides and the flanking sequences were targeted with deletion or linker scanning mutations. To construct mutations in the packaging domain, the SpeI linker containing 'ACTAGT' sequences was used to disrupt the AT-rich or GC-rich character of DNA sequences. Due to the functional redundancy of the packaging motifs of PAV-3, all the mutations were introduced) in the context of a deletion of different potential packaging motif(s).

The resulting virus mutants containing deletions or linker-scanning mutation were rescued on VIDO R1 cells and characterized by PCR using primer pair PSR32—P2. PCR products were analyzed with DNA sequencing. Two independent assays were employed to test all the virus mutants. First, infectious virus yield in VIDO R1 cells was determined by plaque assay at 48 h postinfection. The PAV-3 packaging domain overlaps the transcriptional control region of early region 1 (E1) which is required for normal transcription from other viral early genes and subsequently for viral DNA replication in infected cells (Zhou et al., 2001, Supra). Therefore, the mutations in packaging domain could affect the viral growth independently of the packaging deflect. To exclude the effect of reduced expression of early genes on viral overall growth observed in the single infection, we performed a coinfection experiment in which VIDO R1 cells were infected with the individual virus mutant along with the wild-type virus providing all viral gene products in trans. Total replicated DNA and packaged DNA were isolated from VIDO R1 cells after at 48 h postinfection. Mutant and wild-type viral DNAs were distinguished by double digestion with SpeI and KpnI. The relative amounts were quantitated by subsequent Southern blot analysis. The amount of packaged mutant virus DNA relative to the coinfecting wild-type DNA was normalized to the levels of totally replicated DNA of each mutant and wild-type virus. By comparing the relative amounts of mutant and wild-type viral DNA present in intact virions with the relative amounts of each totally replicated viral DNA, the reduction in packaging efficiency of mutant virus relative to that of wild-type virus was accurately measured independently of other transacting effects.

FIG. 21A(1) shows the mutations introduced into the motif I and summarizes the results obtained with these mutant viruses. FIG. 21B is a representative Southern blot of coinfection experiment. The mutations were introduced in the context of a parent mutant virus Pav3-252/531, that carries a deletion of motif II through VI, and displays a 12 fold reduction in viral yield in a single infection and 9 fold decrease in packaging efficiency in coinfections. A deletion of 14 by sequences between nt 228 and 242 (Pav3-PMI) resulted in nonviability of mutant virus in VIDO R1 cells. A substitution of continuous A/T nucleotides from at 233 to 237 with ACT-AGT sequences (SpeI linker) (Pav3-PA1) resulted in the same phenotype as Pav3-PM1. The continuous A/T nucleotides in motif I was flanked by GC-rich sequences. A substitution of upstream GC-rich sequences from 227 to 232 with SpeI linker resulted in a dramatic decrease in both viral yield in single infection (40 fold) and packaging efficiency in the coinfection (34 fold). The results indicated that the AT-rich unit I served as a packaging motif and in this case, the continuous A/T nucleotides are critical for the packaging function. In addition, flanking GC-rich sequences are also important for the full function of this packaging motif.

FIG. 21A(2) shows the mutations introduced into the motif I or II in the context of a parent mutant virus Pav3-312/531, that carries a deletion of motif III through VI, but motif I and II are left intact. The results obtained with these mutant viruses were summarized and presented in FIG. 21A(2). Parent mutant virus displayed a 7 fold reduction in viral yield in a single infection and a 8 fold decrease in packaging efficiency in the coinfection when compared with that of wild-type virus. A mutant virus Pav3-PA12 that carries a substitution of continuous A/T sequences of motif I with SpeI linker and a mutant virus Pav3-PR1 carrying a substitution of continuous G/C nucleotides downstream of continuous A/T sequences, displayed a 42 fold and 15 fold reduction in viral yield in a single infection, respectively. In coinfection experiment, the packaging efficiency of Pav3-PA12 and Pav3-PR1 was reduced 31 fold and 12 fold compared with that of wild-type PAV-3, respectively. That is 23 fold and 4 fold more reduction in packaging efficiency than that of parent virus Pav3-312/531. The results demonstrate that the A/T sequences and its flanking G/C sequences are functionally important components of motif 1. Pav3-PM3 carrying a deletion of 13 bp sequences between nt 248 and 263 displayed a 35 fold reduction in viral yield in single infection and a 28 fold reduction in packaging efficiency in coinfection compared to that of wild-type virus. When compared with parent virus Pav3-312/531, the packaging efficiency of Pav3-PM3 was reduced 20 fold. In the case of motif II, a substitution of continuous A/T sequences from nt 253 to 257 (Pav3-PA3) and a substitution of upstream continuous G/C nucleotides from at 247 to 252 (Pav3-PL3) with the SpeI linker resulted in a 30 fold and 20 fold reduction in viral yield in single infection, respectively. These virus mutants displayed a 26 fold and 21 fold reduction in packaging efficiency in coinfection when compared to that of wild-type virus. Pav3-PR3, carrying a substitution of downstream continuous G/C nucleotides of motif III with SpeI linker displayed a 9 fold reduction in growth in single infection and 10 fold reduction in packaging efficiency in coinfection. The results indicated that the motif II is a cis-acting packaging motif. The continuous A/T sequences and its upstream and downstream flanking G/C sequences all played an important role in the function of motif II.

FIG. 21A(3) shows a deletion introduced in the AT-rich unit III in the context of a mutant parent virus Pav3-382/531, that carries a deletion of unit IV through VI between nt 382 and 531. The parent virus displayed a 3 fold reduction in viral yield in single infection and a 5 fold decrease in packaging efficiency in coinfection. A deletion of 11 by sequences between nt 329 and 342 resulted in a 11 fold more reduction in viral yield in single infection and a 4 fold further decrease in packaging efficiency when compared to that of parent virus. The results provide the evidence showing that the AT-rich unit III is directly involved in the packaging process.

Mutational analysis of motif IV, V, and VI. To analyze the motif IV, V, and VI, the deletions and linker scanning mutations were introduced into the context of a mutant virus Pav3-151/382, that carries a deletion of motif I, II, and III. FIG. 22A shows the results obtained with these mutant viruses. FIG. 22B shows the Southern Blot results of co-infection. The parent virus Pav3-151/382 displayed an 8 fold reduction in viral yield in single infection, and a 7 fold decrease in packaging efficiency in coinfection. The deletions between nt 426 and 441 (Pav3-PM7), nt 444 and 458 (Pav3-PM9), and between nt 501 and 512 (Pav3-PM12) resulted in a 16 fold, 24 fold, and 19 fold reduction in the packaging efficiency in coinfection, respectively. When compared with the parent virus Pav3-151/382, the packaging efficiency of PM7, PM9, and PM showed 9 fold, 17 fold, and 12 fold more decrease. The results demonstrated that the motif IV, V, and VI served as independent packaging motifs. The motif V contains TATA sequences that have been identified to be TATA box of E1A promoter (Reddy et al., 1998, Supraa). The substitution of TATATA sequence (Pav3-PA9) with SpeI linker resulted in 10 fold reduction in packaging efficiency, namely 3 fold more reduction than parent virus Pav3-751/382. When its downstream (Pav3-PL9) and upstream (Pav3-PR9) flanking sequences were individually substituted with SpeI linker, the reduction in packaging efficiency in coinfection is not evident when compared with that of parent virus. In the case of motif VI, the substitution of continuous A/T nucleotides (Pav3-PA112) resulted in 12 fold reduction in packaging efficiency. However, the substitution of its flanking sequences (Pav3-PL11 and Pav3-PR112) with SpeI linker did not result in the detectable further decrease in packaging efficiency when compared with the parent virus.

Figures 23A, 23B:
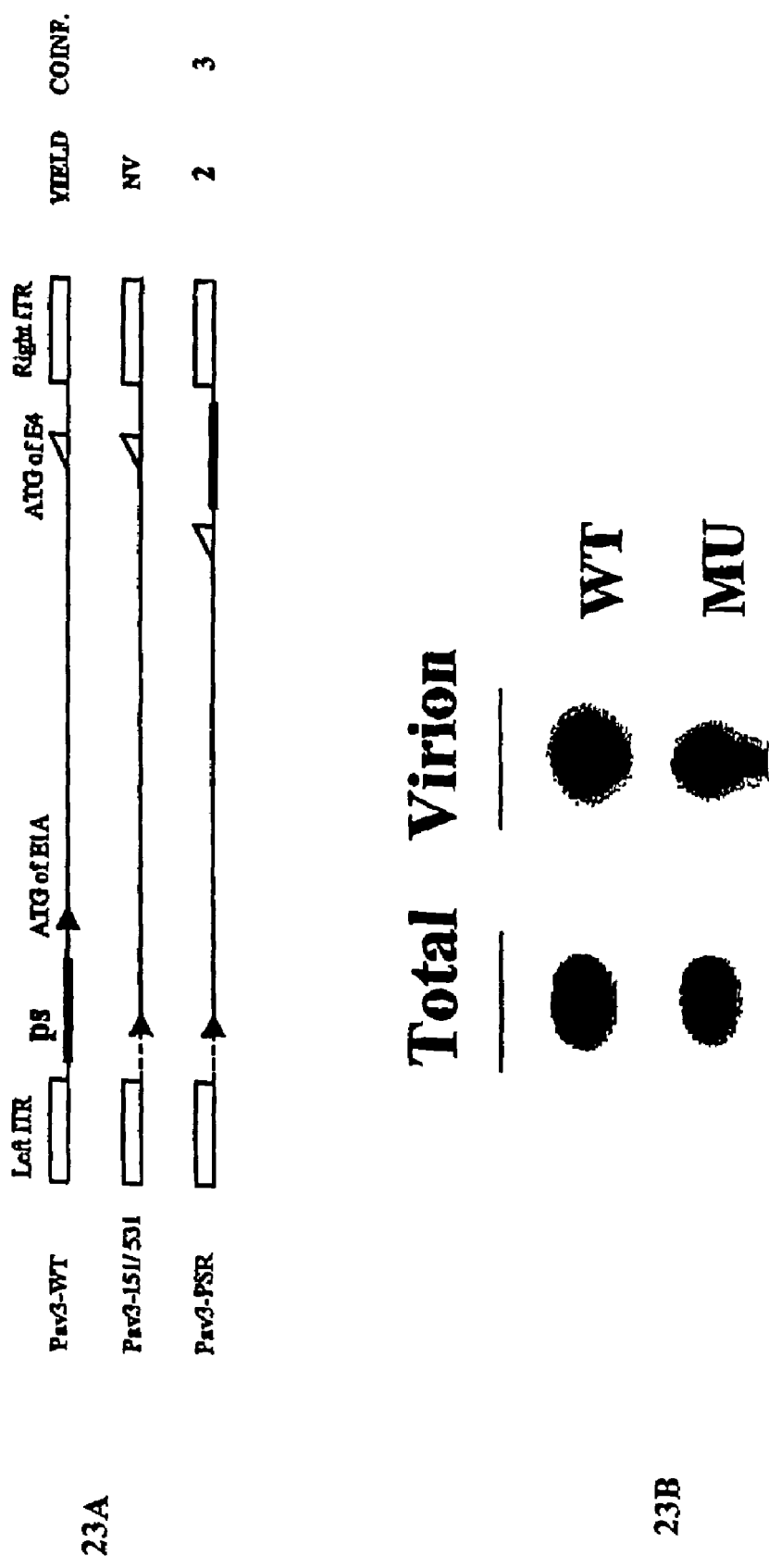
Figure 3A:
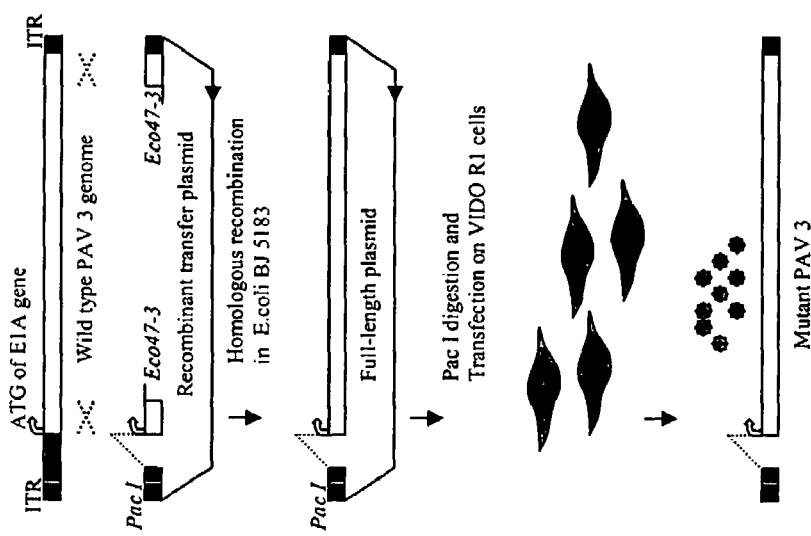
Figure 3B:
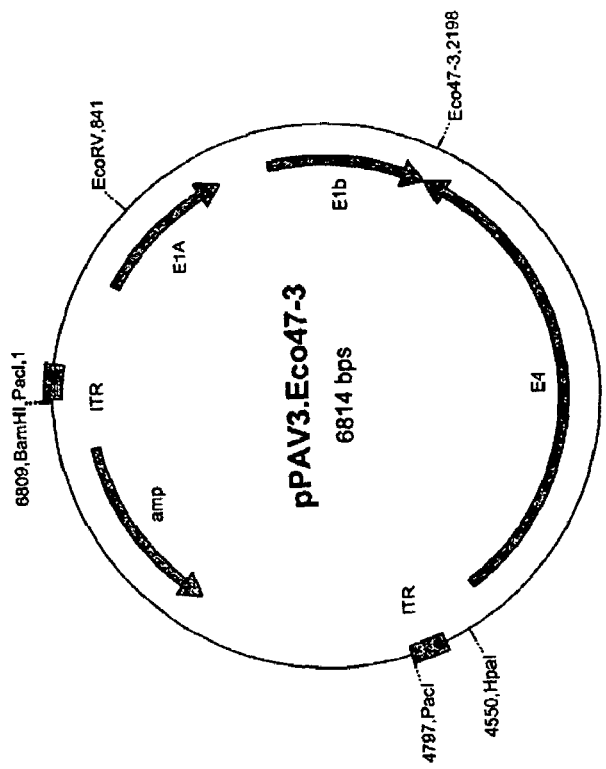

Cis-acting packaging domain keeps the same packaging efficiency when located at the right end of genome. Although the known packaging domain of adenoviruses (including human and nonhuman adenoviruses) investigated to date is usually located near the left end of genome, the cis-acting packaging domain of HAV-5 can still provide the packaging ability when it was moved from its original position at the left end genome to the right end genome. To test the positional flexibility of PAV-3 packaging domain, a mutant virus Pav3-PSR carrying the packaging motif I through V at the right end genome was constructed. Pav3-PSR was constructed in the context of a virus mutant Pav3-151/531 that carries a deletion of the whole original packaging domain at its original location and is nonviable in VIDO R1 cells. As shown in FIG. 23A, the appearance of packaging motif I through V at the right end of the genome rescued the viable virus mutant. This virus mutant displayed a 2 fold reduction in viral yield in single infection and a 3 fold decrease in packaging efficiency in coinfection. The results showed that Pav3-PSR has the same phenotype in packaging efficiency as Pav3-461/531, which carries the identical packaging domain (motif I through V) at the left end genome, demonstrating the packaging domain keeps the same efficacy when located near both ends of genome.

Discussion

A series of PAV-3 mutants carrying deletions located between the left ITR and start ATG codon of E1A gene were analyzed. By comparing the packaging efficiency of virus mutants, the cis-acting packaging domain was primarily identified in six different deletions. Each of these deletions contains a AT-rich unit. The packaging domains were confirmed by mutational analysis of the continuous A/T sequences and the upstream and downstream flanking sequences. The packaging motif I, II, III, and IV displayed a tripartite structure in which the continuous A/T nucleotides are flanked by G/C-rich sequences without being bound by theory. The continuous A/T sequences appear to play a more important role in viral packaging than the flanking G/C-rich sequences. For instance, the motif I was inactivated by a mutation in the continuous A/T sequences, but not in its GC-rich flanking sequences, although the mutations in the upstream or downstream GC-rich flanking sequences also resulted in a dramatic reduction in the efficacy of motif I. In contrast to motif I, II, III, and IV, the continuous A/T nucleotides of motif V and VI were flanked by GA/TG or G/CTC, instead of the continuous G/C sequences. The single mutation in continuous A/T sequences, or the upstream or downstream flanking sequences, has no detectable effect on the packaging efficiency, although the combined deletion of continuous A/T and its flanking sequences displayed a dramatic reduction in packaging efficiency.

Without being bound by theory, in addition to the cis-acting packaging domain(s), the ITR of viral genome also has been thought to be involved in packaging process. The first evidence for this hypothesis comes from the positional constraints of HAV-5 packaging domain. Although the packaging domain of HAV5 could function when it was moved outside its original location or even into the right end genome, it must be located within 600 by near ITR (Hammarskjold and Winberg, 1980, Supra; Hearing et al., 1983, 1987, Supra). The deletion of PAV3 packaging domain between nt 151 and 531 (Pav3-151/531) made the virus mutant nonviable. The insertion of PAV3 packaging domain between nt 151 and 531 (including motif I through V) into the right end genome between the E4 gene and right ITR rescued the virus mutant. This mutant displayed the same packaging efficiency as Pav3461/531, which carries the identical packaging sequences, but located at the left end genome. Therefore, like human adenovirus, it appears that the PAV ITR and cis-acting packaging domain(s) represent the total DNA sequences required for selective packaging of PAV-3 DNA.

The adenovirus E1 gene products including E1A and RIB are the first viral proteins to be expressed after infection. They transactivate the transcription from other early gene promoters and are essential for viral replication. It has been demonstrated for both HAV-5 and PAV-3 that the transcriptional control region of E1 genes overlaps the cis-acting packaging domain. In HAV-5, the cis-acting packaging domain is located upstream of EIA gene promoter and overlaps two distinct enhancer elements. The element I specifically stimulates the transcription of E1A, but element II enhances all early gene transcription. In contrast to HAV-5, the promoter region of EIA gene of PAV-3 is nested in the cis-acting packaging domain. The TATA box of EIA promoter can function as a packaging motif by itself.

The invention claimed is:

1. A porcine adenovirus sequence essential for encapsidation, wherein said sequence consists of the nucleotide sequence between nt 212 and 531 (SEQ ID NO:414) of porcine adenovirus type 3, wherein said nucleotide sequence comprises the sequence TATTTTTT and wherein the nucleotide sequence is capable of encapsidating an adenovirus genome.

2. A porcine adenovirus sequence essential for encapsidation wherein said nucleotide sequence comprises Motif IV represented by $X_{IV}$TATTTTTT$Y_{IV}$, wherein $X_{IV}$ is selected from the group consisting of G, TG, GTG, GGTG, and GGGTG, and wherein $Y_{IV}$ is selected from the group consisting of CCCCTCA, CCCCTC, CCCCT, CCCC, CCC, CC, and C (SEQ ID NOS: 7, 8, 100, 224-255); wherein the nucleotide sequence is not more than 20 nucleotides in length.

3. The porcine adenovirus sequence essential for encapsidation of claim 1 wherein said sequence comprises a nucleotide sequence selected from the group consisting of:

GTGTATTTTTTCCCCTCA (SEQ ID NO: 7); and
GGGTGTATTTTTTCCCCTCA (SEQ ID NO: 8) wherein the nucleotide sequence is not more than 20 nucleotides in length.

4. The replication-defective recombinant adenovirus vector which comprises a porcine adenovirus sequence essential for encapsidation, wherein said sequence essential for encapsidation consists of the nucleotide sequence between nt 212 and 531 (SEQ ID NO:414) of porcine adenovirus type 3, wherein said nucleotide sequence comprises the sequence TATTTTTT, wherein the nucleotide sequence is capable of encapsidating an adenovirus genome, and wherein said porcine adenovirus sequence essential for encapsidation is heterologous to said adenovirus vector.

5. The recombinant adenovirus vector of claim 4 wherein said adenovirus vector comprises human adenoviral sequences.

6. The recombinant adenovirus vector of claim 4 wherein said adenovirus vector comprises bovine adenoviral sequences.

7. The recombinant adenovirus vector of claim 4 which further comprises at least one nucleic acid sequence encoding a transgene.

8. A replication-defective recombinant adenovirus vector which comprises a porcine adenovirus sequence essential for encapsidation;

wherein said sequence essential for encapsidation consists of the nucleotide sequence between nt 212 and 531 (SEQ ID NO:414) of porcine adenovirus type 3;

wherein said nucleotide sequence essential for encapsidation comprises the sequence TATTTTTT;

wherein the nucleotide sequence essential for encapsidation is capable of encapsidating an adenovirus genome; and wherein the replication-defective recombinant adenovirus vector comprises at least one inverted terminal repeat sequence from a human adenovirus.

9. A replication-defective recombinant adenovirus vector which comprises a porcine adenovirus sequence essential for encapsidation;

wherein said sequence essential for encapsidation consists of the nucleotide sequence between nt 212 and 531 (SEQ ID NO:414) of porcine adenovirus type 3;

wherein said nucleotide sequence essential for encapsidation comprises the sequence TATTTTTT;

wherein the nucleotide sequence essential for encapsidation is capable of encapsidating an adenovirus genome; and wherein the replication-defective recombinant adenovirus comprises at least one inverted terminal repeat sequence from a bovine adenovirus.

10. The recombinant adenovirus vector of claim 4 wherein said adenovirus vector comprises a porcine adenovirus sequence essential for encapsidation, at least one inverted terminal repeat sequence and nucleic acid encoding a transgene, wherein said adenovirus vector is deleted in a nucleic acid sequence encoding an adenovirus protein.

11. The recombinant adenovirus vector of claim 4, wherein said adenovirus vector comprises a human adenovirus sequence or bovine adenovirus sequences.

12. The recombinant adenovirus vector of claim 10 wherein said transgene encodes an immunogenic polypeptide.

13. The recombinant adenovirus vector of claim 10 wherein said transgene encodes an antigen of a pathogen.

14. The recombinant adenovirus vector of claim 13 wherein said pathogen is a human pathogen.

15. The recombinant adenovirus vector of claim 13 wherein said pathogen includes a bovine pathogen, porcine pathogen, canine pathogen, feline pathogen or equine pathogen.

16. A recombinant porcine adenovirus vector which comprises a porcine adenovirus sequence essential for encapsidation; wherein said sequence essential for encapsidation consists of the nucleotide sequence between nt 212 and 531 (SEQ ID NO:414) of porcine adenovirus type 3; wherein said sequence essential for encapsidation comprises the nucleotide sequence TATTTTTT and wherein said nucleotide sequence essential for encapsidation comprises a deletion of a part of the porcine adenovirus sequence essential for encapsidation.

17. An isolated host cell comprising the adenovirus vector of any one of claims 4, 8 or 9.

18. An isolated host cell comprising the adenovirus vector of claim 16.

19. The host cell of claim 17 which is mammalian.

20. The host cell of claim 18 which is mammalian.

21. A recombinant adenovirus particle comprising the adenovirus vector of any one of claims 4, 8, or 9.

22. A recombinant adenovirus particle comprising the adenovirus vector of claim 16.

23. A composition comprising the adenoviral vector of any one of claims 4, 8 or 9.

24. A composition comprising the adenoviral vector of claim 16.

25. The composition of claim 23 further comprising a pharmaceutically acceptable carrier.

26. The composition of claim 24 further comprising a pharmaceutically acceptable carrier.

27. A composition capable of inducing an immune response in a mammalian subject, said composition comprising an adenovirus vector of any one of claims 4, 8, 9 or 16 and a pharmaceutically acceptable excipient.

28. A method for eliciting an immune response in a mammalian subject comprising administering a composition of claim 23 and a pharmaceutically acceptable excipient to said mammalian subject.

29. A method for eliciting an immune response in a mammalian subject comprising administering a composition of claim 24 and a pharmaceutically acceptable excipient to said mammalian subject.

30. The composition of claim 27 wherein the immune response is a humoral, cell-mediated, or mucosal immune response.

31. The composition of claim 27 wherein the mammal is a swine, a bovine, canine, or a human.

32. The composition of claim 27 wherein the adenovirus vector further comprises a nucleotide sequence that encodes a native or recombinant antigenic peptide.

33. The composition of claim 32 wherein the antigenic peptide is a human pathogen antigen.

34. The composition of claim 33 wherein the human pathogen antigen is an HIV virus antigen or a hepatitis virus antigen.

35. The composition of claim 32 wherein the antigenic peptide is a swine pathogen antigen.

36. The composition of claim 35 wherein the swine pathogen antigen selected from the group consisting of pseudorabies virus (PRV) gp50; transmissible gastroenteritis virus (TGEV) S gene; porcine rotavirus VP7 and VP8 genes; genes of porcine respiratory and reproductive syndrome virus (PRRS), in particular ORFs 3, 4 and 5; genes of porcine epidemic diarrhea virus; genes of hog cholera virus; genes of porcine parvovirus; and genes of porcine influenza virus.

37. The composition of claim 32 wherein the antigenic peptide is a bovine pathogen antigen.

38. The composition of claim 37 wherein the bovine pathogen antigen is selected from the group consisting of bovine herpes virus type 1; bovine diarrhea virus; and bovine coronavirus.

39. The recombinant adenovirus vector of claim 8 or 16 further comprising two inverted terminal repeat sequences from human adenovirus.

40. The recombinant adenovirus vector of claim 9 or 16 further comprising two inverted terminal repeat sequences from bovine adenovirus.

* * * * *